(12) United States Patent
Hutmacher et al.

(10) Patent No.: US 10,799,336 B2
(45) Date of Patent: Oct. 13, 2020

(54) MEDICAL/SURGICAL IMPLANT

(71) Applicant: Klinikum rechts der Isar der Technischen Universität München, Munich (DE)

(72) Inventors: Dietmar Werner Hutmacher, Belbowrie (AU); Jan-Thorsten Schantz, Langenargen (DE); Paul Severin Wiggenhauser, Munich (DE); Mohit Prashant Chhaya, Munich (DE)

(73) Assignee: Klinikum rechts der Isar der Technischen Universität München, Munich (DE)

( * ) Notice: Subject to any disclaimer, the term of this patent is extended or adjusted under 35 U.S.C. 154(b) by 0 days.

(21) Appl. No.: 15/509,550

(22) PCT Filed: Sep. 9, 2015

(86) PCT No.: PCT/EP2015/070599
§ 371 (c)(1),
(2) Date: Mar. 8, 2017

(87) PCT Pub. No.: WO2016/038083
PCT Pub. Date: Mar. 17, 2016

(65) Prior Publication Data
US 2017/0258574 A1    Sep. 14, 2017

(30) Foreign Application Priority Data

Sep. 9, 2014  (EP) ..................................... 14184126

(51) Int. Cl.
*A61F 2/12* (2006.01)
*A61L 27/18* (2006.01)
(Continued)

(52) U.S. Cl.
CPC ................ *A61F 2/12* (2013.01); *A61L 27/18* (2013.01); *A61L 27/28* (2013.01); *A61L 27/446* (2013.01);
(Continued)

(58) Field of Classification Search
CPC ................ A61F 2/12; A61F 2250/0024; A61F 2250/0026; A61F 2250/0031;
(Continued)

(56) References Cited

U.S. PATENT DOCUMENTS 3,515,128 A * 6/1970 McEvoy ................ A61B 10/02
30/130
4,978,355 A * 12/1990 Frey ..................... A61F 2/30907
623/23.54

(Continued)

FOREIGN PATENT DOCUMENTS

| CA | 2496184 A1 | 8/2005 |
| CA | 2866267 | 9/2013 |

(Continued)

OTHER PUBLICATIONS

International Searching Authority—EPO, International Search Report, PCT/EP2015/070599; dated Oct. 26, 2015. 4 pages.
(Continued)

*Primary Examiner* — Yashita Sharma
(74) *Attorney, Agent, or Firm* — Sunstein LLP

(57) ABSTRACT

The present invention relates to the field of implants. In particular, the present invention relates to an implant for tissue reconstruction which comprises a scaffold structure that includes a void system for the generation of prevascularized connective tissue with void spaces for cell and/or tissue transplantation. Moreover, the present invention relates to a method of manufacturing such an implant, to the internal architecture of such an implant, to a removal tool for (Continued)

mechanical removal of space-occupying structures from such an implant, to a kit comprising such an implant and such a removal tool, to a removal device for the removal of superparamagnetic or ferromagnetic space-occupying structures from such an implant, as well as to a guiding device for providing feedback to a surgeon during the procedure of introducing transplantation cells into the void spaces generated upon removal of space-occupying structures from such an implant.

22 Claims, 32 Drawing Sheets

(51) Int. Cl.
| | |
|---|---|
| A61L 27/44 | (2006.01) |
| A61L 27/56 | (2006.01) |
| A61L 27/28 | (2006.01) |
| A61L 27/50 | (2006.01) |
| A61L 27/54 | (2006.01) |
| A61L 27/58 | (2006.01) |
| A61F 2/00 | (2006.01) |

(52) U.S. Cl.
CPC .............. *A61L 27/50* (2013.01); *A61L 27/54* (2013.01); *A61L 27/56* (2013.01); *A61L 27/58* (2013.01); *A61F 2002/009* (2013.01); *A61F 2002/0081* (2013.01); *A61F 2002/0086* (2013.01); *A61F 2210/0004* (2013.01); *A61F 2210/009* (2013.01); *A61F 2250/0059* (2013.01); *A61F 2250/0063* (2013.01); *A61L 2300/416* (2013.01); *A61L 2400/16* (2013.01); *A61L 2430/04* (2013.01)

(58) Field of Classification Search
CPC .. A61F 2250/0052; A61L 27/44; A61L 27/50; A61L 27/58
See application file for complete search history.

(56) References Cited

U.S. PATENT DOCUMENTS

| | | | |
|---|---|---|---|
| 5,258,026 A | 11/1993 | Johnson et al. | |
| 5,290,271 A * | 3/1994 | Jernberg | A61F 2/06 424/473 |
| 5,380,328 A * | 1/1995 | Morgan | A61B 17/8071 606/70 |
| 5,716,404 A * | 2/1998 | Vacanti | A61L 27/3804 128/898 |
| 6,283,997 B1 * | 9/2001 | Garg | A61F 2/28 623/16.11 |
| 6,328,765 B1 | 12/2001 | Hardwick et al. | |
| 6,379,385 B1 * | 4/2002 | Kalas | A61F 2/28 623/16.11 |
| 6,520,997 B1 * | 2/2003 | Pekkarinen | A61F 2/00 623/23.72 |
| 6,585,765 B1 * | 7/2003 | Hossainy | A61L 27/34 427/2.24 |
| 6,993,406 B1 * | 1/2006 | Cesarano, III | A61F 2/28 424/422 |
| 8,202,305 B2 | 6/2012 | Reiley | |
| 9,034,571 B2 | 5/2015 | Berry et al. | |
| 9,724,203 B2 * | 8/2017 | Nebosky | A61F 2/44 |
| 2004/0075023 A1 * | 4/2004 | Assler | B32B 7/12 244/117 R |
| 2005/0027364 A1 * | 2/2005 | Kim | A61F 2/4425 623/17.13 |
| 2005/0060020 A1 * | 3/2005 | Jenson | A61F 2/07 623/1.13 |
| 2005/0112397 A1 * | 5/2005 | Rolfe | A61B 17/8605 428/593 |
| 2005/0177249 A1 | 8/2005 | Kladakis et al. | |
| 2006/0025848 A1 * | 2/2006 | Weber | A61F 2/82 623/1.15 |
| 2007/0141111 A1 * | 6/2007 | Suokas | A61F 2/28 424/426 |
| 2007/0260324 A1 * | 11/2007 | Joshi | A61F 2/4465 623/23.51 |
| 2007/0299518 A1 * | 12/2007 | Ruane | A61L 27/34 623/11.11 |
| 2008/0300681 A1 | 12/2008 | Rigotti et al. | |
| 2009/0082810 A1 | 3/2009 | Bhatnagar et al. | |
| 2009/0198333 A1 * | 8/2009 | Becker | A61F 2/0077 623/8 |
| 2010/0161061 A1 * | 6/2010 | Hunt | A61F 2/28 623/17.16 |
| 2010/0196433 A1 | 8/2010 | Williams et al. | |
| 2010/0226943 A1 * | 9/2010 | Brennan | A61L 2/02 424/400 |
| 2010/0292738 A1 | 11/2010 | Reiley | |
| 2010/0304007 A1 * | 12/2010 | Dave | A61F 2/91 427/2.25 |
| 2010/0305696 A1 * | 12/2010 | Mao | A61L 27/18 623/8 |
| 2011/0245905 A1 * | 10/2011 | Weber | A61L 31/044 623/1.15 |
| 2012/0143329 A1 * | 6/2012 | Kim | A61F 2/12 623/8 |
| 2014/0243995 A1 * | 8/2014 | Kolewe | A61L 27/18 623/23.72 |
| 2014/0296996 A1 * | 10/2014 | Shim | A61F 2/28 623/23.51 |
| 2017/0224471 A1 * | 8/2017 | Rehnke | A61F 2/12 |

FOREIGN PATENT DOCUMENTS

| | | |
|---|---|---|
| CN | 1461220 A | 12/2003 |
| CN | 101282652 A | 10/2008 |
| EP | 1135083 A2 | 9/2001 |
| JP | 07-148243 | 6/1995 |
| JP | 10-510736 | 10/1998 |
| JP | 2008-505093 | 2/2008 |
| JP | 2010-540000 | 12/2010 |
| WO | WO 96/18424 | 6/1996 |
| WO | WO 2006/014270 A2 | 2/2006 |
| WO | WO 2008/150895 A1 | 12/2008 |
| WO | WO 2011/137394 | 11/2011 |

OTHER PUBLICATIONS

International Searching Authority—EPO, Written Opinion, PCT/EP2015/070599; dated Oct. 26, 2015. 6 pages.
China National Intellectual Property Administration, Office Action, Application No. 201580045777.2, dated Jul. 23, 2019, 5 pages.
Jan Henkel et al., "Design and fabrication of scaffold-based tissue engineering," BioNanoMat 2013; 14(3-4), pp. 171-193.
Daniel J. Tilkorn, M.D. et al., "Implanted Myoblast Survival Is Dependent on the Degree of Vascularization in a Novel Delayed Implantation/Prevascularization Tissue Engineering Model," Tissue Engineering: Part A, vol. 16, No. 1 (2010); pp. 165-178.

* cited by examiner

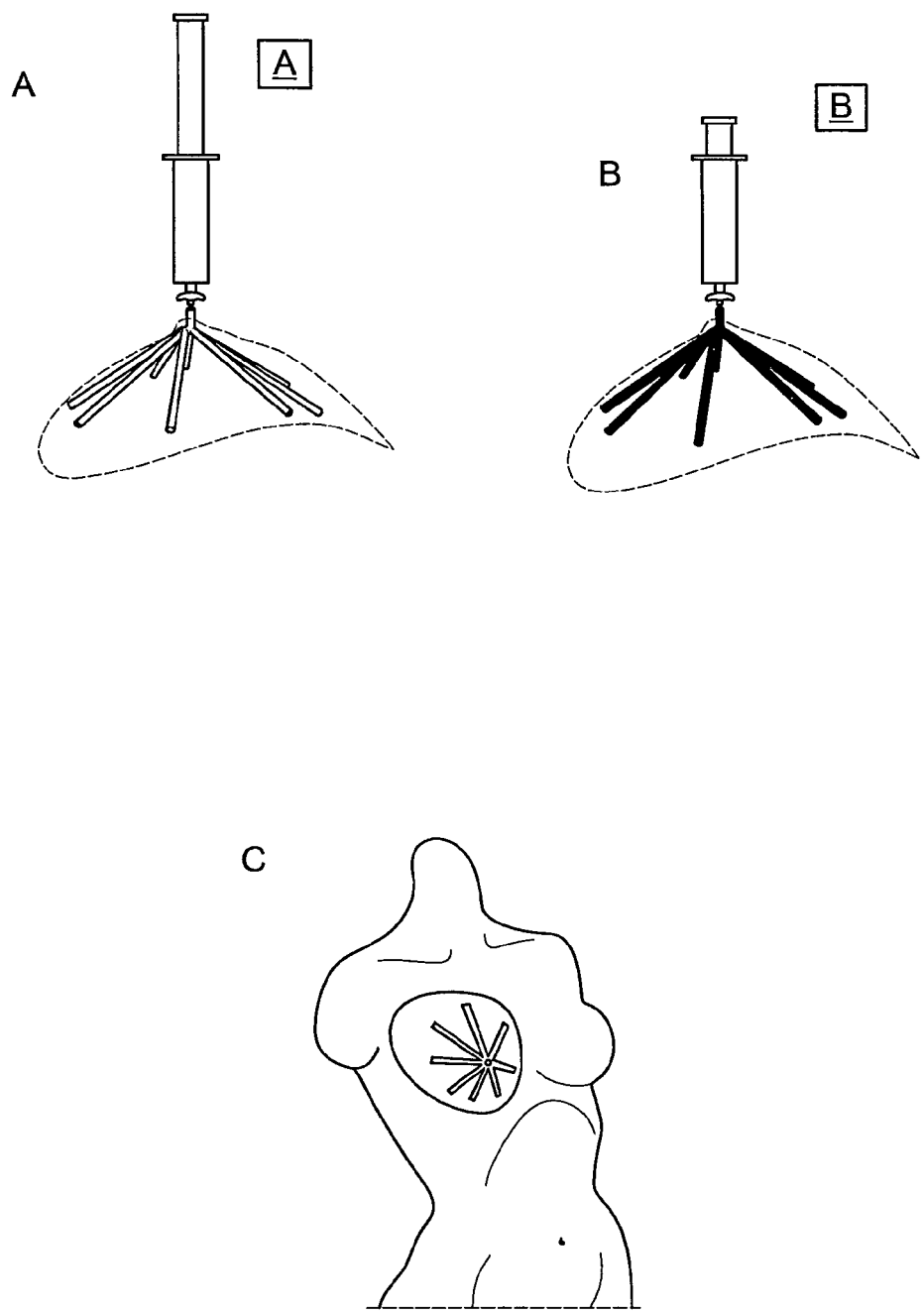
Fig. 3 (A-C)

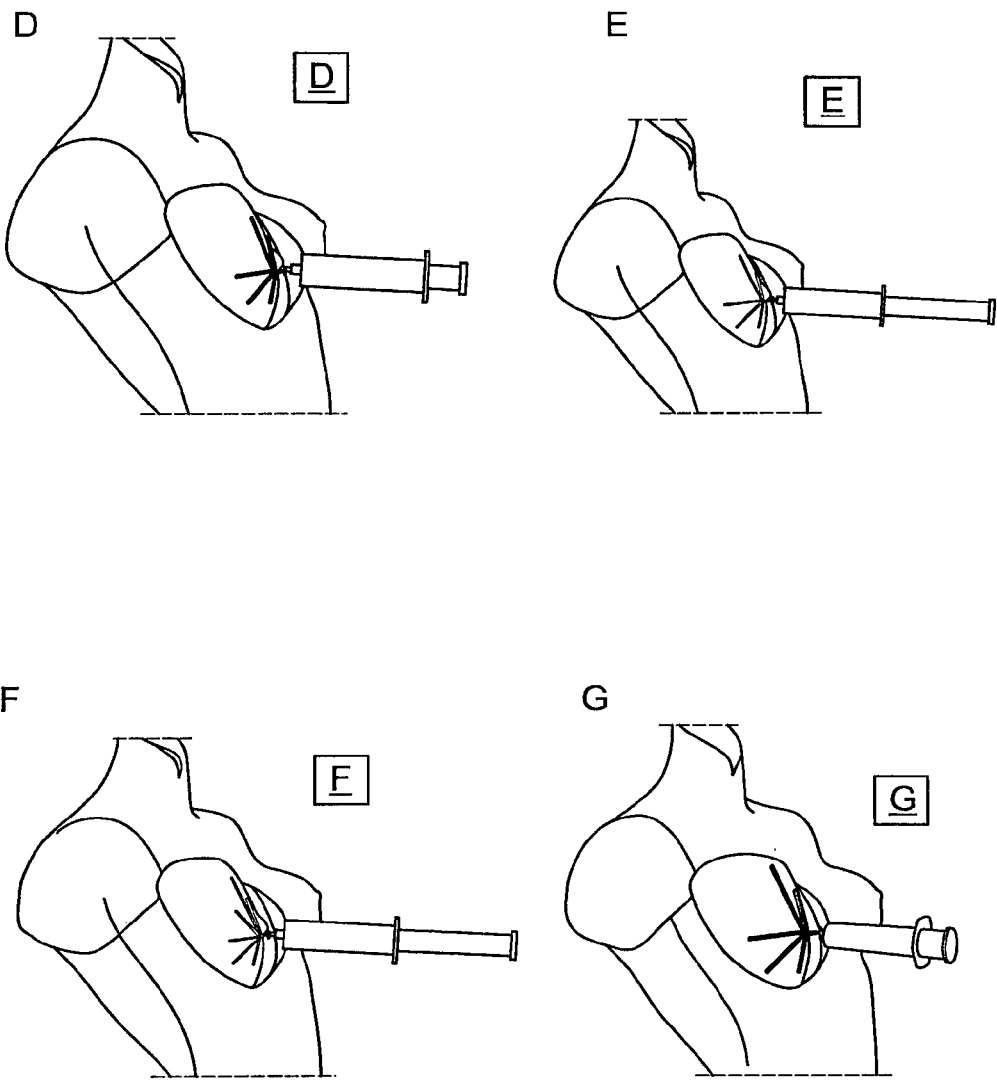
Fig. 3 (D-G)

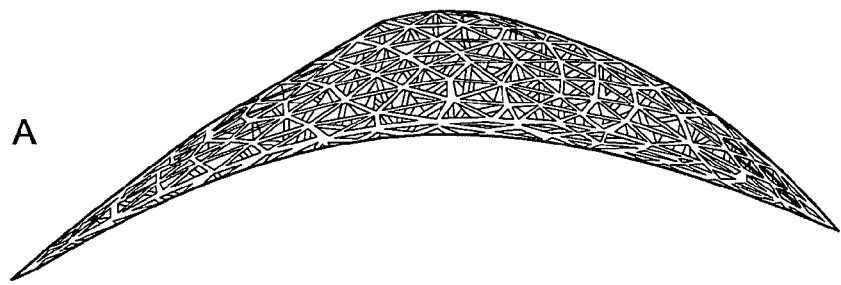
Fig. 4

A 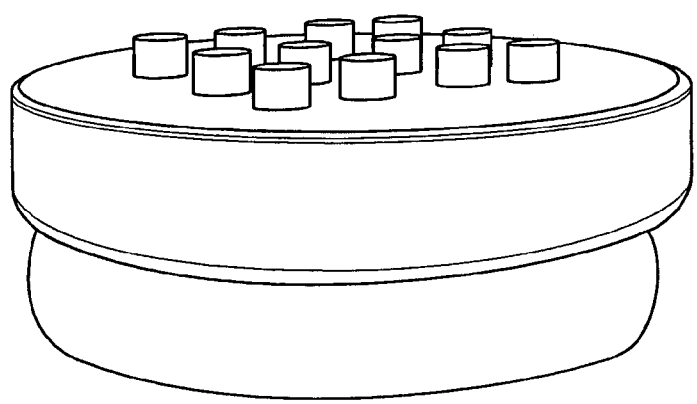
B 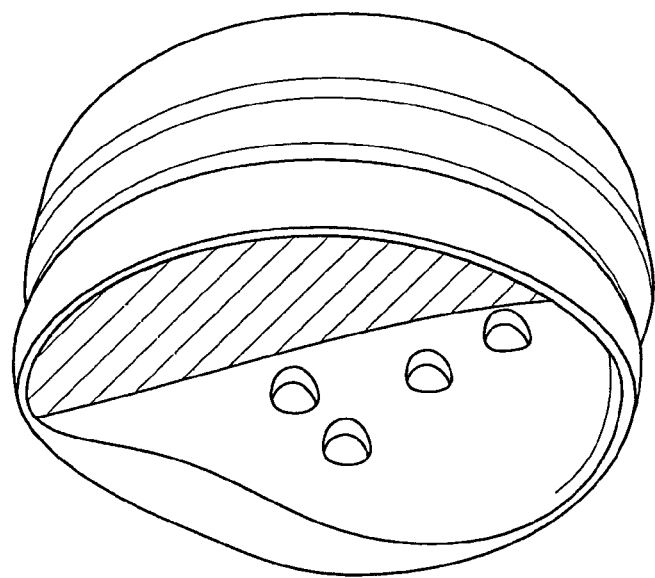
Fig. 6

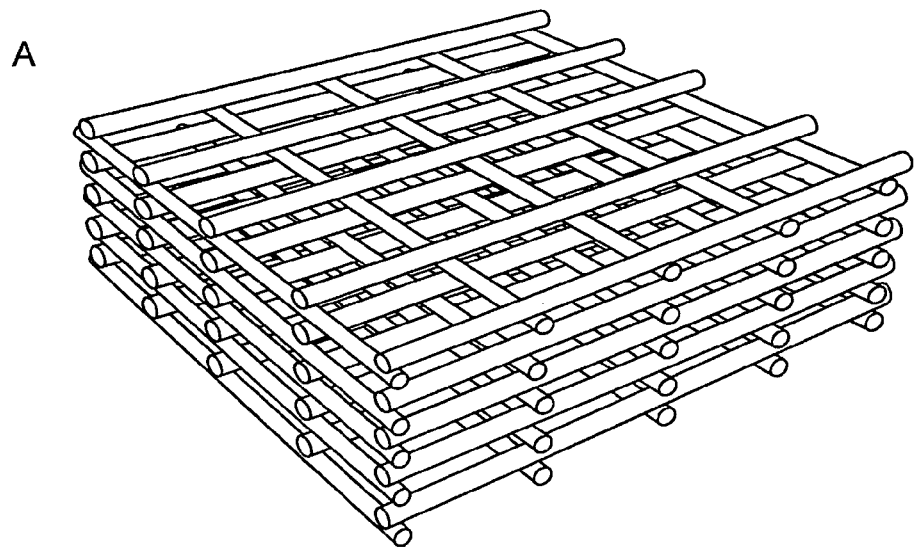
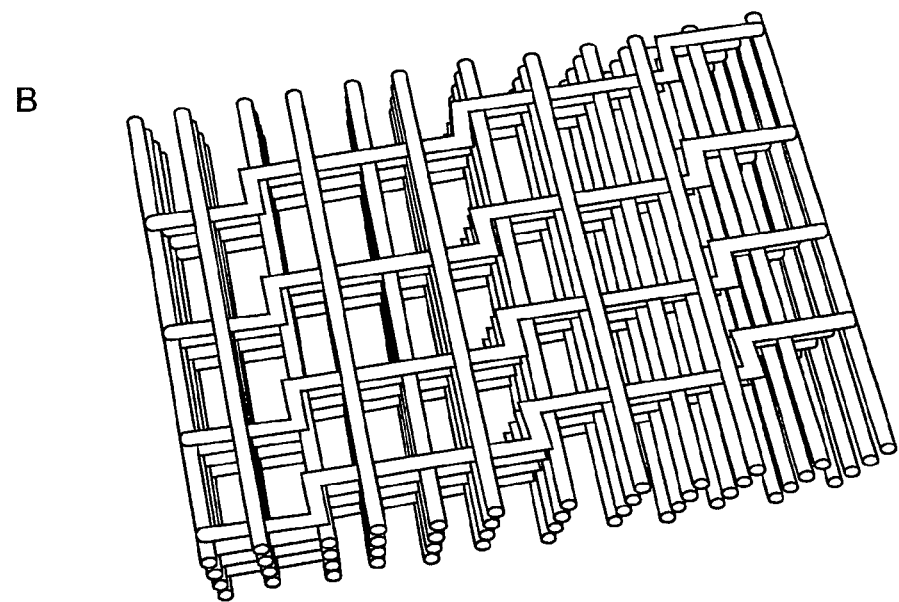
Fig. 9 (A, B)

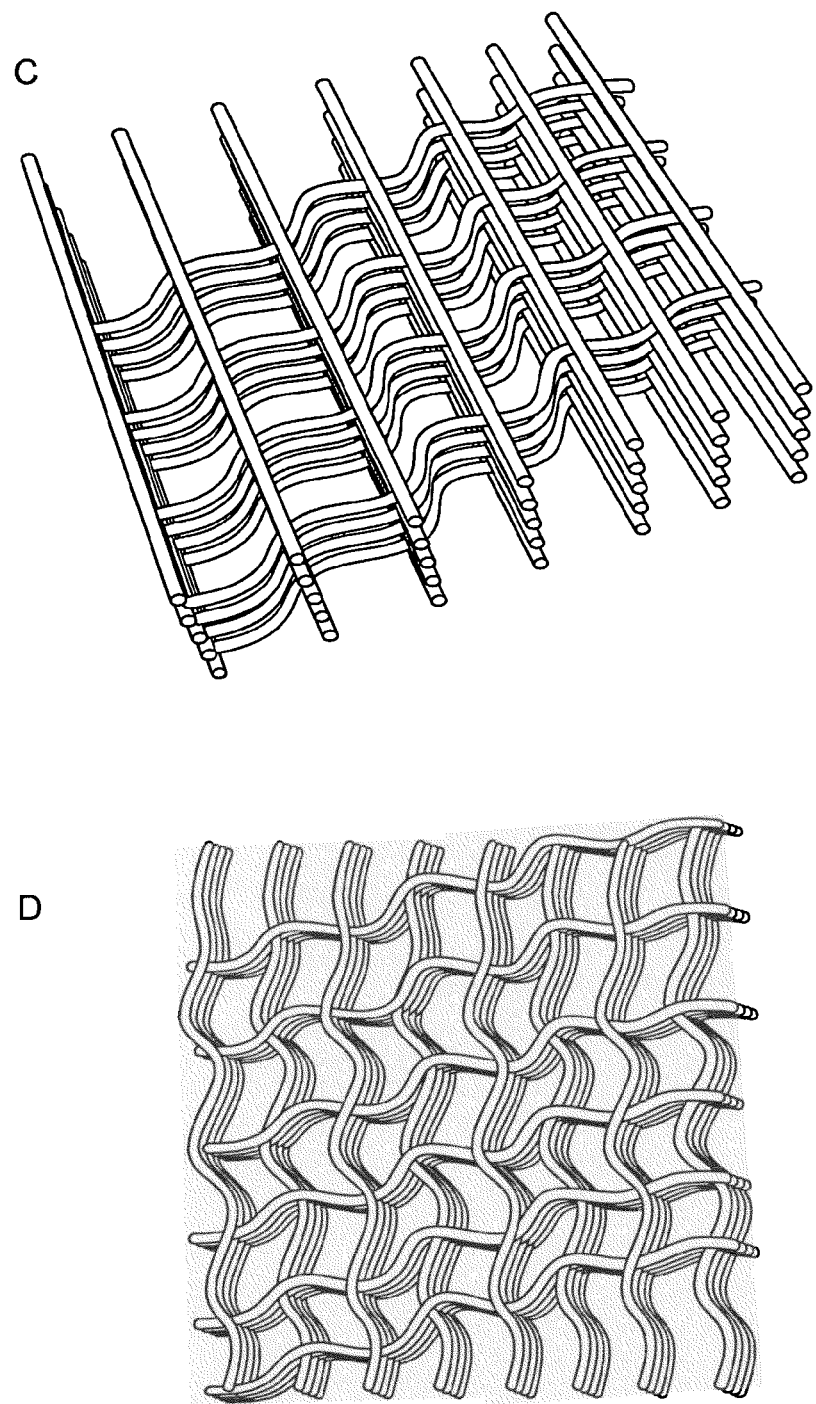
Fig. 9 (C, D)

A
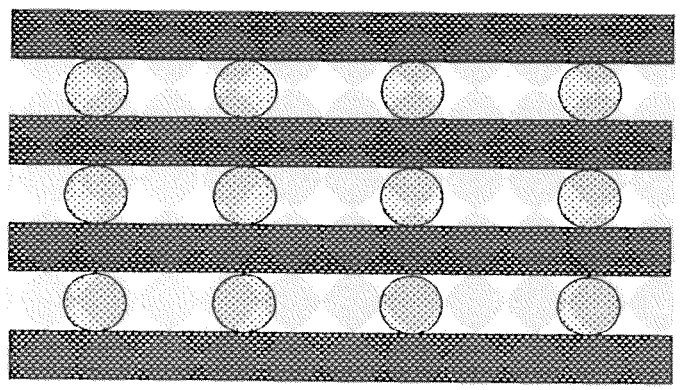
B
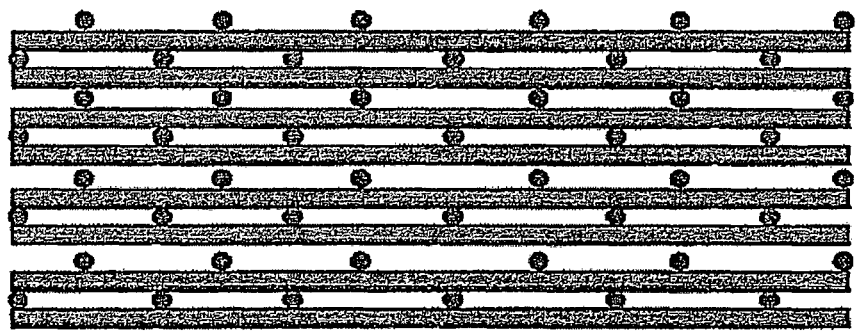
Fig. 10

A
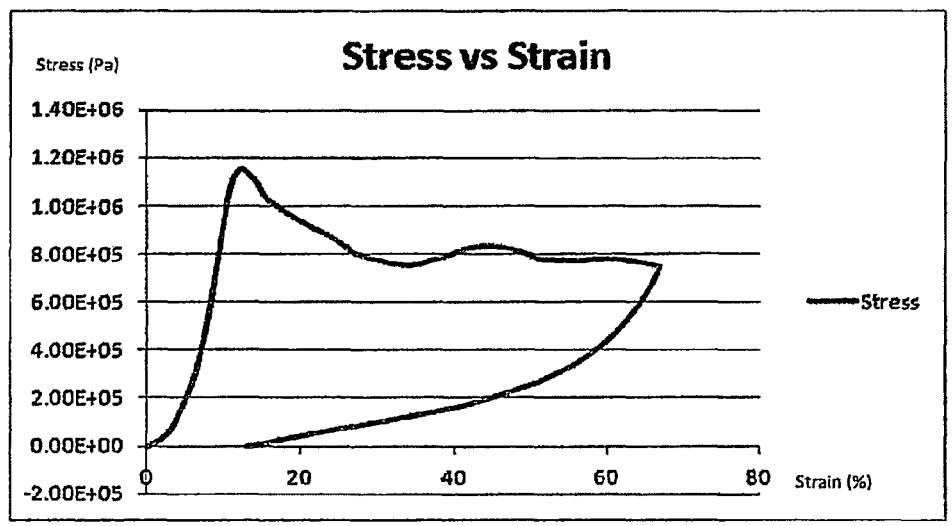
B
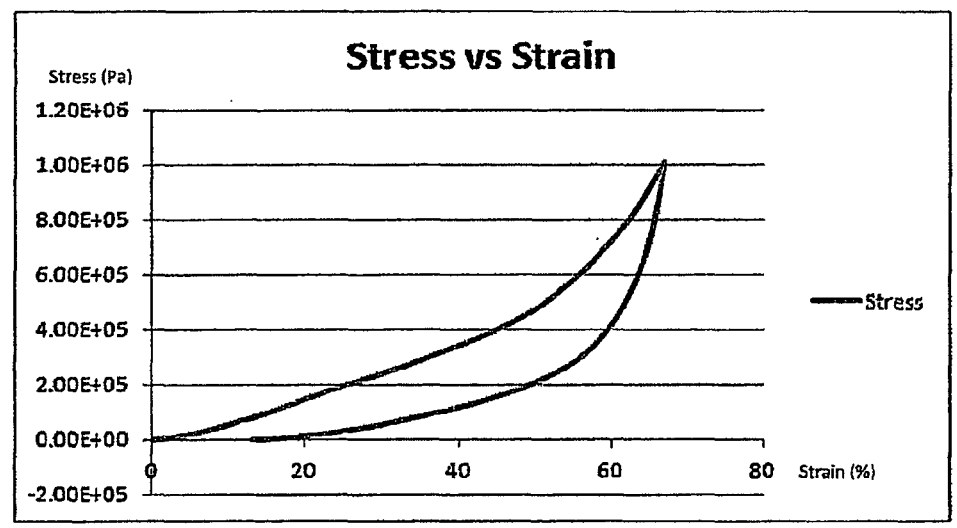
Fig. 11 (A, B)

C
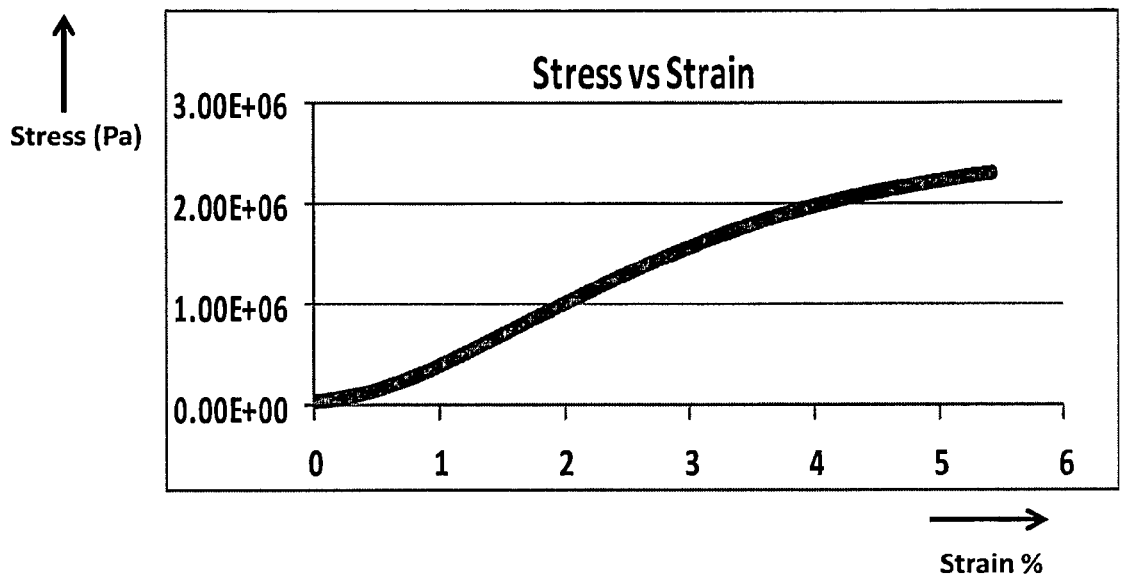
D
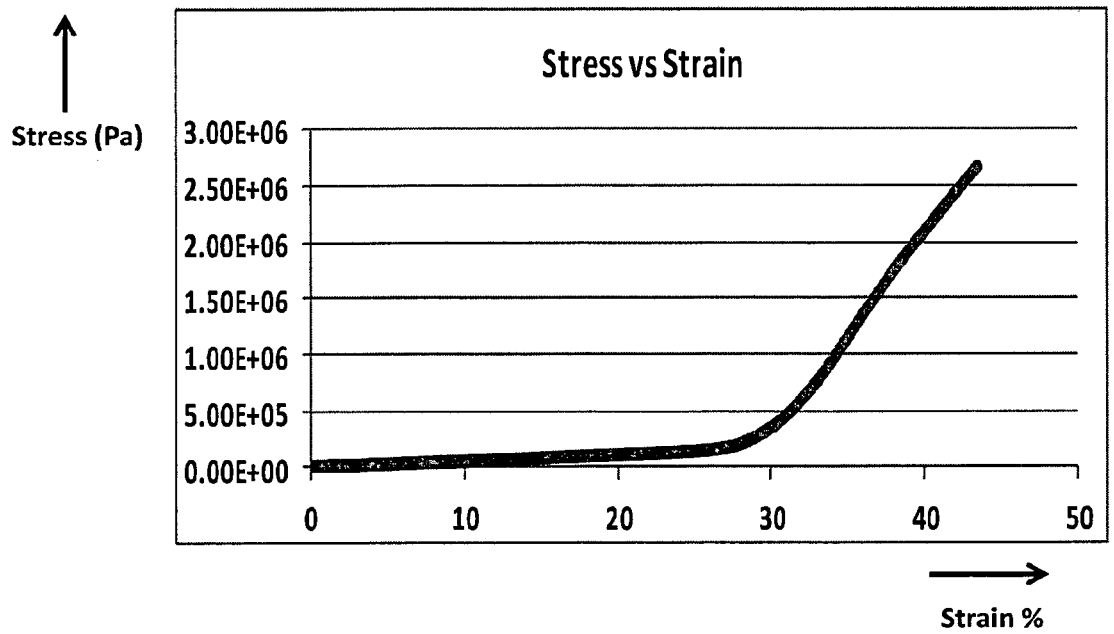
Fig. 11 (C, D)

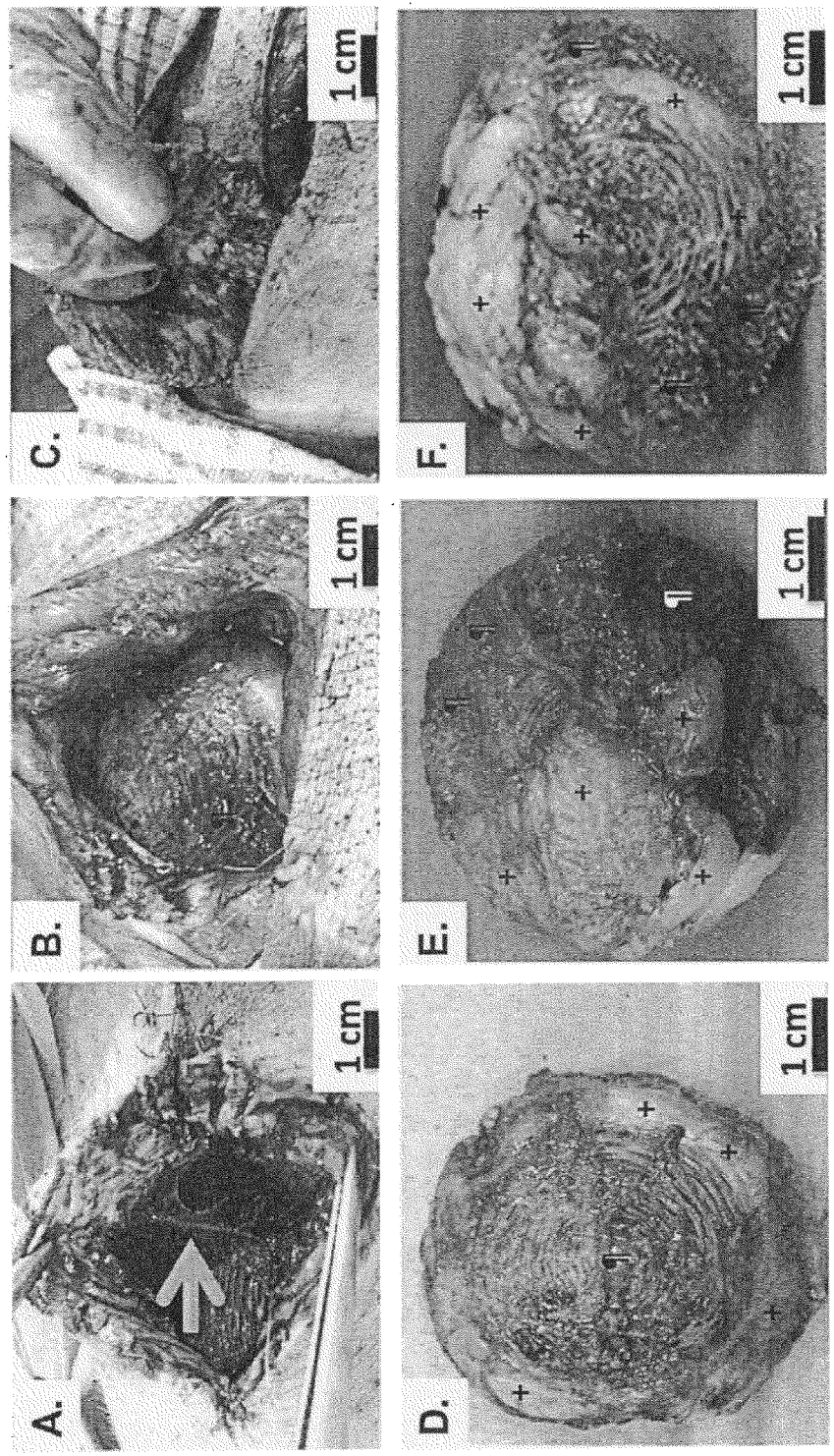
Fig. 14 (A-F)

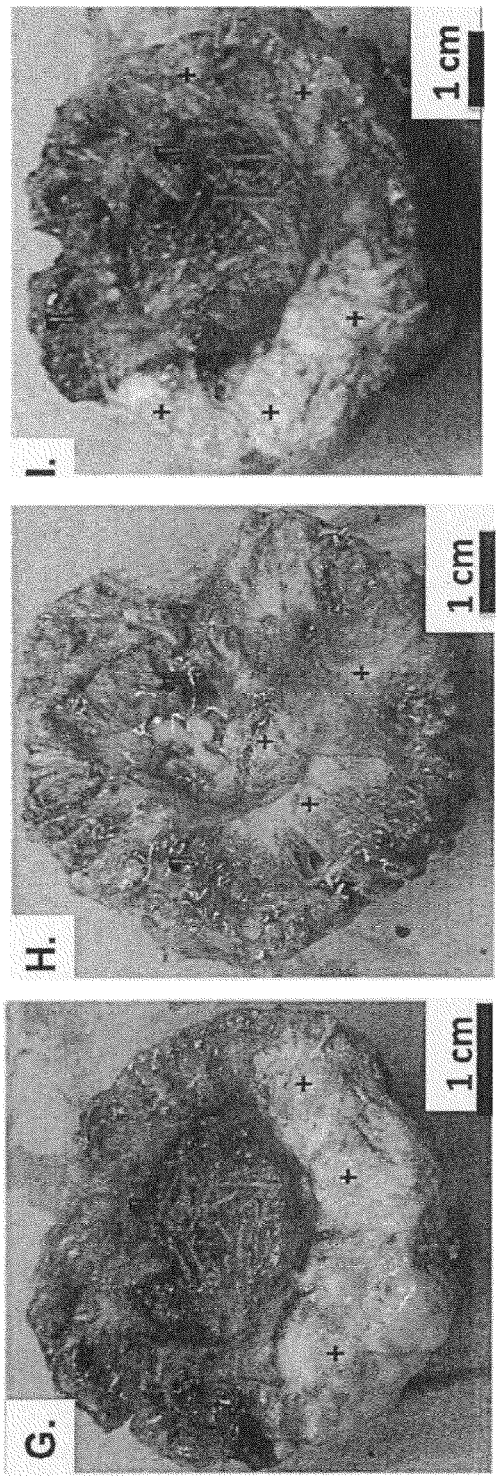
Fig. 14 (G-I)

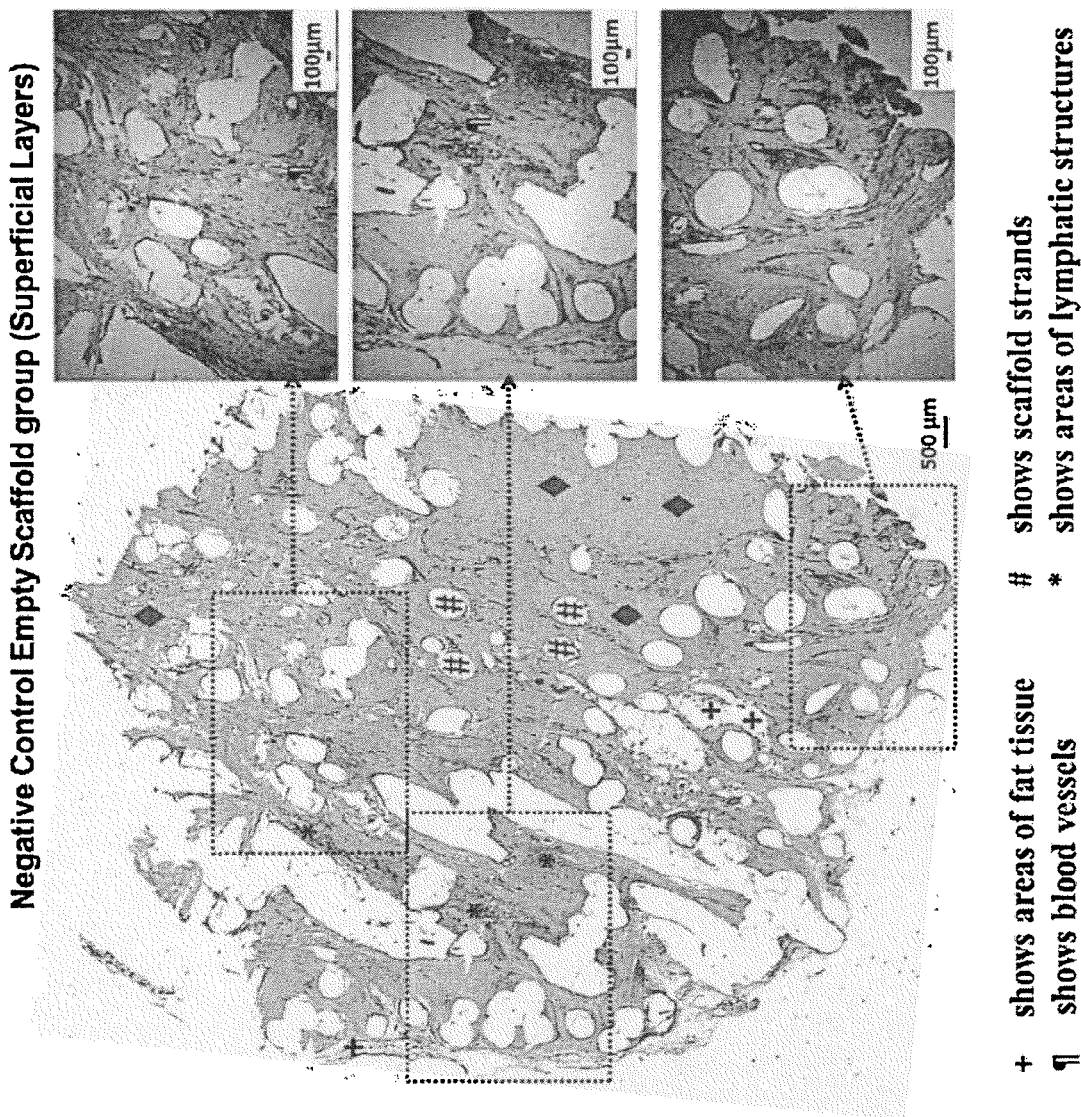
Fig. 15 (LEFT)

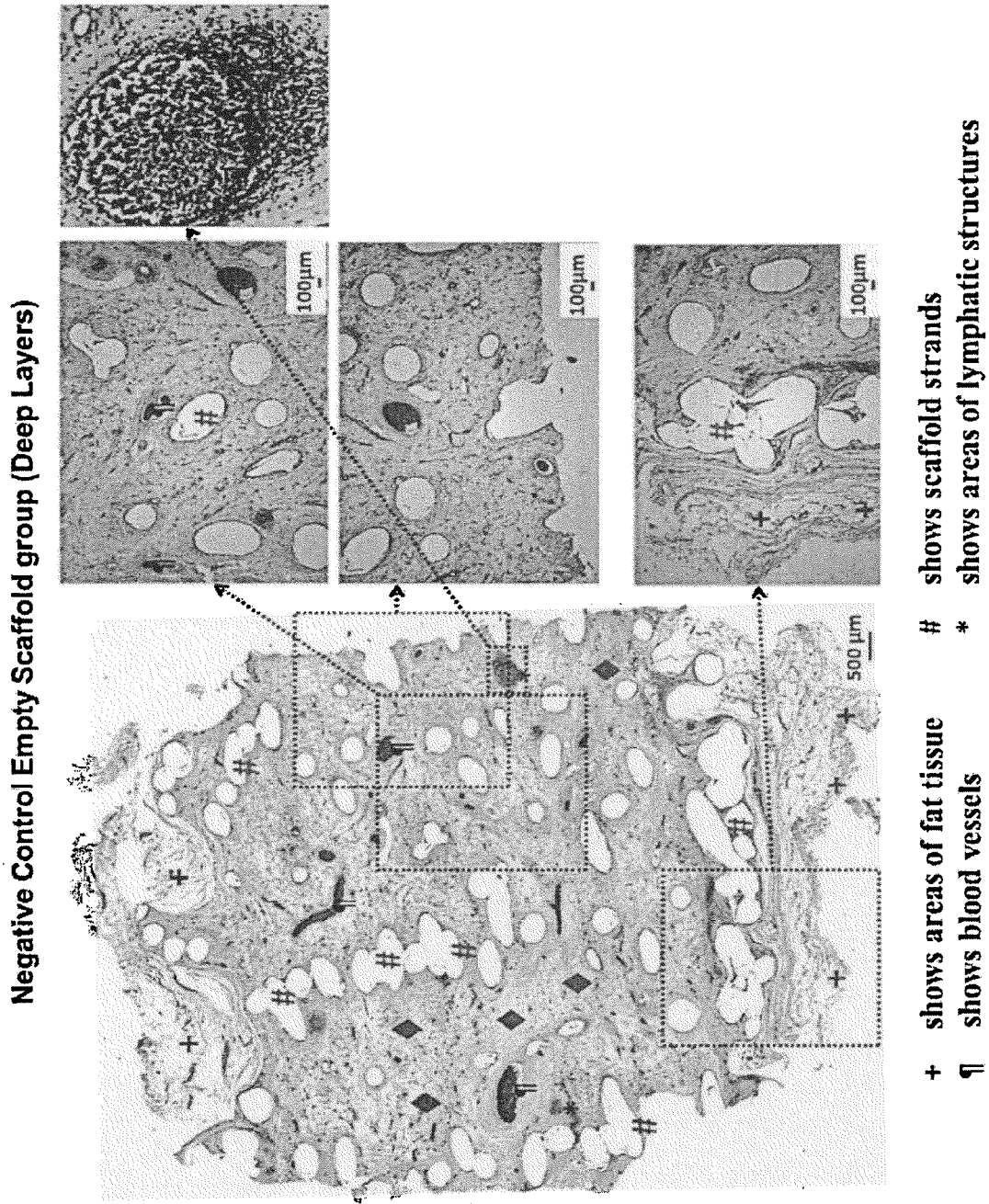
Fig. 15 (RIGHT)

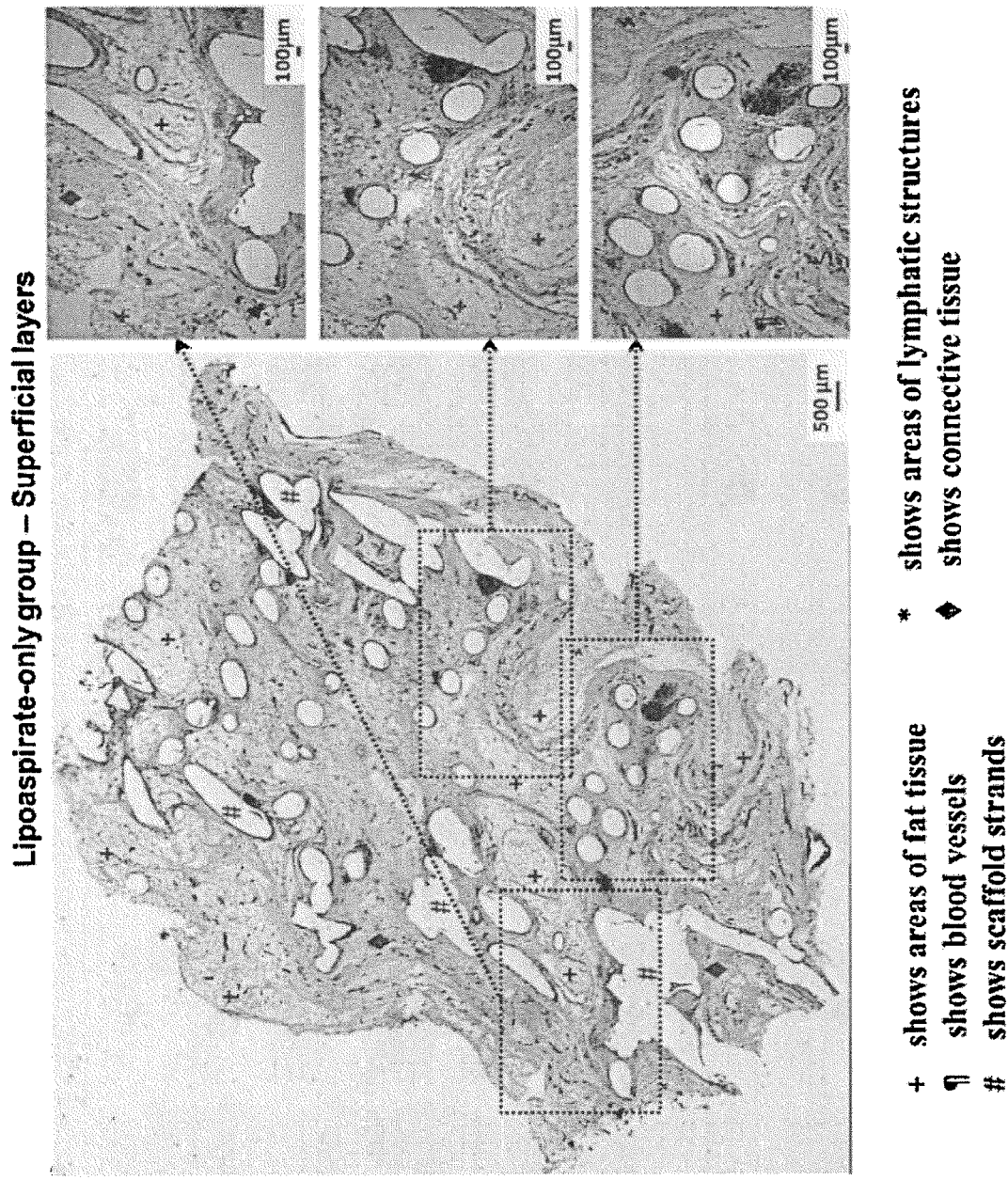
Fig. 16 (LEFT)

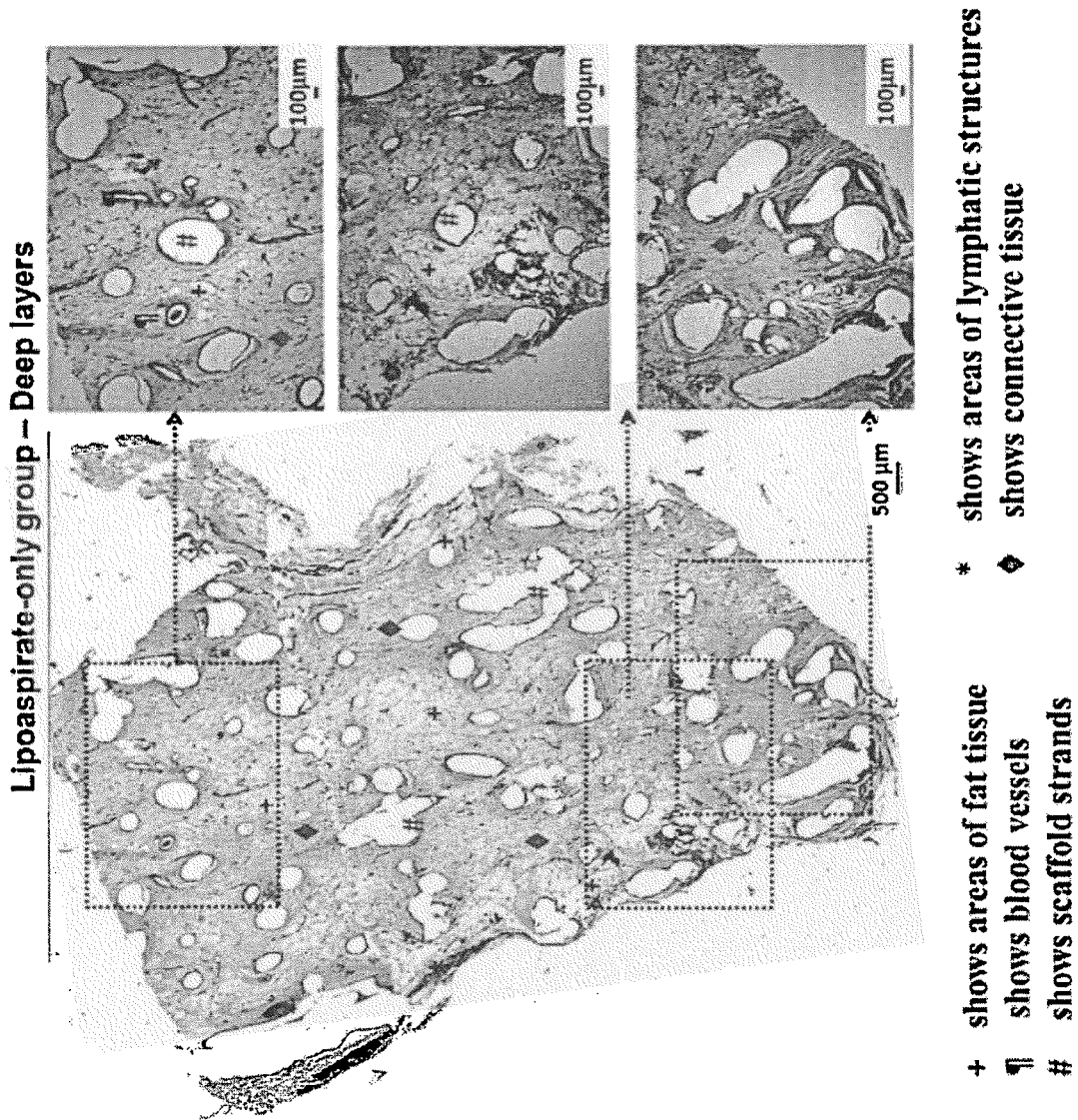
Fig. 16 (RIGHT)

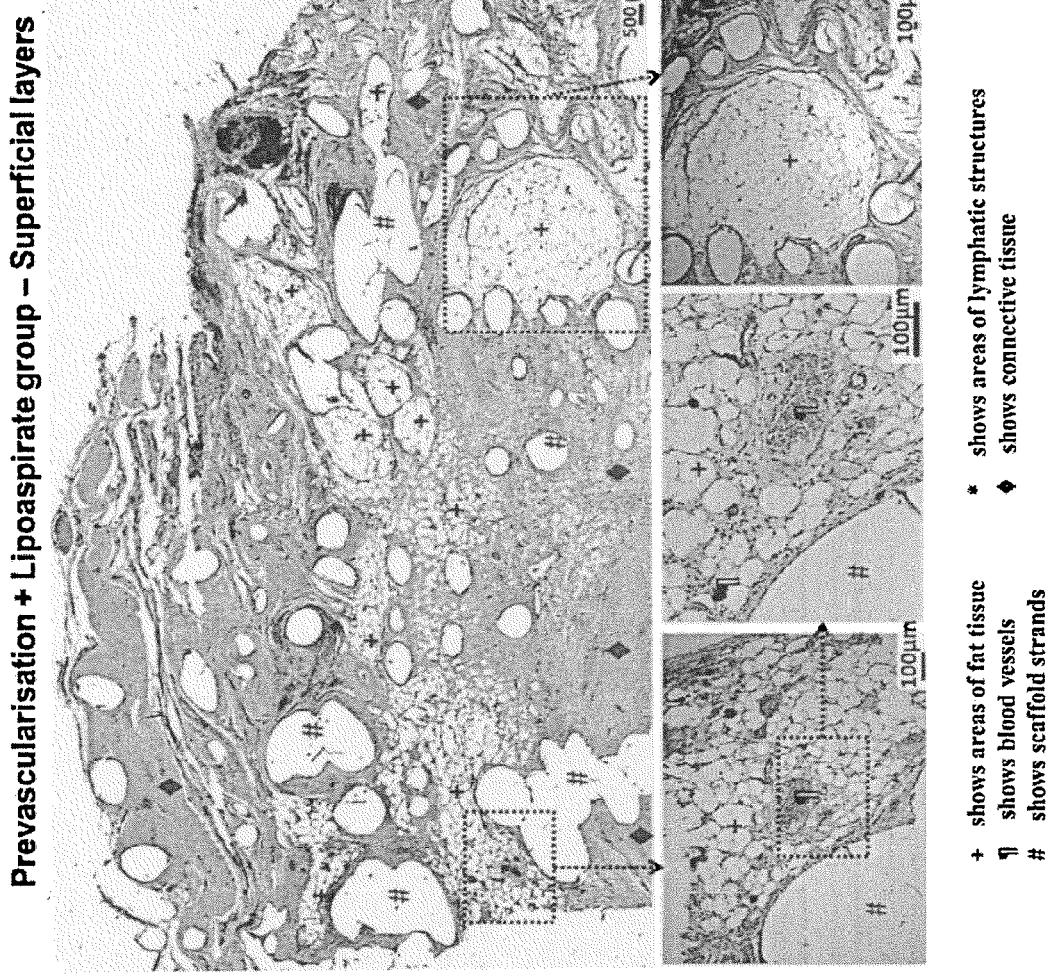
Fig. 17 (LEFT)

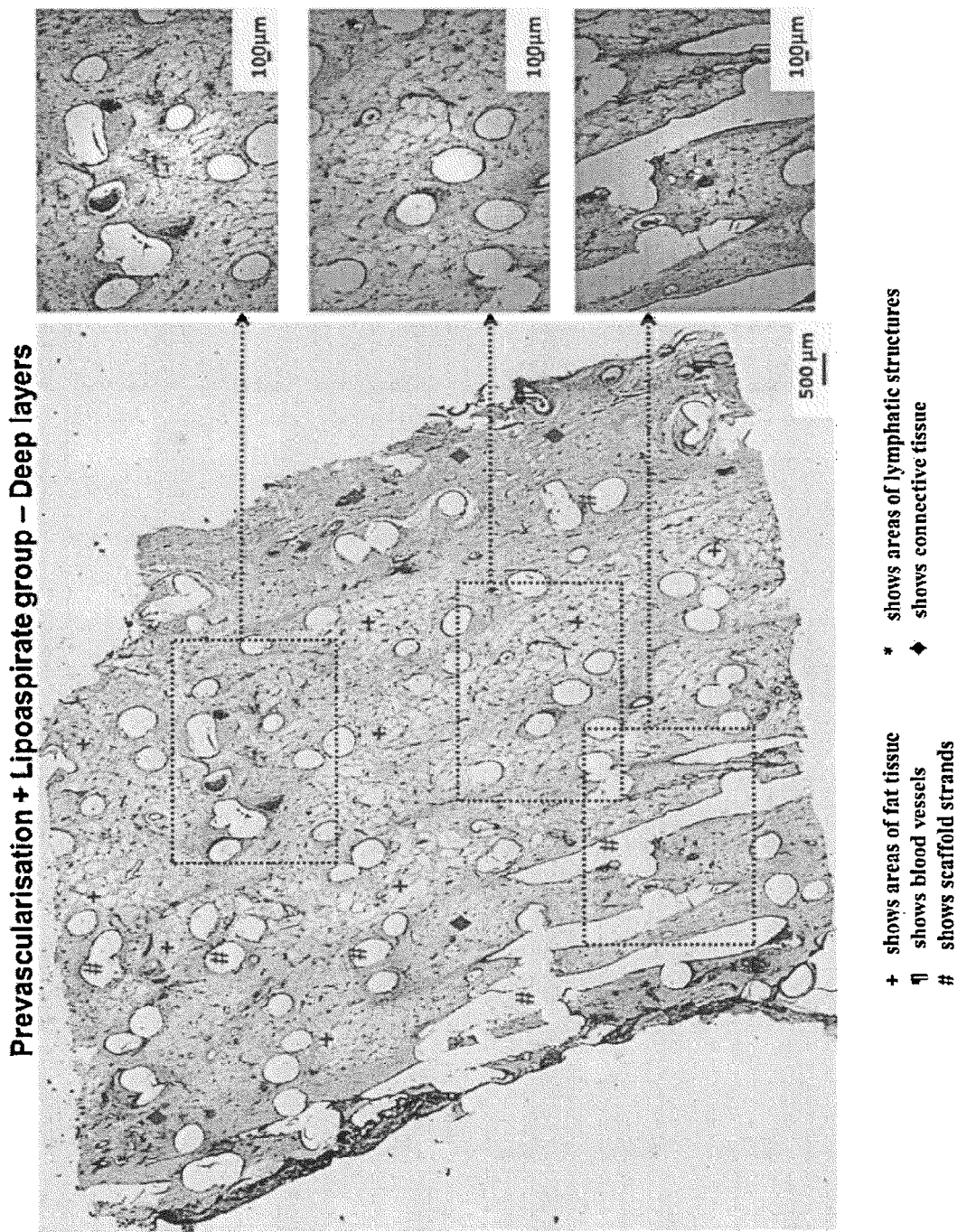
Fig. 17 (RIGHT)

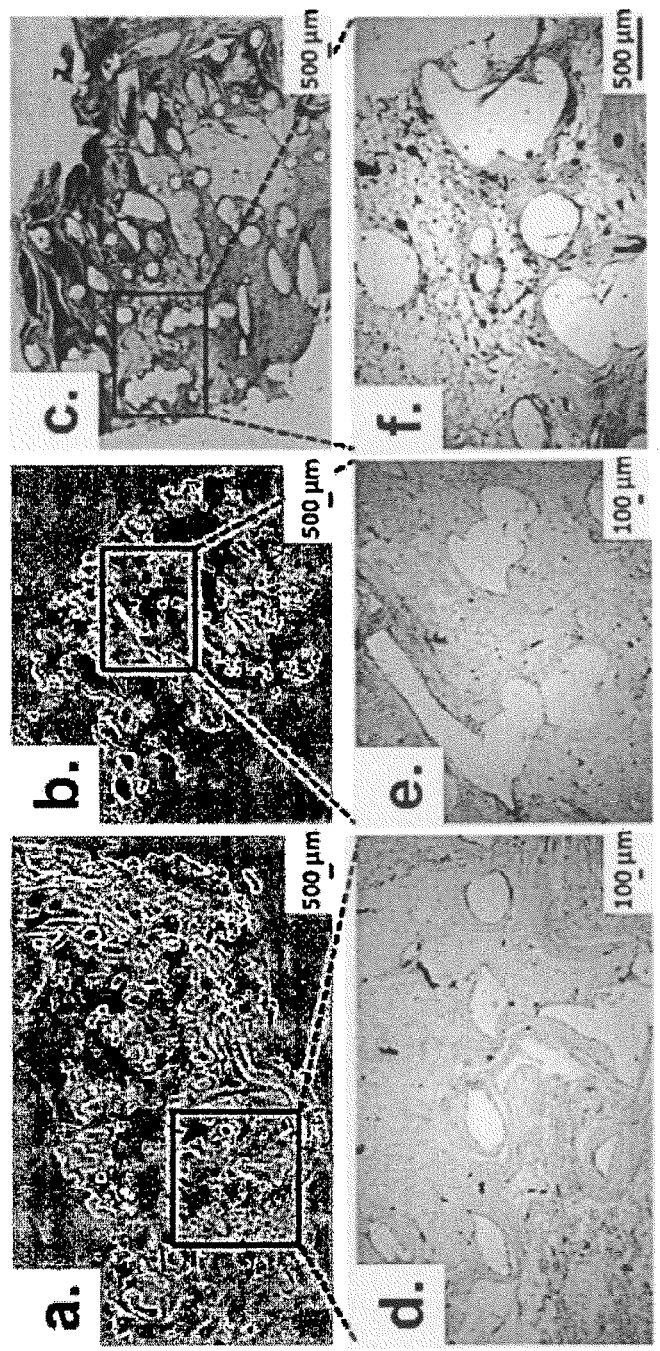
Fig. 19 (A-F)

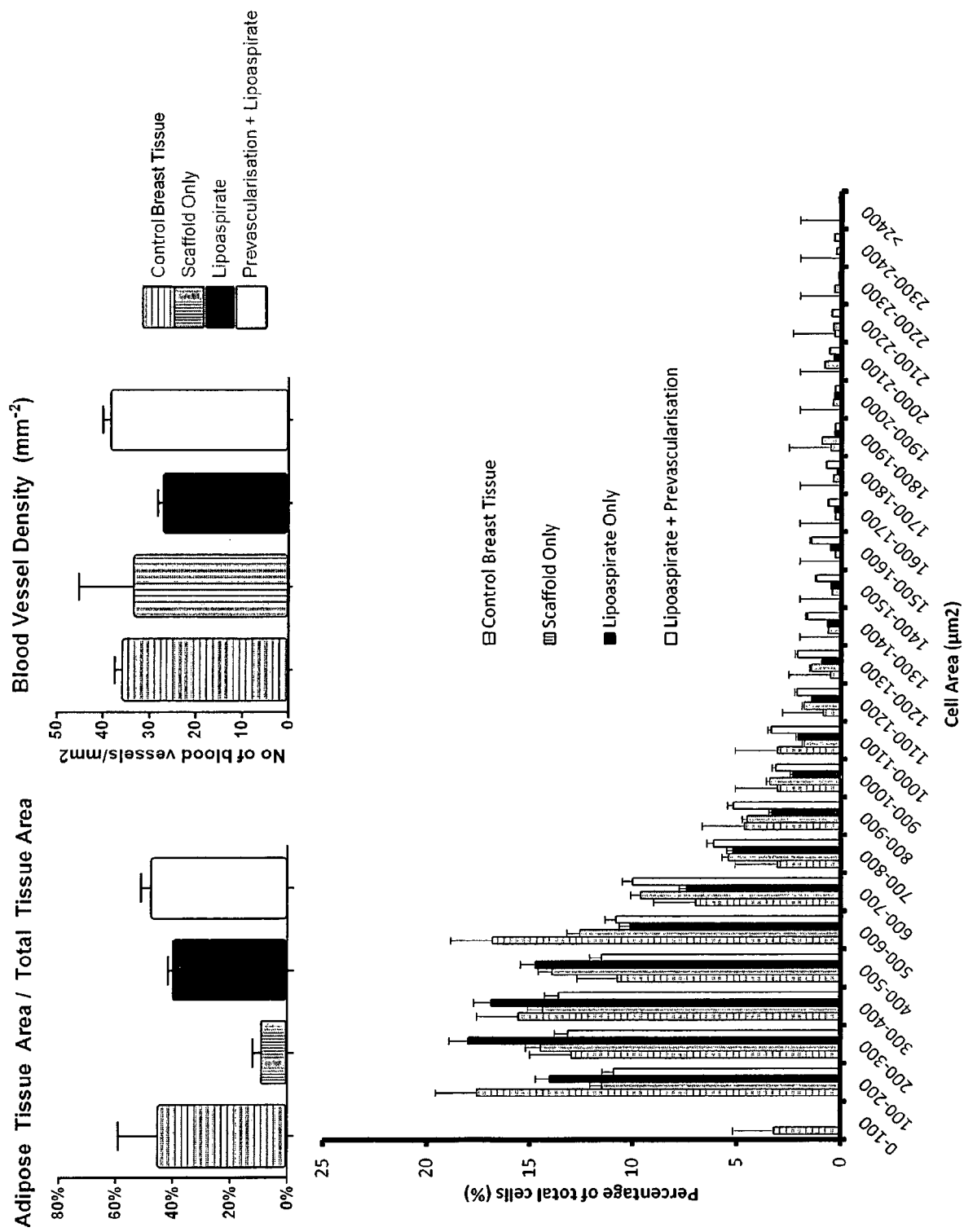
Fig. 19 (G-I)

+ shows areas of fat tissue
¶ shows blood vessels
shows scaffold strands
* shows areas of lymphatic structures
♦ shows connective tissue A 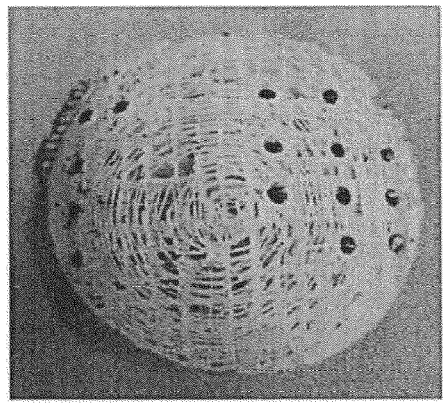
B 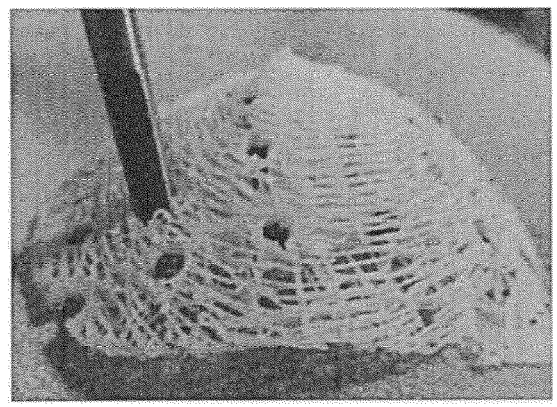
C 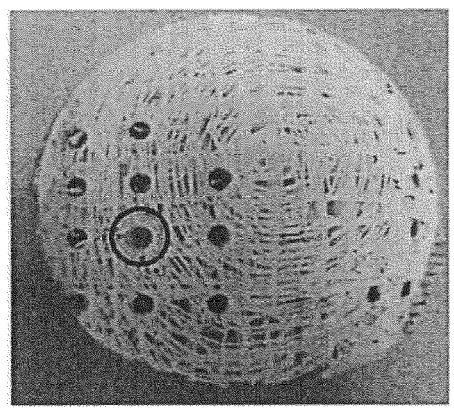
Fig. 21

MEDICAL/SURGICAL IMPLANT

CROSS-REFERENCE TO RELATED APPLICATIONS

This Application is a U.S. national stage entry under 35 USC § 371 of PCT/EP2015/070599 filed Sep. 9, 2015, which claims priority to European Patent Application 1418426.2, filed Sep. 9, 2014; both of which are incorporated herein by reference in their entireties.

FIELD OF THE INVENTION

The present invention relates to the field of implants. In particular, the present invention relates to an implant for tissue reconstruction which comprises a scaffold structure that includes a void system for the generation of prevascularized connective tissue with void spaces for cell or tissue transplantation. Moreover, the present invention relates to a method of manufacturing such an implant, to the internal architecture of such an implant, to a removal tool for mechanical removal of space-occupying structures from such an implant, to a kit comprising such an implant and such a removal tool, to a removal device for the removal of superparamagnetic or ferromagnetic space-occupying structures from such an implant, as well as to a guiding device for providing feedback to a surgeon during the procedure of introducing transplantation cells into the void spaces generated upon removal of space-occupying structures from such an implant.

BACKGROUND OF THE INVENTION

In recent years, there have been significant advances in medical techniques for the replacement and/or reconstruction of lost body tissues, mostly due to innovative developments in the fields of surgery, material science and bioengineering.

There are various medical conditions where replacement or reconstruction of lost body tissues becomes an important treatment option. Such medical conditions include trauma, tumor removal, diverse chronic diseases and certain congenital anomalies.

A typical example of a medical condition where tissue replacement/reconstruction is often carried out is breast cancer. Breast cancer is a major cause of illness for women, being responsible for about 375,000 deaths globally in the year 2000. The most common surgical procedures to remove the tumor are lumpectomy, i.e. partial removal of breast tissue, and total mastectomy, i.e. total removal of the breast. Such procedures have a negative psychological effect on the well-being of the patient. Mastectomy, for example, has been shown to be directly related to a psychological syndrome "marked by anxiety, insomnia, depressive attitudes, occasional ideas of suicide, and feelings of shame and worthlessness" (Renneker and Cutler). Owing to the large number of occurrences of breast cancer, breast reconstruction is becoming increasingly common. In 2011, there were more than 300,000 breast reconstruction procedures performed in the USA alone.

The breasts are located on the anterior and lateral parts of the chest, and their primary role is to provide milk for nourishment of the infant. Anatomically, the breast is composed of internal and external parts. The external parts include the nipple, areola and tubercles. The internal part, which is also the principal secretory organ, is formed by 15-25 lobes of compound milk-producing glands embedded in fibrous and adipose tissue. Structurally, the adipose tissue is interspersed between these glands and connective tissue. A high density of vascularization is crucial for the survival of the glandular and adipose tissue.

As for current approaches aimed at breast reconstruction, at present there are three main strategies for reconstructive surgery following lumpectomy or mastectomy: prosthetic implant-based reconstruction, reconstruction with autologous tissue and de novo tissue engineering.

1) Reconstruction with Prosthetic Implants

Prosthetic implant-based reconstruction is a relatively straight-forward surgical approach that is based on the implantation of prosthetic devices. The advantage of using such devices is that they can be manufactured in a broad range of sizes, contours, profiles and textures. There are two major types of prosthetic implants: fixed-volume implants and tissue expanders.

a) Fixed-volume implants

The fixed-volume breast implant is a single lumen implant made of silicone elastomer that is filled with a fixed volume of saline solution during implantation surgery. After the operation no adjustments can be made to the saline volume. The saline solution may also be replaced with silicone.

However, controversy still exists with regard to the association of silicone-based implants with numerous health problems, such as formation of a rigid fibrous tissue surrounding the implant, causing significant soft tissue irritation via capsular contracture and giving, from a cosmetic point of view, an undesirable appearance to the breast. Moreover, it has been found that siloxanes and platinum could leak out of such implants and their levels were elevated in the fatty tissues of a woman with such a leaking implant (Flassbeck et al.).

b) Tissue Expanders

A tissue expander resembles an inflatable breast implant. It is placed in its collapsed form during the surgical procedure and is gradually inflated by the injection of saline over the course of weeks to months. When the expansion is complete, it is either replaced with a permanent saline- or silicone-based implant, or left inside.

Perhaps the biggest disadvantage with using prosthetic implants is that of capsular contracture. Multiple studies have demonstrated that inserting such an implant leads to a foreign body reaction resulting in the formation of a capsule of fibrous tissue around the implant. This ultimately leads to an unnatural hemispherical appearance of the breast and restricted shoulder or arm movement. Frequencies of occurrence of capsular contracture have been found to lie in the range of 2-70%, depending on the study and the patient cohort investigated. The average reported capsular contracture risk is approximately 10%. This risk of capsular contracture also rises significantly when the breasts are irradiated subsequent to implantation.

In addition, both types of implants may also be subject to rupture, displacement, deformation, chronic seroma, hematoma and loss of nipple sensation. Because of such reasons, breast reconstruction using implants is not a completely sustainable solution.

2) Transplantation of Fat Tissue

This approach for breast reconstruction relies on the transplantation of autologous fat tissue rather than prosthetic implants. There are two variants of this strategy that are used in the clinic: autologous fat transplantation and free tissue transfer flaps.

a) Autologous fat transplantation

This method involves using liposuction to transfer fat from a donor site within the patient's body to the breast region as hundreds of tiny droplets (called a lipoaspirate). The full breast can then be reconstructed with repeated sessions of fat transfer.

However, without a structural support, the newly injected fat quickly gets remodeled by the body after 2-3 months—thus requiring 3-4 additional lipotransfer sessions before the tissue stabilises. Furthermore, lipotransfer of large amounts of adipose tissue bears the risk of adipose tissue necrosis owing to insufficient vascularisation—ultimately leading to formation of oil cysts.

Thus, autologous fat transplantations yield poor results, with 40-60% reduction in graft volume owing to tissue resorption and necrosis. Insufficient vascularization is thought to be one of the causes leading to such a reduction in adipose volume.

b) Free tissue transfer flaps

This method differs from autologous fat transplantation in that in free tissue transfer flaps the tissue is transferred along with its blood vessels. The blood vessels within the flap are then connected with the vessels at the recipient site.

There are several different donor sites which can be used as source for flap tissue. The most favored of these are at present the Transverse Rectus Abdominis Musculocutaneous (TRAM) flap and the Deep Inferior Epigastric Perforator (DIEP) flap.

The main complication arising with free tissue transfer flaps is that sometimes a clot forms in the vein that drains the blood from the flap or the artery that supplies blood to the flap. Both cases may lead to necrosis of the flap tissue. Other inherent risks include total/partial flap loss and abdominal bulge or hernia. The incidence of complications after TRAM flap reconstruction in the breast region ranges from 1 to 82 percent depending on the patient cohort studied. DIEP flaps also suffer from breast-related morbidity issues, including a fat necrosis ranging from 6 to 62.5 percent.

3) De Novo Adipose Tissue Engineering

De novo adipose tissue engineering is an approach based on recent progress in the field of tissue engineering. Human adipose tissue-derived stem cells (hASCs), fibroblast-like stem cells that differentiate into mature adipocytes, are seeded onto a biodegradable scaffold where they promote the formation of adipose tissue. While this approach is not yet used in clinical practice, numerous in vivo proof-of-concept studies have been conducted to translate adipose tissue engineering to the clinic.

The main advantage of de novo tissue engineering is that the scaffolds degrade in vivo, thus allowing for remodeling of the tissue without the long-term presence of foreign material. Furthermore, this method does not suffer from the shrinkage of graft volume and does not suffer as severe complications as prosthetic implants, either. hASCs, which are also known as preadipocytes or adipose tissue-derived precursor cells, can be easily cultured using standard techniques, and indeed many groups have demonstrated successful isolation and culturing of human, rat and swine preadipocytes.

De novo adipose tissue engineering is generally undertaken with the help of tissue engineered constructs, which consist of three major components: cells, a biodegradable scaffold and a microenvironment suitable for cellular growth and differentiation. These constructs, when implanted into the test subject, initiate and direct the formation of de novo tissue. Over time, the scaffold degrades and the newly formed tissue takes its place.

However, stem cell-based approaches also have several disadvantages impeding their clinical translation—ranging from problems with scaling up of tissue culture to requiring complex GMP-certified laboratories for tissue culturing. Furthermore, it is challenging to efficiently vascularise large clinically relevant breast scaffolds using precursor cell induction techniques.

The overall goal of breast reconstruction is to restore the patient's breast mass with adipose tissue while maintaining tactile sensation.

The shape and size of the breast for each individual patient is different, hence the tissue construct used for adipose tissue engineering needs to be highly customized. Also, research has shown that the breast's architecture with regards to adipose tissue volume and skin elasticity and thickness changes over time. The tissue construct should adapt with such changes. Moreover, the scaffold used in the tissue construct should preferably be biodegradable and should not require surgical removal. It should also not invoke a strong inflammatory response or long-term fibrous encapsulation.

Similar options and problems as discussed above for the example of breast implants also exist for various other medical conditions where tissue replacement/reconstruction is a medical treatment choice, such as ligament reconstruction after anterior cruciate ligament tear, bone reconstruction for craniofacial reconstruction, maxillofacial reconstruction or complex jaw surgery, tissue reconstruction after removal of a melanoma or head and neck cancer, chest wall reconstruction, delayed burn reconstruction etc.

SUMMARY OF THE INVENTION

Thus, there is a need in the art for improved ways for the reconstruction of lost tissue and/or the restoration of tissue/organ function, in particular with respect to overcoming the above-described problems. Moreover, there is specifically a need for improved ways of breast reconstruction, in particular with respect to overcoming the above-described problems. Furthermore, there is a need in the art for ways to reconstruct tissue and/or restore tissue/organ function which allows for a better association of the transplanted cells or tissue with connective tissue and vasculature and/or results in reduced necrosis and resorption of the transplanted cells or tissue. Furthermore, there is a need in the art for ways to reconstruct tissue and/or restore tissue/organ function wherein the resulting structure better mimics the in vivo situation. Furthermore, there is a need in the art for ways to reconstruct tissue and/or restore tissue/organ function which allows for implantation of larger amounts of transplantation cells or tissue into a pre-prepared bed of connective tissue or vascularization. Furthermore, there is a need in the art for ways to reconstruct tissue and/or restore tissue/organ function which provides for shorter post-operative healing times and/or reduced aesthetic problems due to scar formation. Furthermore, there is a need in the art for ways to reconstruct tissue and/or restore tissue/organ function that are better suited for being carried out as a minimally invasive procedure.

These objects are solved by the below-described aspects of the present invention and the preferable embodiments described.

In a first aspect, the present invention relates to an implant comprising a three-dimensional scaffold structure, wherein said three-dimensional scaffold structure comprises voids, and wherein said voids are filled with space-occupying structures that are removably attached to said three-dimensional scaffold structure and that are configured to prevent invasion of tissue and/or of individual cells into said voids.

Preferably, said three-dimensional scaffold structure is made of biodegradable material.

An "implant" is a medical device manufactured to replace a missing biological structure, to support a damaged biological structure, and/or to enhance an existing biological structure. In particular, the implant of the present invention is an implant for the reconstruction of body tissue and/or the restoration of the function of a tissue or organ, preferably by tissue engineering. Examples for implants are a breast implant, e.g. for breast reconstruction after mastectomy or for breast augmentation, a salivary gland implant for the reconstruction of salivary gland functions, or a pancreas implant for the restoration of pancreatic island function (i.e. secretion of insulin and/or glucagon).

If the present application refers to an "implant comprising a three-dimensional scaffold structure", this is meant to designate that said implant includes, as one of the components that the implant is composed of, a three-dimensional scaffold structure. The implant may or may not comprise other components besides said three-dimensional scaffold structure.

Biodegradable materials suited for the preparation of said three-dimensional scaffold structure are, for example, polycaprolactone, poly(1,3-trimethylene carbonate), polylactide, polyglycolide, poly(ester amide), polyethylene glycol)/poly (butylene terephthalate), poly(glycerol sebacate), poly(1,8-octanediol-co-citric acid), poly(1,10-decanediol-co-D,L-lactic acid), poly(diol citrate), poly(glycolide-co-caprolactone), poly(1,3-trimethylene carbonate-co-lactide), poly(1,3-trimethylene carbonate-co-caprolactone) or a copolymer of at least two of these materials. Preferably, said biodegradable material is polycaprolactone, polyglycolide, polylactide, poly(1,3-trimethylene carbonate) or a copolymer of at least two of these materials. More preferably, said biodegradable material is either polycaprolactone or a copolymer of polycaprolactone and either poly-trimethylene carbonate or polylactide (on the grounds that the mechanical properties of copolymers formed out of these building blocks are similar to those of natural breast tissue). In one embodiment, said biodegradable material is a copolymer made of polycaprolactone, polylactide and polyglycolide.

Non-biodegradable materials suited for the preparation of said three-dimensional scaffold structure are, for example, silicone polymers, non-degradable polyurethanes and poly (ethylene terephthalate).

The three-dimensional scaffold structure comprised by said implant may for example have a bar-and-strut structure. Such a three-dimensional scaffold structure can e.g. be formed by fused deposition modeling (FDM, which is synonymous with fused filament fabrication (FFF)), by laser sintering or by stereolithography, with a suitable material, e.g. with polycaprolactone. To develop a customized three-dimensional scaffold structure, as desirable e.g. for a tailor-made breast implant, an integrated approach can be used which links medical imaging technology with Computer Aided Design and Computer Aided Manufacturing (CAD/CAM). As the skilled person will appreciate, there will be holes and/or pores within the three-dimensional scaffold structure, which upon implantation can be colonized by cells, such as connective tissue cells and/or blood vessels. Moreover, if said three-dimensional scaffold structure is made of a biodegradable material, the scaffold structure will be gradually degraded upon implantation, thus making additional space that can be invaded by connective tissue and/or blood vessels.

In addition to the holes and/or pores described previously, the three-dimensional scaffold structure described in the present invention contains voids (i.e. areas within the three-dimensional scaffold structure in which no scaffold is present) which may for example be formed by leaving areas blank during the preparation process (i.e. intentionally no scaffold is produced in these areas during manufacturing of the three-dimensional scaffold structure), or by removing a section of the three-dimensional scaffold structure after preparation of the three-dimensional scaffold structure, for example by excision. It will be appreciated by the skilled person that such voids may have any of various different shapes (such as straight or bent tubular shape; tunnels of different diameter and length; round, rectangular or square cross section etc.), and may be of different number, size and orientation within the three-dimensional scaffold structure.

In order to prevent invasion of tissue and/or of individual cells into said voids, the space-occupying structures can for example be in their entirety formed from a material of low porosity (such that there are no spaces within the space-occupying structures that the tissue and/or cells may invade), they can have a dense surface cover (such that cells and/or tissue are prevented from passing through) and/or they can have a surface coating that through a biological mechanism rejects tissue and/or cells from invasion (such as a coating with the drug tacrolimus, everolimus or mitomycin c, which locally prevents cell proliferation).

As the skilled person will appreciate, the space-occupying structures should substantially not be biodegradable within the time-frame for which the space-occupying structure will reside in a patient's body (typically, the time period from implantation of said implant into the patient's body until removal of the space-occupying structures will be in the range of 6-8 weeks).

A space-occupying structure is "removably attached" to the three-dimensional scaffold structure if it is present in the three-dimensional scaffold structure in such a manner that it is held in place during implantation of the implant, but after implantation of the implant (preferably 6-8 weeks after implantation of the implant) the space-occupying structure can be removed from the residual parts of the implant and the site of implantation while leaving the residual parts of the implant at the site of implantation. To achieve this, the linkages providing for physical attachment of the space-occupying structures to the three-dimensional scaffold structure may for example be formed from a material that can readily be severed with an appropriate tool during surgical removal of the space-occupying structures (for example, the linkages may be formed from polycaprolactone, which may readily be cut with a suitable surgical blade), the linkages providing for physical attachment of the space-occupying structures to the three-dimensional scaffold structure may be small in number and/or of only low mechanical strength such that, similar to a perforated paper, the linkages can readily be broken by mechanical force during surgical removal of the space-occupying structures, or the space-occupying structures may not be linked to the three-dimensional scaffold structure by physical linkages at all (instead, the space-occupying structures may then be held in place by complete or almost complete encasement by the three-dimensional scaffold structure). Moreover, the space-occupying structures may have a surface coating prepared from a drug (for example tacrolimus, everolimus or mitomycin c) that inhibits cell proliferation and thus delays cell invasion into the scaffold structure (or replacing the biodegradable scaffold structure) do not form linkages or form only weak linkages to the space-occupying structures.

As the skilled person will appreciate, since the implant is intended for use in the body of a patient all components of the implant should be made from biocompatible materials.

The implant according to the first aspect of the invention can be surgically implanted into a site of reconstruction. Upon surgical implantation into the body, connective tissue and/or vasculature will penetrate into the scaffold structure of the implant. Moreover, if the scaffold structure is made of a biodegradable material, the scaffold structure will gradually be degraded, and connective tissue and/or vasculature will also penetrate into the spaces where the biodegradable implant has already been degraded. Since the voids comprised within the implant are filled with space-occupying structures that are configured to prevent invasion of tissue and/or of individual cells into said voids, no connective tissue and/or cells will enter the space of the voids. After a time period ranging from several weeks to a few months from the time of surgical implantation of said implant, preferably 6-8 weeks after surgical implantation of said implant, the space-occupying structures are removed by a surgeon, for example by excision with a suitable surgical instrument and by removal of the released space-occupying structures from the implant/site of reconstruction with suitable surgical tongs, thus leaving behind void spaces at the region within the implant/site of reconstruction that was previously occupied by the space-occupying structures. The void spaces are then filled with the desired functional cells (the "transplantation cells", which may e.g. be fat tissue in the case of breast reconstruction, appropriate glandular epithelial cells in the case of a pancreatic islet implant, heart cells in implants for myocardial regeneration or mesenchymal stem cells in implants for cartilage reconstruction), for example by injection or infusion of the functional/transplantation cells. Thus, a pre-formed bed of connective tissue and vasculature allows the transplantation cells to remain stably within the implantation site, while only minimal tissue necrosis and resorption occur. Moreover, compared to methods in which the transplantation cells (in the case of breast reconstruction: fat tissue) are transferred to the site of reconstruction without previous formation of a bed of connective tissue and vasculature, the resulting structure much better mimics the in vivo situation (in the case of breast reconstruction: the internal architecture of the breast). Compared to implants without space-occupying structures, the implant according to the invention has the advantage that, while otherwise the major part of the space that exists within the implant or develops due to gradual degradation of a biodegradable scaffold will completely be taken over by connective tissue, in the present invention void spaces within the connective tissue and scaffold into which the transplantation cells may be introduced are created upon removal of the space-occupying structures.

The skilled person will appreciate that the voids have to be constructed such that they allow for introduction of the transplantation cells into said voids after the implant has been implanted into the body of a patient and the space-occupying structures have been removed.

In some embodiments, the voids are of tubular shape. Thus, in such embodiments the length of the voids is large in relation to the diameter of the voids. This has the advantage that the transplantation cells can easily be introduced deep into the implant and connective tissue that has invaded the implant (or replaced the implant upon degradation of the biodegradable implant), while at the same time the stability of the implant structure/connective tissue is not significantly compromised by excessively large voids.

Preferably, the diameter of the voids is at least 3 mm, more preferably at least 5 mm. Preferably, the length of the voids is at least 0.5 cm, more preferably at least 1 cm. Preferably, the diameter of the voids is not more than 10 cm, more preferably not more than 8 cm. Preferably, the length of the voids is not more than 12 cm, more preferably not more than 10 cm.

In some embodiments, said three-dimensional scaffold structure comprises at least three, more preferably at least five, more preferably at least eight voids, more preferably at least twelve, voids all of which are filled with space-occupying structures that are removably attached to said three-dimensional scaffold structure and that are configured to prevent invasion of tissue and/or of individual cells. As the skilled person will appreciate from the disclosure of the present application, several voids having a different angle and/or orientation may be interconnected. For example, the breast implant shown in FIG. 1A comprises a short, vertical void at the top of the implant and eight radially arranged, tubular voids that are connected to said short, vertical void. Thus, the breast implant shown in FIG. 1A comprises nine voids.

In some embodiments, said space-occupying structures have a smooth surface. As the skilled person will appreciate, a surface with a screw thread is not a smooth surface.

In some embodiments, said implant does not comprise screws. In some embodiments, said implant does not comprise rivets.

In some embodiments, said space-occupying structures are made of a different material than said three-dimensional scaffold structure. Preferably, said space-occupying structures are localized within the implant in a geometrically predefined orientation.

In some embodiments, said voids (and, preferably, also said space-occupying structures) are interconnected with each other and are arranged in a convergent geometric orientation radiating from one origin. A radiating arrangement of the voids can allow for removal of the space-occupying structures from the voids through a single site of access and has the advantage that through the single access tunnel all voids can be filled through a simplified procedure by a single injection of transplantation cells at the site where the radiating structure originates. Since the arrangement requires only a single site of tissue injury in order to get access to all the voids, it also reduces the tissue injury required for filling all voids with transplantation cells. This is particularly advantageous if it is intended to carry out the removal of the space-occupying structures and the introduction of transplantation cells by a minimally invasive procedure.

"Minimally invasive procedures" are surgical procedures that are carried out by entering the body through the skin or through a body cavity or anatomical opening, but with the smallest damage possible to these structures. Thus, in a minimally invasive procedure the collateral tissue damage is minimized. Consequently, the time for healing is reduced and the cosmetic outcome is improved due to the reduction of scars.

In some embodiments, said voids (and said space-occupying structures) are not interconnected and are arranged in a non-convergent geometric orientation. In some embodiments, said voids (and said space-occupying structures) are not interconnected and, preferably, are arranged in parallel. While this arrangement needs multiple access tunnels for introduction of the transplantation cells, it has the advantage that in this arrangement it is technically easier to remove the space-occupying structures, compared to convergent arrangements. Such an arrangement of outward-facing voids also enables easy injection of cells, tissue and/or lipoaspirate during surgery.

In some embodiments, said space-occupying structures are collapsible. Such a collapsible space-occupying structure may for example be a saline-filled tube made of a biocompatible polymeric material. The implant may be fabricated along with the collapsible space-occupying structures and is implanted at the site of desired reconstruction. After 6-8 weeks, the fluid within the space-occupying structures (such as the saline contained within a tube made of a biocompatible polymeric material) is removed by a minimally invasive procedure, for example by aspiration with a syringe. This causes the space-occupying structures to collapse. They then can be easily removed, leaving behind void spaces within the scaffold structure into which transplantation cells can be introduced.

Thus, compared to non-collapsible space-occupying structures, the use of collapsible space-occupying structures has the advantage that they can be removed more easily, with reduced tissue injury and all the advantages associated therewith (such as reduced post-operative pain, shorter healing time, less cosmetic problems due to scars etc.), for example by a minimally invasive procedure.

To prepare an implant with collapsible space-occupying structures, the implant along with inflated space-occupying structures will typically be assembled prior to implantation. Initially, only the implant containing empty spaces (voids) for the space-occupying structures is fabricated. In a second step, the initially deflated structures (i.e. the not yet filled sheaths of the space-occupying structures) are inserted into the predesigned empty spaces. The space-occupying structures can be filled and inflated by piercing the deflated structures with a syringe needle, filling the sheath and subsequently heat-sealing the sheath of the now filled structures. The completed assembly can finally be sterilized by gamma-irradiation or ethylene oxide and then be implanted into the patient. As the skilled person will appreciate, in case of a convergent design, the space-occupying structures can be connected, such that the surgeon can fill and extract fluid from all the structures by accessing only a single site of the interconnected space-occupying structures (typically the most superficial part).

Preferably, said space-occupying structures comprise or consist of a liquid encased in a sheath that is impermeable to said liquid. Preferably, said liquid is isotonic saline solution. Preferably, said sheath is made of a biocompatible polymer, more preferably of medical-grade polyurethane, nylon, polyether block amide or silicone.

By using sheath-encased liquid (or hydrogel) as space-occupying structures in combination with a convergent design of said space-occupying structures, it can be achieved that the saline solution (or hydrogel) could be aspirated from only one access point and the same access point can also be used to extract said collapsed space-occupying structures in a minimally invasive manner. The use of a sheath-encased liquid has, compared to sheath-encased hydrogel, the advantage that it is easier to remove the filling solution within the sheath completely without any remnants. Moreover, in case of a sheath-encased liquid the time of deflation can be freely chosen by a surgeon (in the case of a hydrogel it is dictated by degradation time), thus making it easier to choose a time span between implantation of the implant and removal of the space-occupying structure that is optimally suited for the specific kind of stromal cells used as transplantation cells. The use of saline solution as liquid has the advantage that it is not only inexpensive, but also completely poses no health risk if some liquid leaks into the body, for example during aspiration of the liquid in order to collapse the space-occupying structures.

Preferably, said space-occupying structures comprise or consist of a physiologically inert hydrogel encased in a sheath that is impermeable to said hydrogel. Preferably, said hydrogel comprises or consists of polyethylene glycol or polyvinyl alcohol. Preferably, said hydrogel comprises ferromagnetic particles mixed into the hydrogel. Preferably, said sheath is made of a biocompatible polymer, more preferably of medical-grade polyurethane, nylon, polyether block amide or silicone.

The use of a sheath-encased hydrogel as space-occupying structures provides the same advantages as sheath-encased liquids. However, compared to sheath-encased liquids, sheath-encased hydrogels provide a higher resistance to physiological stresses and, due to their higher viscosity compared to saline, are less prone to leakage into surrounding tissues.

Preferably, said space-occupying structures are fluidly connected with each other. If the present application indicates that a space-occupying structure A and a space-occupying structure B are "fluidly connected", this means that there is a connection between said space-occupying structures A and B that allows liquid or hydrogel from the lumen of space-occupying structure A to travel to the lumen of space-occupying structure B and vice versa without loss of liquid/hydrogel to the outside environment.

In some embodiments, said space-occupying structures are rigid. Rigid space-occupying structures have the advantage that they do not deform easily and that they retain their original shape even under high mechanical stress.

In some embodiments, said space-occupying structures are made exclusively of solids (i.e. do not comprise or consist of liquids or gels). The use of space-occupying structures that are made exclusively of solids has the advantage that no leakage of liquid or gel into the surrounding tissue can occur and that the space-occupying structures have a higher pressure resistance and form stability.

In some embodiments, said space-occupying structures are made of metal, preferably of steel or titanium. By using space-occupying structures made of metal, it can be achieved that no leakage of liquid or gel into the surrounding tissue can occur and that said space-occupying structures have very high pressure resistance and form stability. Moreover, if steel is used, the space-occupying structures can be easily removed in one motion by use of an electromagnetic removal device.

In some embodiments, said space-occupying structures comprise or consist of superparamagnetic or ferromagnetic material. Preferably, said space-occupying structures comprise or consist of a composite of a biocompatible polymeric material, preferably polycaprolactone, and of a biocompatible ferromagnetic material, preferably iron oxide.

Space-occupying structures comprising or consisting of superparamagnetic or ferromagnetic material allow for very efficient removal, for example by providing a small incision in the overlying skin and tissue and by removal of the space-occupying structures with a powerful (electro)magnet. This offers the further advantage that the space-occupying structures may be removed without having to insert a removal tool into the tissue and thus the risk of wound contamination is diminished.

In some embodiments, said space-occupying structures are coated with a coating that prevents tissue attachment. Preferably, said coating is a coating that comprises a cell proliferation inhibiting/reducing drug (an antiproliferative drug), more preferably a coating that comprises one or more of the drugs tacrolimus, everolimus and mitomycin c. Furthermore, the drug (e.g. the tacrolimus) can be suspended into a hydrogel prior to being coated onto the space-occupying structures. Such a hydrogel coating would prevent the drug from being degraded or diluted over an extended period of time.

Tacrolimus (FK-506) is an FDA (Food and Drug Administration of the U.S.)-approved drug which controls cellular proliferation and thus prevents fast ingrowth of host tissue. Hence, a coating with tacrolimus reduces the attachment and adherence of host tissue to the space-occupying structures. This, in turn, facilitates the removal of the space-occupying structures, reduces complications during the removal procedure like bleeding caused by tissue damage or rupture of blood vessels, and provides for improved conditions for the use of minimally invasive procedures.

In some embodiments, said implant is an implant for tissue engineering. In some embodiments, said implant is an implant for tissue reconstruction.

"Tissue reconstruction" refers to the repair or replacement of portions of tissues or whole tissues within the body or to the repair or replacement of portions of organs or whole organs. An implant for tissue reconstruction is an implant that is designed to aid the process of tissue reconstruction. It can for example take over the role of the supporting connective tissue within an organ or body part. In case of an implant comprising a three-dimensional scaffold structure made of a biodegradable material, the implant may temporarily take over the role of the supporting connective tissue. Once the implant is implanted into the body, body tissue, in particular connective tissue and vasculature, invades into the pores within the scaffold structure and, if the implant comprises a three-dimensional scaffold structure made of a biodegradable material, also into the areas where the scaffold structure has already been degraded. Thus, an implant for tissue engineering may provide a scaffold structure along which connective tissue and vasculature grows and which, if the three-dimensional scaffold structure of the implant is made of a biodegradable material, is gradually replaced by the body's own structures. Into this pre-formed bed of vascularized connective tissue, subsequently transplantation cells may be introduced.

In some embodiments, said implant is an implant for generating prevascularized connective tissue as recipient site for cell/tissue transplantation, preferably for transplantation of free fat grafts. Upon implantation of a suitable implant into the body at a desired recipient site for transplantation, tissue, in particular connective tissue, and vasculature invades the pores within the scaffold structure. (If the implant is an implant comprising a three-dimensional scaffold structure made of a biodegradable material, the scaffold is gradually degraded upon implantation, and tissue, in particular connective tissue, and vasculature also invade the areas where the implant has already been degraded.) Thus, the implant provides a scaffold structure which provides the structure along which the connective tissue and vasculature grows. Subsequently, the desired cells/tissue (such as a free fat graft) can be transplanted into the bed of connective tissue and blood vessels at the recipient site.

In some embodiments, said implant is a subcutaneous, osseous, cartilaginous or corresponding connective tissue implant.

In some embodiments, said implant is selected from the group consisting of a breast implant, an implant of the salivary gland, a pancreas implant, a bone implant, an implant to reconstruct an anterior cruciate ligament tear, a craniofacial reconstruction implant, a maxillofacial reconstruction implant, a complex jaw surgery implant, a post tumor-resection reconstruction implant, an implant for tissue reconstruction after removal of a melanoma, an implant for tissue reconstruction after removal of a head and neck cancer, an ear implant, a nose implant, a chest wall reconstruction implant, an orthopedic surgery implant, a cartilage reconstruction implant and a delayed burn reconstruction implant. Preferably, said implant is a breast implant.

In some embodiments, said implant is a breast implant for breast reconstruction and/or breast augmentation.

In some embodiments, said three-dimensional scaffold structure comprises a stack of multiple interconnected layers, each layer being composed of a plurality of bars, wherein
a) said bars have a zigzag structure or a wiggled structure; or
b) the bars of every n-th layer within said stack have a zigzag structure or a wiggled structure whereas, preferably, the bars of all other layers are straight bars,
wherein n is an integer in the range of from 2 to 5, preferably 2 or 3, more preferably 2; or
c) each layer comprises bars that have a zigzag structure or a wiggled structure, wherein, preferably, at least $1/10$, more preferably at least $1/5$, more preferably at least $1/3$, more preferably at least $1/2$ of the bars of each layer have a zigzag structure or a wiggled structure, whereas, preferably, all the other bars of said layer are straight bars; or
d) each n-th layer within said stack comprises bars that have a zigzag structure or a wiggled structure, wherein, preferably, at least $1/10$, more preferably at least $1/5$, more preferably at least $1/3$, more preferably at least $1/2$ of the bars of said n-th layer have a zigzag structure or a wiggled structure, whereas, preferably, all the other bars of said each n-th layer within said stack and the bars of all other layers are straight bars,
wherein n is an integer in the range of from 2 to 5, preferably 2 or 3, more preferably 2; or
e) $1/10$, preferably $1/5$, more preferably $1/3$, more preferably $1/2$ of the layers within said stack are layers that comprise bars having a zigzag structure or a wiggled structure, whereas, preferably, the other layers are layers that comprise only straight bars.

If the present application refers to a "stack of" multiple layers, this refers to an arrangement where multiple layers, the surface of which extends along an x- and y-axis, are piled on top of each other along a vertical z-axis. If the present application refers to a "stack of multiple interconnected layers", this means that the individual layers piled up to form the stack are physically linked to each other.

If the present application refers to a bar having a "zigzag structure", this indicates that the bar has a series of alterations in its course by short sharp turns or angles, wherein the sites at which these alterations in the course occur are angularly shaped. Preferably, such course alterations follow a regular pattern. Preferably, such alterations in the course prescribe 90° angles. Examples of bars having a zigzag structure are shown in FIG. 8.

If the present application refers to a bar having a "wiggled structure", this indicates that the bar has a series of alterations in its course by short sharp turns or angles, wherein the sites at which these alterations in the course occur have a rounded shape. Preferably, such course alterations follow a regular pattern. Examples of bars having a wiggled structure are shown in FIG. 8.

Preferably, each of said multiple interconnected layers is composed of a plurality of parallel bars.

Preferably, the layers within the stack are arranged such that the parallel bars of a certain layer X and the parallel bars of the subsequent layer X+1 form an angle of at least 30°, preferably of at least 45°, more preferably of at least 60°, more preferably of 90°.

As the skilled person will appreciate, when two non-parallel lines (and similarly, two non-parallel sets of parallel bars) cross, two angles are formed (which add up to 180°). When the present application states that the parallel bars of a certain layer and the parallel bars of the subsequent layer form a certain angle, the indicated angle refers to the smaller of the two angles formed. In the case of a bar/bars with zigzag structure or wiggled structure, the angle is measured with respect to the central axis of that bar (which essentially is a linear "best fit" curve for the zigzag course or wiggled course of the bar; see FIG. 8). Similarly, if, referring to bars with zigzag structure or wiggled structure, the present application indicates that such bars are "parallel", this means that the central axes of these bars with zigzag structure or wiggled structure are parallel with respect to each other.

Preferably, said bars with zigzag structure and/or said bars with wiggled structure are shaped such that the point in each turn within said bar that is most distant from the central axis of said bar (i.e. the outermost point of each turning point) has a distance from the central axis of said bar of at least 1/20, more preferably of at least 1/10, more preferably of at least 1/5, of the distance from the central axis of said bar to the central axis of the nearest parallel bar. Preferably, said bars with zigzag structure and/or said bars with wiggled structure are shaped such that the point in each turn within said bar that is most distant from the central axis of said bar has a distance from the central axis of said bar of at least 5 times, more preferably of at least 10 times, more preferably of at least 20 times, the diameter of said bar.

Preferably, said bars with zigzag structure and/or said bars with wiggled structure are shaped such that the distance between the outermost point of each turning point of said bar and the central axis of said bar equals at least twice the diameter of said bar. Preferably, said bars with zigzag structure and/or said bars with wiggled structure are shaped such that at least half of the volume of each bar with zigzag/wiggled structure is located outside of a virtual straight bar with the same diameter. Preferably, the angles and wiggles of said bars are configured with repetitive configurations.

In some embodiments, said implant has a scaffold structure with a layer structure as shown in FIG. 9B, FIG. 9C, or FIG. 9D of this application.

In some embodiments, said three-dimensional scaffold structure comprises a stack of multiple interconnected layers, each layer being composed of a plurality of parallel bars, wherein the layers within said stack are arranged such that the bars of any layer X within the stack have a perpendicular arrangement with respect to the bars of the subsequent layer X+1, such that the bars of any layer X within the stack and the bars of the layer following the layer subsequent to said layer X (i.e. layer X+2) are again parallel to each other, and wherein the bars of the layer following the layer subsequent to any layer Y (i.e. layer Y+2) are offset with respect to the bars of said layer Y by a distance of 1/m-times the distance between the parallel bars of said layer Y, wherein m is an integer in the range of from 2 to 5, preferably 2 or 3, more preferably 2.

As the skilled person will appreciate, in the three-dimensional scaffold structure as defined in the preceding paragraph, the bars of the (2*m)-th subsequent layer with respect to a layer Y will again be "in line" with the bars of layer Y (provided, of course, that the distance between the individual bars within the layer are the same for layer Y, layer Y+2, layer Y+4 etc.).

At several instances the present application indicates that the bars of a layer A are "offset with respect to the bars of" another layer B by a certain distance. This refers to a situation where, under circumstances where multiple layers are stacked along a vertical z-axis and where the bars of layer A are parallel to the bars of layer B, the bars of layer A are not placed directly above the bars of said layer B, but parallel-shifted within the plain of layer A by the indicated distance (i.e. geometrically the bars of layer A cannot be brought to congruency with the bars of layer B by translation along the z-axis, but in order to bring the bars of layer A to congruency with the bars of layer B translation along the x- and/or y-axis by a certain distance is required in addition to translation along the z-axis).

If the present application indicates that the bars of a certain layer A are "in line" with the bars of another layer B, this means that, under circumstances where multiple layers are stacked along a vertical z-axis and where the bars of layer A are parallel to the bars of layer B, geometrically the bars of layer A can be brought to congruency with the bars of layer B by translation along the z-axis.

Preferably, the bars of the layers within said stack are straight bars. Alternatively, the bars of the layers within said stack or the bars of every n-th layer within said stack may have a zigzag structure or wiggled structure, as described in the embodiments above, whereas, preferably, the bars of all other layers are straight bars.

In some embodiments, said three-dimensional scaffold structure comprises a stack of multiple interconnected layers, each layer being composed of a plurality of parallel bars, wherein the layers within said stack are arranged such that the parallel bars of any layer X within the stack and the parallel bars of the layer subsequent to said layer X (i.e. layer X+1) form an angle of (180/n)°, wherein n is an integer in the range of from 2 to 10, preferably 2, and wherein the bars of the n-th subsequent layer with respect to a certain layer Y within the stack (i.e. layer Y+n) are offset with respect to the bars of said layer Y by a distance of 1/m times the distance between the parallel bars of said layer Y, wherein in is an integer within the range of from 2 to 5, preferably 2 or 3, more preferably 2.

As the skilled person will appreciate, in the three-dimensional scaffold structure as defined in the preceding paragraph the bars of said layer X and the bars of the n-th layer subsequent to said layer X (i.e. layer X+n) will again be parallel with respect to each other (the offset will then of course be within the plane of the layer in a direction perpendicular to the direction in which the parallel bars of said layer are oriented). Moreover, in the three-dimensional scaffold structure as defined in the preceding paragraph, the bars of the (n*m)-th subsequent layer with respect to a layer Y will again be "in line" with the bars of layer Y (i.e. the bars of layer Y and of layer Y+(n*m) will be in line; provided, of course, that the distance between the individual bars within the layer are the same for layer Y, layer Y+n, layer Y+2n, layer Y+3n etc.).

Preferably, n is an integer in the range of from 2 to 6, more preferably 2 or 3, more preferably 2.

Preferably, the bars of the layers within said stack are straight bars. Alternatively, the bars of the layers within said stack or the bars of every n-th layer within said stack have a zigzag structure or wiggled structure, as described in the embodiments above, whereas, preferably, the bars of all other layers are straight bars.

In some embodiments, said implant has a scaffold structure as shown in FIG. 10 B below.

Implants with a conventional laydown pattern of FDM-manufactured three-dimensional tissue engineering scaffolds use continuous bars and struts. Such a laydown pattern restricts lateral compressibility. By using the laydown pattern as defined in the embodiments above (i.e. a three-dimensional scaffold structure with layers having bars with zigzag structure or wiggled structure and/or with layers the bars of which have an offset with respect to each other), highly improved control over scaffold mechanical properties, especially elasticity, stiffness, flexibility and compressibility, is achieved.

Whereas in conventional three-dimensional scaffold structures such properties can only be controlled by the use of elastomers as scaffold material, the three-dimensional scaffold structure according to the invention can be tailored with respect to its mechanical properties even if stiff or semi-stiff materials (such as polycaprolactone) are used as material for building the scaffold. Thus, a polycaprolactone scaffold can be adjusted to any specific tissue needs, from stiff bones over elastic cartilage to compressible connective tissue. As is evident from the data shown in FIG. 11 below, such modified scaffolds are more flexible, can take the same stress as the control scaffolds and display a higher range of elastic deformations as compared to control scaffolds with a conventional laydown pattern fabricated with the same parameters.

Moreover, in contrast to the conventional approach of simply using an elastomeric material for the three-dimensional scaffold structure, the approaches described above allow to accurately tailor the mechanical properties of the scaffold structure with regard to specific parts of the implant or specific angles of mechanical strain. For example, by choosing bars with zigzag structure or wiggled structure for the bars of a certain direction, the mechanical characteristics of the three-dimensional scaffold structure (such as flexibility and stress resistance) can be specifically designed for a specific angle, while in other angles the scaffold structure will have different mechanical characteristics. This is of particular importance for the compensation of potential structural weaknesses and imbalances caused by the presence of voids within the three-dimensional scaffold structure and also reduces the risk of damage to the implant itself within a moving environment. Moreover, it allows for an implant that can be used as replacement for a semi stiff structure like a tendon or joint.

In some embodiments, said three-dimensional scaffold structure is formed from a semi-stiff biomaterial, preferably from polycaprolactone. In some embodiments, said three-dimensional scaffold structure of said implant is not formed from an elastomeric biomaterial.

In some embodiments, said three-dimensional scaffold structure is formed from a shape-memory polymer (SMP). Preferably, said shape-memory polymer returns to its permanent shape if its temperature reaches or exceeds body temperature. Body temperature is 37° C. Alternatively, said shape-memory polymer returns to its permanent shape if its temperature reaches or exceeds 36° C. Preferably, said permanent shape is the shape the implant is desired to take after implantation.

As used herein, a "shape-memory polymer" is a polymeric material that can be deformed, but returns from the deformed state (temporary shape) to its original shape (permanent shape) upon reaching or surpassing a certain temperature (the "trigger temperature"). The shape memory polymers used in the present invention are materials that can be deformed at room temperature, but upon reaching or exceeding the trigger temperature (i.e. the body temperature of 37° C.; or, alternatively, 36° C.) change their shape into a desired shape.

Implants fabricated from a non-pliable material such as polycaprolactone may be difficult to use in surgical implantation, because insertion of such an implant requires a large incision. By using an SMP scaffold structure that returns to its original, permanent shape upon reaching body temperature (trigger temperature of 37° C.) and that has an original, permanent shape corresponding to the fully-formed shape that the implant is desired to take after implantation, implantation with a smaller incision becomes possible. The SMP scaffold structure of the implant is simply deformed at room temperature into a shape that requires a smaller incision (in case of a breast implant, for example, a disc-like shape) and implanted into the patient's body. Once implanted into the body, the temperature of the SMP scaffold structure will increase until it reaches body temperature. Upon reaching body temperature, which is the trigger temperature of the SMP material, the SMP scaffold returns to its original, permanent shape which is the shape that the implant is actually desired to have after implantation (in case of a breast implant the bent shape of a fully-formed breast implant which, if implanted in this extended shape, would have required a much larger incision). Thus, an implant with an SMP scaffold structure allows the surgeon to reduce the amount of tissue injury during implantation and thus permits the use of minimally invasive procedures.

In a second aspect, the present invention relates to a method of manufacturing an implant as defined in any of the embodiments above, said method comprising the steps of:
a) providing a three-dimensional scaffold structure, preferably a three-dimensional scaffold structure made of biodegradable material, said three-dimensional scaffold structure comprising voids;
b) providing space-occupying structures that are configured to prevent invasion of tissue and/or of individual cells into the space occupied by them;
c) inserting said space-occupying structures into said voids such that said space-occupying structures fill said voids, and removably attaching said space-occupying structures to said three-dimensional scaffold structure;

thus providing an implant.

Preferably, said implant, said three-dimensional scaffold structure, said biodegradable material, said voids, said space-occupying structures and said removable attachment are as defined in any of the embodiments above.

Preferably, said three-dimensional scaffold structure is formed by fused deposition modeling (fused filament fabrication), laser sintering or stereolithography. Preferably, said three-dimensional scaffold structure comprising voids is manufactured by producing a three-dimensional scaffold structure without voids and subsequently generating voids in said three-dimensional scaffold structure. Alternatively, said three-dimensional scaffold structure comprising voids is manufactured by a procedure in which during build-up of the three-dimensional scaffold structure no scaffold structure is produced at specific areas within the scaffold structure, such that upon completion of the build-up process a three-dimensional scaffold structure comprising voids is obtained.

In a third aspect, the present invention relates to a removal tool for removal of said space-occupying structures from an implant according to the invention, said removal tool comprising a blade for excision of a space-occupying structure, wherein said blade is shaped as a biopsy punch blade with the same shape and size as the cross-section of the space-occupying structure to be removed, said removal tool further comprising an appliance that allows to grasp the excised space-occupying structure.

The biopsy punch blade with the same shape and size as the cross-section of the space-occupying structure allows for easy and accurate cutting of any connections/linkages between the space-occupying structures and the scaffold structure of the implant and/or body tissue, simply by punching out the space-occupying structure in a close-fitting manner. The appliance that allows grasping the excised space-occupying structure may, for example, be a mechanical clamp. Alternatively, the blade shaped as a biopsy punch blade may lead into a hollow space with a tapered shape. Upon punching out the space-occupying structure, the space-occupying structure is led into the hollow space and gets jammed, such that it is removed upon retraction of the removal tool from the tissue.

In a fourth aspect, the present invention relates to a kit comprising an implant as defined in any of the embodiments above and a removal tool as defined in any of the embodiments above.

In a fifth aspect, the present invention relates to a removal device for the removal of ferromagnetic or superparamagnetic space-occupying structures from an implant according to the invention, wherein said removal device comprises at least one magnet, preferably at least one electromagnet.

Such a device may be used for the removal of superparamagnetic or ferromagnetic space-occupying structures according to the following procedure: An implant according to the invention, comprising superparamagnetic or ferromagnetic space-occupying structures, is implanted at a desired site into a patient's body. Once the space-occupying structures are to be removed again in order to create void spaces for the introduction of transplantation cells, small incisions are provided to the overlying skin, body tissue and, if still present, the (biodegradable) scaffold structure at the specific positions where the space-occupying structures reside, thus making way for removal of the space-occupying structures. Then the removal device is lowered in the appropriate orientation onto the area, bringing the at least one (electro)magnet into close proximity, preferably into direct contact, with the space-occupying structures. If the at least one magnet is an electromagnet, it is turned on at this point. The strong magnetic forces exerted by the at least one (electro)magnet attract the superparamagnetic or ferromagnetic space-occupying structures, such that they get attached to the at least one (electro)magnet. Upon withdrawal of the removal device from the body of the patient, the space-occupying structures move along with the removal device and are extracted from their original position and removed from the patient's body.

As the skilled person will appreciate, for optimal performance the positions of the at least one (electro)magnet within the removal device and the position of the space-occupying structures within the implant have to correspond, thus ensuring that the at least one (electro)magnet is in ideal position for exerting magnetic forces on the space-occupying structures.

Preferably, said removal device is a removal device for the removal of superparamagnetic or ferromagnetic space-occupying structures from a breast implant.

Preferably, said removal device is shaped such that it fits the contours of said implant. For example, if the implant is a breast implant, the removal device will have the hemispherical shape of a breast implant. This ensures a good fit of the removal device to the implant and thus makes sure that the distance between the at least one (electro)magnet of the removal device and the superparamagnetic or ferromagnetic space-occupying structures within the implant is minimized, preferably direct contact between the at least one (electro)magnet of the removal device and the superparamagnetic or ferromagnetic space-occupying structures within the implant is achieved, in order to maximize the magnetic forces exerted.

In a sixth aspect, the present invention relates to a guiding device for providing feedback to a surgeon during the procedure of introducing transplantation cells into the void spaces generated upon removal of said space-occupying structures from an implant according to any of the embodiments described above, wherein said guiding device fits the contours of the implant, wherein said guiding device comprises markings and/or guiding holes which are spatially and angularly aligned to the void spaces generated upon removal of the space-occupying structures.

In some embodiments, the areas of the guiding device directly next to each of the markings or the guiding holes are engraved or embossed with information detailing the approximate depth of the underlying void that prevents the syringe from going too deeply while ensuring that the transplantation cells and/or tissue is deposited as deep as possible within the implant.

If the present application states that a guiding hole of a guiding device is "spatially and angularly aligned" to a void space generated upon removal of a space-occupying structure, this means that the guiding hole has such a location and orientation within the guiding device that, if the guiding device is brought into an appropriate position and orientation on the implantation site, the guiding hole is aligned with said void space such that it spatially forms an extension of said void space (i.e. the guiding hole and the void space form a continuous tunnel). Such a configuration of the guiding hole ensures that the void space can be reached with a hollow needle inserted through the guiding hole.

Preferably, said guiding device comprises an appliance for appropriate positioning of the guiding device (i.e. an element that allows for a positioning of the guiding device at the site of implantation such that the guiding holes in the guiding device and the void spaces in the implant are aligned). Said element can for example comprise or consist of one or more three-dimensional extensions that match corresponding indentations in the implant, thus providing for guidance to ensure unambiguous appropriate placement and orientation of the guiding device at the implantation site.

Preferably, said guiding holes reach completely through said guiding device.

In some embodiments, said guiding device is cone-shaped. Preferably, said guiding holes extend through said cone-shaped guiding device from the tip to the base of the cone. Preferably, said guiding holes have a position and orientation within said guiding device such that, with appropriate positioning of said guiding device, said guiding holes are aligned with the void spaces generated upon removal of said space-occupying structures from said implant such that each guiding hole spatially forms an extension of a void space (such that the guiding hole and the void space form a continuous tunnel). Such a configuration of the guiding device and the guiding holes ensures that each void space within the implant can be reached with a hollow needle inserted through the opening at the tip of the cone-shaped guiding device. The guiding holes may be straight or curved. A flexible plastic cannula may be used for injection of transplantation cells through a curved guiding hole.

Preferably said guiding device provides feedback about the direction and/or depth of the void spaces and/or the number of injections (or fat depositions) needed.

To use the guiding device during the procedure of introducing transplantation cells into the void spaces generated upon removal of said space-occupying structures from an implant, upon removal of the space-occupying structures from the implant the guiding device is placed on top of the site where the implant was implanted (i.e. on top of the skin overlying the implant with void spaces). The guiding device may be cone-shaped, with guiding holes extending through the guiding device from the tip to the base of the cone-shaped guiding device, the guiding holes having an angular alignment such that, with appropriate positioning of the guiding device, each guiding hole spatially forms an extension of a void space within the implant. Appropriate positioning of the guiding device can be ensured by a plugging mechanism, i.e. the guiding device can for example comprise one or more extensions extending from the base of the cone-shaped guiding device, the implant has corresponding cavities and either by the shape of the extensions/cavities (e.g. the shape of a non-equal sided triangle) or by the orientation of the different extensions/cavities with respect to each other it is ensured that insertion of the extensions into the cavities allows for exact and unambiguous placement and orientation of the guiding device. The transplantation cells can for example be introduced into the void spaces within the implant by means of a syringe connected to a hollow needle at its tip or a flexible plastic cannula. The hollow needle is inserted through the opening at the tip of the cone-shaped guiding device. While the hollow needle itself is thin enough to enter into the guiding holes, the syringe is too thick and thus is prevented from entering into the guiding holes. Due to their specific angular orientation, the guiding holes make sure that the surgeon knows about the optimal angle for inserting the hollow needle into the void space. Moreover, by using a hollow needle with a length that is just below the combined length of the respective guiding hole plus the length of the void space aligned therewith, it can be made sure that, upon insertion of the hollow needle through the guiding hole into the void space, the hollow needle reaches close to the bottom of the void space without touching it. Thus, the guiding device provides feedback to the surgeon about in which orientation and how deep the hollow needle has to be inserted for the introduction of transplantation cells into the void spaces.

In a seventh aspect, the present invention relates to a method for tissue reconstruction in the body of a patient, comprising the following steps in order:
a) implanting an implant comprising a three-dimensional scaffold structure made of biodegradable material into said body of said patient at the site of intended tissue reconstruction;
b) after a time period sufficient to allow connective tissue and/or host vasculature to penetrate into said three-dimensional scaffold structure and/or invade the space that was occupied by said three-dimensional scaffold structure at the time of implantation, preferably after 6-8 weeks, introducing transplantation cells to the site of intended tissue reconstruction.

Preferably, said three-dimensional scaffold structure of said implant implanted in step a) does not comprise voids.

Preferably, said patient, said implant, said scaffold structure, said biodegradable material, said transplantation cells and said voids are as defined in any of the embodiments above or below.

In an eighth aspect, the present invention relates to a method for tissue reconstruction in the body of a patient, comprising the following steps in order:
a) implanting into said body of said patient at the site of intended tissue reconstruction an implant comprising a three-dimensional scaffold structure, preferably a three-dimensional scaffold structure made of biodegradable material, wherein said three-dimensional scaffold structure comprises voids, and wherein said voids are filled with space-occupying structures that are removably attached to said three-dimensional scaffold structure and that are configured to prevent invasion of tissue and/or of individual cells into said voids;
b) after an incubation time period sufficient to allow for connective tissue and/or host vasculature to penetrate into the scaffold structure and/or, if the three-dimensional scaffold structure is made of biodegradable material, to invade the space that was occupied by the biodegradable scaffold structure at the time of implantation, removing the space-occupying structures from said voids within the (biodegradable) scaffold structure (or from the tissue that has replaced the biodegradable scaffold structure during the incubation time period), thus generating void spaces not filled with space-occupying structures;
c) introducing transplantation cells into the void spaces not filled with space-occupying structures generated in step b).

Preferably, said implant, said three-dimensional scaffold structure, said biodegradable material, said voids, said space-occupying structures and said removable attachment are as defined in any of the embodiments above.

Preferably, said incubation time period is in the range of 4-12 weeks, more preferably in the range of 6-8 weeks.

Preferably, said patient is a patient in need of tissue reconstruction.

In some embodiments, said patient is a mammal, preferably a human.

In some embodiments, said transplantation cells are mammalian cells, preferably human cells. As the skilled person will appreciate, to avoid immune reactions against the injected cells, the injected cells should preferably be of the same species as the patient and, preferably, be genetically sufficiently close to the cells of the patient to avoid (strong) rejection reactions by the patient's immune system.

The term "transplantation cells", as used herein, refers to cells of a desired cell type (or a combination of cells of several different desired cell types) that are introduced for tissue reconstruction at the site where tissue reconstruction is desired. As described above, in the context of the present invention transplantation cells will typically be delivered to the site of tissue reconstruction by introducing them into the void spaces created upon removal of the space-occupying structures. Transplantation cells may be stem cells (multi- or unipontent), progenitor cells (also called precursor cells) or (fully) differentiated cells. The term includes individual cells (i.e. cells that are not physically linked to each other) and groups of cells that are physically linked to each other (such as cells arranged in a tissue). In some embodiments, the term only refers to individual cells and does not refer to groups of cells that are physically linked to each other. In some embodiments, the term only refers to groups of cells that are physically linked to each other and does not refer to individual cells. Transplantation cells may either be cells that are transplanted from a different site within the body of the same individual or cells that are transplanted from the body of a different individual than the patient, or they may be cells produced outside of a living organism, for example in a cell/tissue culture system.

In some embodiments, the transplantation cells are differentiated cells. As used herein, the term "differentiated cell" refers to a cell having a specialized function and form (e.g., fat cells, muscle cells etc.). Differentiated cells have no stem cell potential and thus lack potential of self-renewal and further differentiation. Examples of differentiated cells include epidermic cells, pancreatic parenchymal cells, pancreatic duct cells, hepatic cells, blood cells, cardiac muscle cells, skeletal muscle cells, osteocytes, myocytes, neurons, vascular endothelial cells, pigment cells, smooth muscle cells, adipocytes, bone cells, chondrocytes, and the like.

In some embodiments, the transplantation cells are cardiomyocytes, cells derived from pancreas, or chondrocytes.

In some embodiments, the transplantation cells are a mixture of cells obtained by lipoaspiration. A mixture of cells obtained by lipoaspiration can be prepared and introduced into the reconstruction site as follows: A very small incision is made at the site where the fat is to be obtained, and fat is aspirated using a blunt needle with multiple perforations and a special aspirator. This fat is filtered to separate blood, oil and local anesthetic from the fat cells. The site where the cells are to be introduced is injected with a minimal amount of local anesthetic(s), after which the fat cells are injected with very fine canulas. Only a very small amount of fat is injected with each pass of the canula. This way the grafted fat will be in direct apposition with the surrounding tissues and thus in minimal distance to nutritive blood vessels. By this means survival of fat grafts is maximized.

In some embodiments, the transplantation cells are precursor cells. A "precursor cell", as used herein, refers to an undifferentiated or partially differentiated cell having the capacity of undergoing further differentiation into a certain cell type or to acquire the capacity to perform a specific function. Thus, the term refers to monopotent undifferentiated or partially differentiated cells that are precursors for a specific cell lineage. Examples of precursor cells are thymocytes, megakaryoblast, promegakaryocytes, lymphoblast, bone marrow precursor cells, normoblast, angioblasts (endothelial precursor cells), osteoblasts, skeletal myoblasts, myeloid progenitor cells, satellite cells found in muscles, and transit amplifying neural progenitors.

In some embodiments, the transplantation cells are adipose tissue-derived precursor cells (APCs), bone marrow-derived precursor cells, periosteum-derived progenitor cells and Umbilical-cord-derived precursor cells.

In some embodiments, said implant is an implant for tissue reconstruction, and the transplantation cells are cells of the tissue to be reconstructed or precursor cells of cells of the tissue to be reconstructed.

The transplantation cells used in the present invention may be of autologous origin with respect to said patient (self-origin) or of heterologous origin with respect to said patient (non-self origin). In view of potential immune rejection reactions, cells of autologous origin are preferable. If rejection reactions do not cause problems, cells of heterologous origin may be employed.

The transplantation cells may be syngeneic (genetically identical) or allogeneic (genetically different). In view of potential immune rejection reactions, syngeneic cells are preferable. If rejection reactions do not cause problems, allogeneic cells may be employed, preferably allogeneic cells that are genetically still sufficiently identical and immunologically compatible as to allow for transplantation (i.e. no strong immunological rejection reaction occurs).

In some embodiments, said transplantation cells are selected such that they are not rejected by the immune system of said patient. In some embodiments, said transplantation cells are autologous cells with respect to said patient. In some embodiments, said transplantation cells are cells of said patient or derived from said patient. In some embodiments, said transplantation cells are syngeneic with respect to said patient.

In some embodiments, said transplantation cells are heterologous cells with respect to said patient. In some embodiments, said transplantation cells are allogeneic with respect to said patient.

In a ninth aspect, the present invention relates to a method of removing space-occupying structures from the body of a patient, wherein said space-occupying structures were introduced into the body of said patient as space-occupying structures that were part of an implant as defined in any of the embodiments above, and wherein said method involves removal of the space-occupying structures with a removal tool as defined in any of the embodiments above.

In a tenth aspect, the present invention relates to a method of removing ferromagnetic or superparamagnetic space-occupying structures from the body of a patient, wherein said ferromagnetic or superparamagnetic space-occupying structures were introduced into the body of said patient as space-occupying structures that were part of an implant as defined in any of the embodiments above, and wherein said method involves removal of the space-occupying structures with a removal device as defined in any of the embodiments above.

BRIEF DESCRIPTION OF THE FIGURES

The invention is now described with reference to the attached figures, wherein:

FIG. 3 Exemplary depiction of the preparation and use of an implant according to the invention, in this case a breast implant with interconnected voids in a convergent arrangement, filled with collapsible space-occupying structures. (A, B) The space-occupying structures are filled with a liquid or hydrogel (A: initial state; B: final state). (C) The implant has been implanted into the body of the patient at the site of desired breast reconstruction. (D, E) Removal of liquid or hydrogel from the collapsible space-occupying structures by means of aspiration with a syringe (D: initial state; E: final state), which causes the space-occupying structures to collapse and facilitates their subsequent removal. (F, G) Injection of transplantation cells (in this case fat isolated from a donor site within the patient) into the void spaces not filled by space-occupying structures (F: initial state; G: final state).

FIG. 4 shows the principle of an implant made from a shape-memory polymer by the example of a scaffold of a breast implant. (A) Fully-formed breast implant scaffold made from a shape-memory polymer (the fully-formed shape is the original, permanent shape which the implant will return to upon reaching the "trigger temperature" of 37° C.). (B) Side view of the deformed, disc-like shape of the breast implant scaffold made from an SMP material at room temperature.

FIG. 6 shows an embodiment of a removal device for the removal of ferromagnetic or superparamagnetic space-occupying structures from an implant according to the invention in an angular side view (A) and an angular bottom view (B).

FIG. 9 shows different laydown patterns for three-dimensional scaffolds of implants according to the invention.

FIG. 10 shows schematic side views of three-dimensional scaffolds with a conventional laydown pattern without offset (A) and with an exemplary laydown pattern according to the invention in which every other layer is offset by a certain distance (B).

FIG. 11 shows stress versus strain curves of (A) a conventional three-dimensional scaffold with straight bars, (B) a three-dimensional scaffold according to the invention having bars with a wiggled structure, (C) a conventional three-dimensional scaffold without offset and (D) a three-dimensional scaffold according to the invention having an offset.

FIG. 14 shows explantation images taken from Example 1 described below, showing the integration of TECs (tissue engineered constructs) with the host tissue. The arrow in panel A points out a major blood vessel supplying blood to the TEC. (D, G) show empty scaffold-only group, (E, H) show lipoaspirate-only group, (F, I) show prevascularisation+lipoaspirate group. All scaffolds show good integration with the host tissues and large areas of fat (marked with +) and vascularisation (marked with ¶) were observed qualitatively on all scaffolds.

FIG. 15 (LEFT) shows representative images showing H&E staining of tissue explanted from the empty scaffold group (superficial layers) of Example 1. A majority of the tissue can be identified as being connective tissue and collagen with only very small patches of fat tissue. FIG. 15 (RIGHT) shows representative images showing H&E staining of tissue explanted from the empty scaffold group (deep layers) of Example 1. Adipose tissue is only seen at the edges of the construct and not in the central regions of the scaffold. Lymphatic structures (right panel, marked by arrows) were also observed in all groups mainly localised near scaffold strands.

FIG. 16 (LEFT) shows H&E stained sections of the lipoaspirate-only group (superficial layers) of Example 1. Overall, a higher percentage of fat tissue compared to overall tissue area, compared to empty scaffold group, was observed in this group. FIG. 16 (RIGHT) shows H&E stained sections of the lipoaspirate-only group (deep layers) of Example 1. Deeper layers of the scaffold showed lower relative adipose tissue areas and lower degrees of vascularisation.

FIG. 17 (LEFT) shows H&E stained sections of the prevascularisation+lipoaspirate group (superficial layers) of Example 1. This group showed the highest accumulation of adipose tissue interspersed between connective tissue. Tissue morphology also showed similarities with native tissue. FIG. 17 (RIGHT) shows H&E stained sections of the prevascularisation+lipoaspirate group (deep layers) of Example 1. Adipose tissue area was the highest among all other groups. Adipose tissue regions seemed to be better connected to each other and formed interconnected structures.

Figure 1:
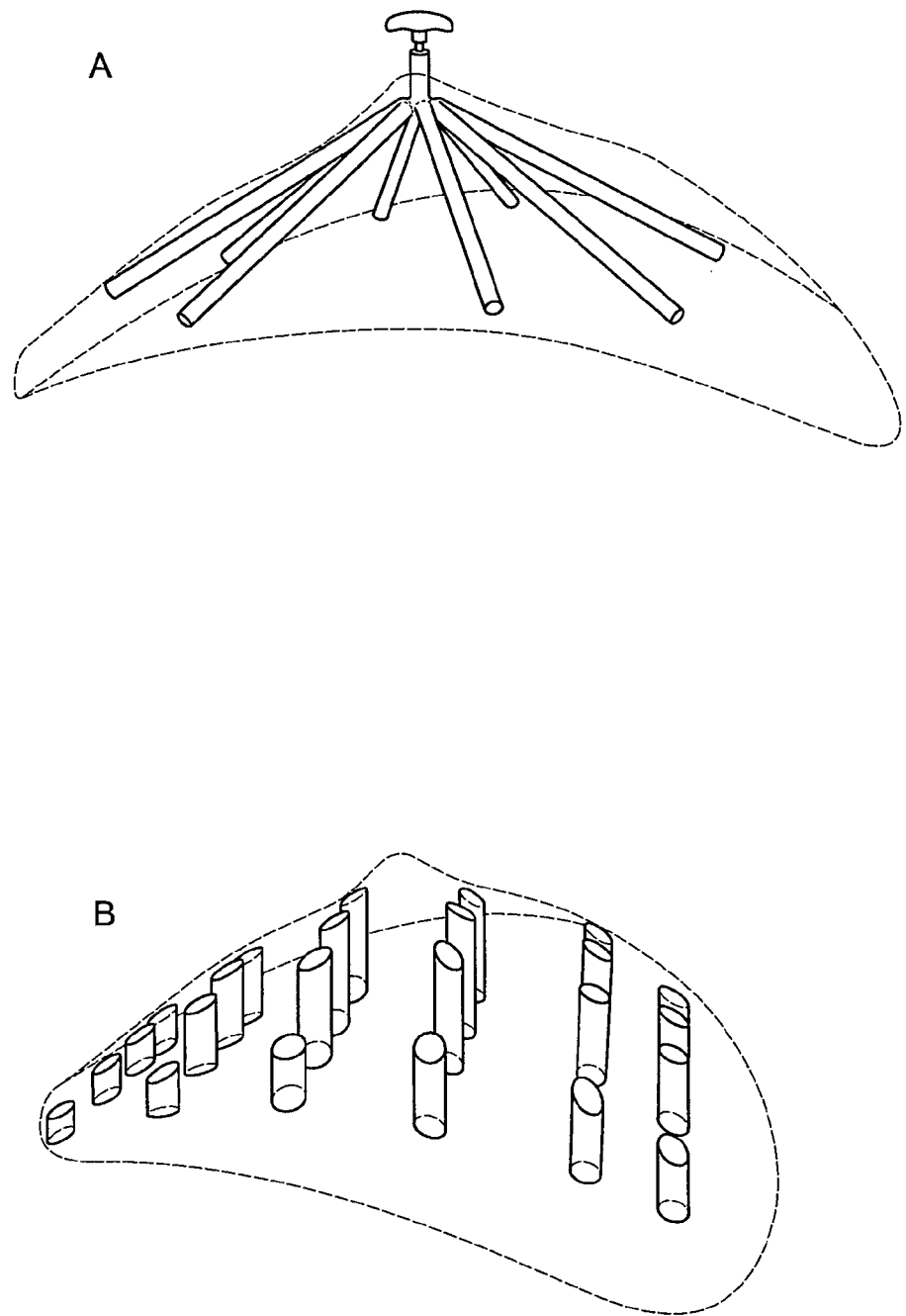
FIG. 1 shows two exemplary embodiments of the present invention wherein the implant according to the invention is a breast implant. (A) Example of a breast implant according to the invention wherein the voids are interconnected with each other and arranged in a convergent geometric orientation radiating from one origin. (B) Example of a breast implant according to the invention wherein the voids are not interconnected and arranged in a non-convergent (in this case parallel) geometric orientation.

In Masson's Trichrome staining, green colour indicates collagen fibres, red colour indicates muscle fibres and dark brown shows cell nuclei. (A, D) show the empty scaffold group (B, E) show the prevascularisation+lipoaspirate group (C, F) show the lipoaspirate-only group. Besides the adipose tissue, a majority of the tissue filling the pores of the implant consisted of connective tissue. Smooth muscle tissue was also detected lining the strands of the scaffold. These smooth muscle layers had the highest thickness in case of the prevascularisation+lipoaspirate group. (G) Column plot showing the adipose tissue area relative to total tissue area over 24 weeks. Negative control scaffold-only group had the lowest relative area of adipose tissue (8.31%±8.94) which was significantly lower than both the lipoaspirate-only (39.67%±2.04) and the prevascularisation+lipoaspirate group (47.32%±4.12) and also compared to native breast tissue (44.97%±14.12) ($p<0.05$, $p<0.01$ and $p<0.01$ respectively). No statistically significant difference in relative adipose tissue area was observed between the native breast tissue, lipoaspirate-only and prevascularisation+lipoaspirate groups. (H) Graph showing blood vessel density in the tissue sections from different groups. Highest blood vessel density was observed in the prevascularisation+lipoaspirate group ($38.01/mm^2$±2.02), however the density was not statistically significantly higher than the scaffold-only ($33.13/mm^2$±12.03), lipoaspirate-only ($26.67/mm^2$±1.6) or control breast tissue ($35.45/mm^2$±1.93). (I) Histogram showing the distribution of adipose cells according to the cell surface area. In all groups, the histograms were skewed to the right suggesting that a majority of adipose cell surface areas lay in the range of 100-700 $\mu m^2$. The distribution of the cell sizes in control breast tissue was considerably different compared to the other groups—with the highest percentage of cells in the 100-200, 300-400 and 500-600 $\mu m^2$ range. The empty scaffold and lipoaspirate-only groups had a low number of adipose cells whose surface areas were larger than 800 $\mu m^2$; however, the prevascularisation+lipoaspirate group showed a more equalised distribution with a significantly large number of cells having a surface area larger than 1000 $\mu m^2$. (J) Clustered column graph showing tissue composition at week 24 in various groups. TECs from the empty scaffold group contained an estimated 4.99 $cm^3$ (±2.71) of adipose tissue, TECs from the lipoaspirate-only group contained an estimated 23.85 $cm^3$ (±1.22) of adipose tissue, whereas TECs from the prevascularisation+lipoaspirate group contained an estimated 28.391 $cm^3$ (±2.48) of adipose tissue. (K) Column graph showing estimated fold increase in adipose tissue volume compared to initial injected lipoaspirate volume (4 $cm^3$) in the lipoaspirate-only and prevascularisation+lipoaspirate groups. The prevascularisation+lipoaspirate group had a higher fold increase in adipose tissue volume (6.1±0.62) compared to lipoaspirate-only group (4.95±0.31); however, the difference was not statistically significant (p=0.143).

Figure 20:
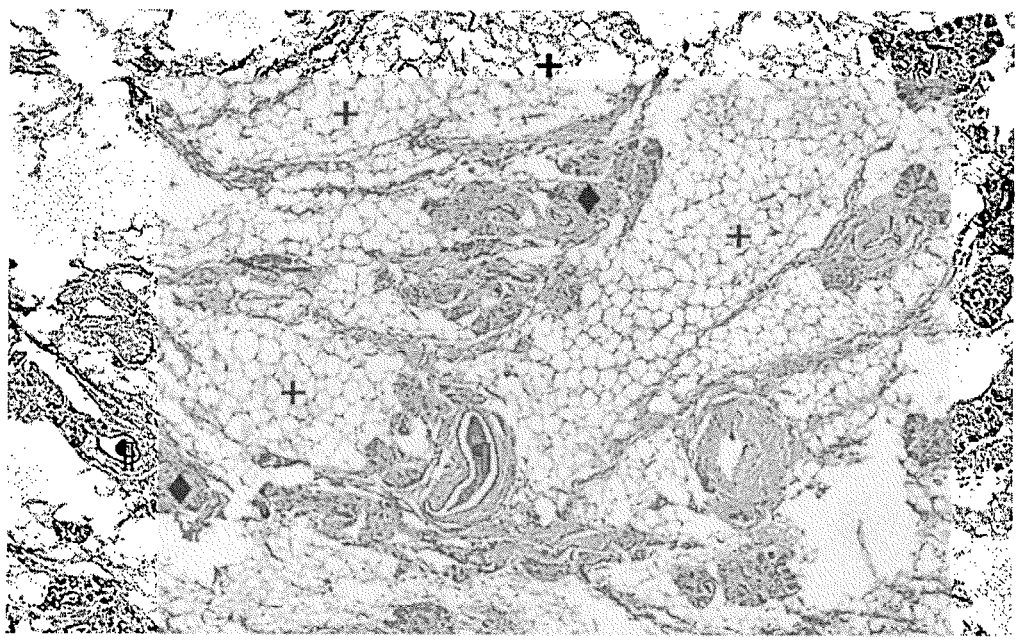

FIG. 20 shows H & E stained sections of untreated control breast tissue (healthy breast tissue, no scaffold implantation or application of lipoaspirate).

FIG. 21 shows a fabricated breast shaped scaffold containing voids and space-occupying structures and the removal of the space occupying structures. (A) Fabricated breast shaped scaffold made out of biodegradable poly-lactic acid (white material in FIG. 21) containing solid regions of low porosity made of poly-lactic acid with a black dye (i.e. space-occupying structures, seen as black dots in FIG. 21 A). The space-occupying structures had basically 0% porosity and were loosely attached with the main body of the scaffold (0.4 mm gap between the main body and the space occupying structures). (B) A cutting tool is used to punch out the regions of low porosity and mechanical integrity (i.e. to remove the space-occupying structures from the scaffold). While for illustrative purposes FIG. 21 B shows the removal procedure with a scaffold outside of the body of a patient, the same procedure of punching out the space-occupying structures is also used for a scaffold that has been implanted into the body. (C) The void space left behind by removal of the low porosity regions (highlighted with circle) can be used for lipofilling.

Figure 22:
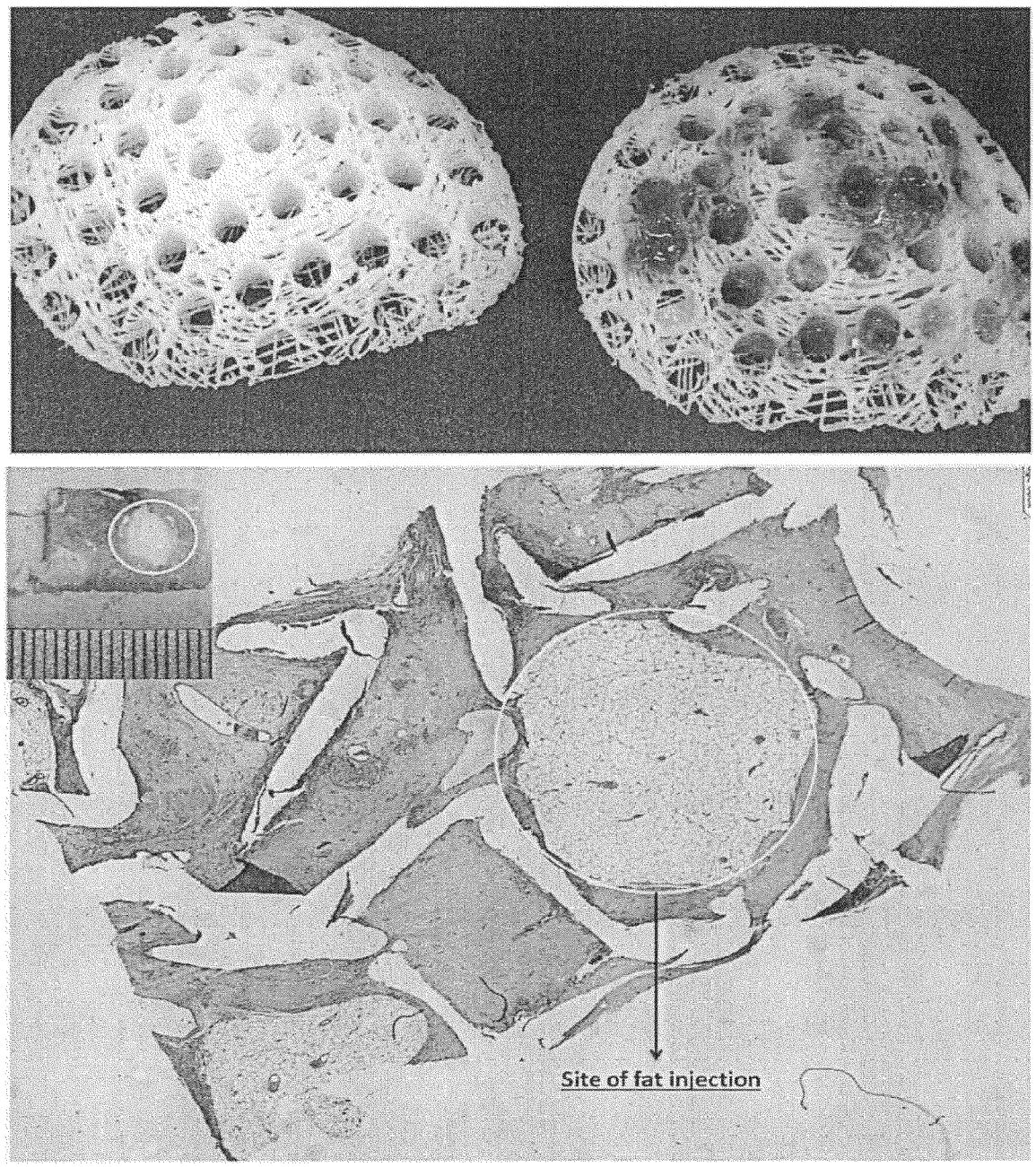

FIG. 22 shows (TOP) photographic images of scaffolds containing void spaces (no implantation) (left) and with adipose tissue injected into the void spaces (right). (BOTTOM) Hematoxylin and Eosin stained section of a scaffold explanted after 6 months implantation into minipigs. Inset on top left shows a cut out of the area surrounding a randomly selected void filled with adipose tissue (adipose tissue encircled). The corresponding area in the histological section, also encircled, shows healthy well vascularised adipose tissue at the injection site with no signs of necrosis.

DETAILED DESCRIPTION OF PREFERRED EMBODIMENTS

For the purpose of promoting an understanding of the principles of the invention, reference will now be made to the preferred embodiments and specific language will be used to describe the same. It will nevertheless be understood that no limitation of the scope of the invention is intended thereby, such alterations and further modifications in the device and methods and such further applications of the principles of the invention as illustrated therein being contemplated as would normally occur now or in the future to one skilled in the art to which the invention relates.

Moreover, it is to be understood that features and advantages described with regard to one aspect of the invention may also be implied by other aspects of the invention.

FIG. 1 shows two exemplary embodiments of implants according to the present invention. Both embodiments represented are breast implants the overall shape of which is formed from a three-dimensional scaffold structure made from biodegradable or non-biodegradable material. As seen in FIG. 1, in both embodiments the three-dimensional scaffold structure comprises voids that are filled with space-occupying structures.

In the embodiment of FIG. 1A, the voids are interconnected with each other and arranged in a convergent geometric orientation radiating from one origin. Entry through the origin of the void structure (from the top of the implant as depicted) allows access to all voids of the void structure, for example to introduce transplantation cells after removal of the space-occupying structures. Moreover, this arrangement may also allow to fill a collapsible space-occupying structure with liquid or hydrogel during preparation of an implant with collapsible space-occupying structures through a single access point, to aspirate the liquid or hydrogel from collapsible space-occupying structures through a single access point or to remove the space-occupying structures through a single incision wound at the point of origin. Thus, in several aspects this arrangement allows to simplify the steps carried out for use of the implant and to minimize the injuries inflicted to the patient during surgical procedures.

The specific embodiment of FIG. 1A further includes a "handle" (depicted at the top of the implant) that the surgeon can use to remove the entire space-occupying structure assembly after he/she has aspirated the liquid or hydrogel and the space-occupying structures have collapsed. The handle helps the surgeon to lift the collapsed assembly out of the scaffold and the patient's body. Other shapes of the handle than the conceptualised shape shown in FIG. 1A are contemplated as well.

In the embodiment of FIG. 1B, the voids within the implant are not interconnected, but arranged in parallel along one axis of the scaffold (i.e. arranged in a non-convergent geometric orientation). While such an arrangement requires multiple access tunnels for removal of the space-occupying structures or the introduction of transplantation cells, it makes removal of the space-occupying structures technically easier, because each space-occupying structure can be accessed directly and lies directly beneath the skin surface.

It is to be understood that the arrangements of the voids as shown in the embodiments depicted in FIG. 1 are merely of exemplary nature, and diverse other arrangements of the voids (convergent, non-convergent or combinations thereof) also lie within the scope of the present invention. Moreover, as the skilled person will appreciate, the breast implants shown in FIG. 1 (and some of the other Figures) are only examples, and the present invention also relates to implants for reconstruction of other parts or tissues of the body, such as reconstruction after anterior cruciate ligament tear, craniofacial reconstruction, maxillofacial reconstruction, complex jaw surgery, tissue reconstruction after removal of melanoma or head and neck cancer, chest wall reconstruction, delayed burn reconstruction etc. Naturally, such implants will differ in their structure, shape and characteristics from the breast implants depicted and will, while still constructed and used according to the principles of the present invention, be specifically adapted to the required purposes.

Figure 2:
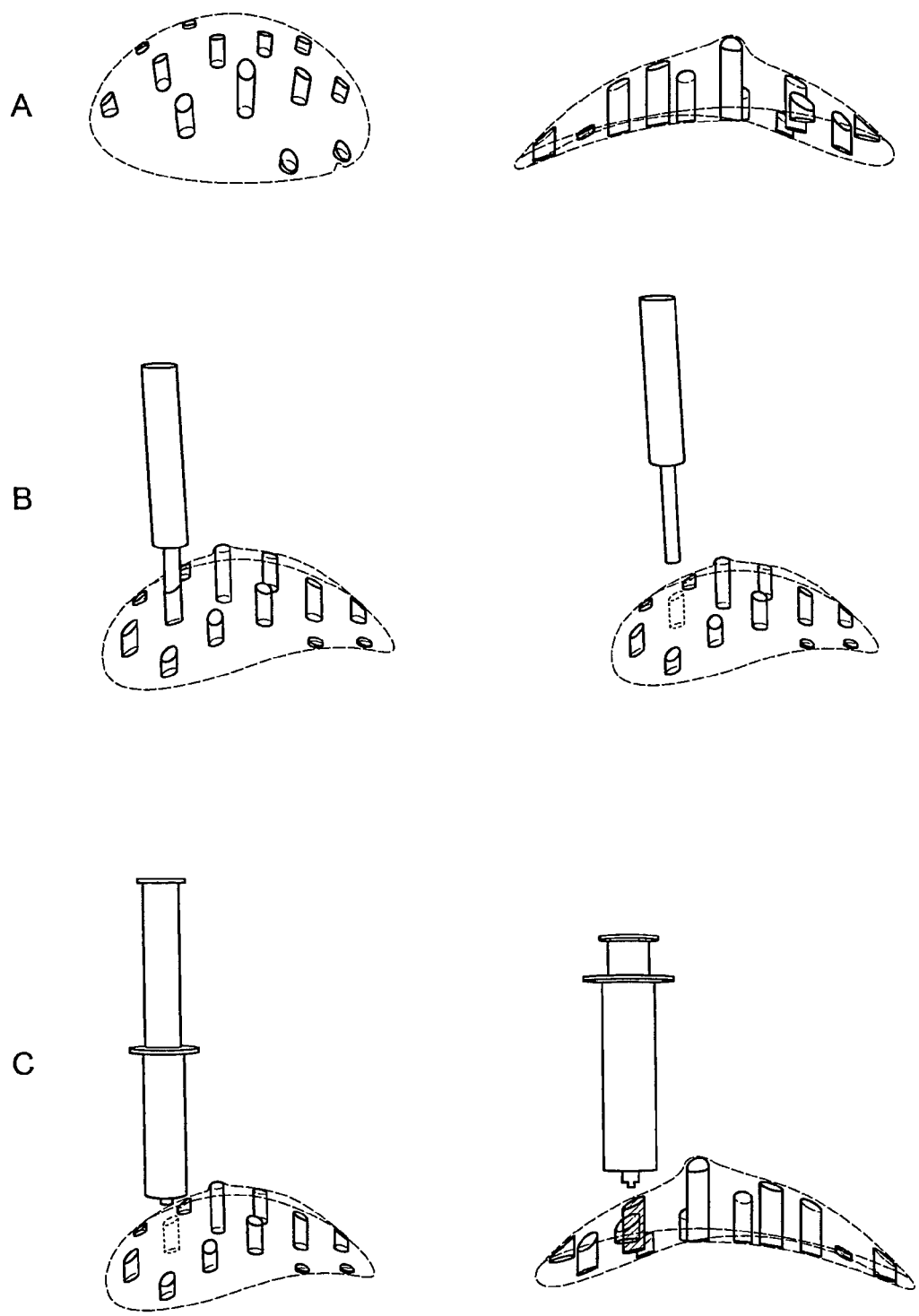
FIG. 2 shows an embodiment of the invention in which the implant is a breast implant, as well as schematic depictions of steps during the use of such an implant. (A) Angular view (left) and side view (right) of a breast implant according to the invention wherein the voids are not interconnected and arranged in parallel (i.e. a non-convergent geometric orientation). (B) Removal of the space-occupying structures from the implant, in this case by punching out (left) and subsequently withdrawing (right) the space-occupying structures from the implant with a specialized removal tool. (C) Introduction of transplantation cells into the resulting void space not filled with a space-occupying structure, in this case by lipofilling (i.e. introduction of fat tissue) by injection with a syringe. Left bringing the syringe into contact with the site of injection. Right: The void has been filled with fat tissue.

FIG. 2 shows individual steps to be carried out during the use of an implant according to the invention, illustrated for the example of a breast implant comprising a three-dimensional scaffold structure made of biodegradable material. In the exemplary embodiment of the implant used, the voids are not interconnected and are arranged in parallel, i.e. in a non-convergent geometric orientation (FIG. 2A). While in the example shown in FIG. 2 solid space-occupying structures are used, other types of space-occupying structures are equally possible, as defined in the embodiments of the invention above.

For breast reconstruction or augmentation, the implant is surgically implanted at the desired site. After several weeks of incubation (such as 6-8 weeks), the biodegradable scaffold material will be partially degraded and connective tissue and host vasculature will have penetrated into the scaffold structure and the space emerging due to scaffold structure degradation. At this point, the solid space-occupying structures are surgically removed. As shown in FIG. 2B, this may be achieved by a specialized removal tool according to the invention.

According to the embodiment shown in FIG. 2B, the removal tool has a grip to which a blade is attached at its distal end. The blade is designed as a biopsy punch blade with a circular shape. To reduce scar formation through the biopsy punch blade, a small linear incision is inflicted to the skin and tissue overlying the space-occupying structure through which the blade of the removal tool is inserted. The shape and size of the circular blade mirrors the round shape and the diameter of the cross-section of the space-occupying structures. Thus, by applying the removal tool with correct positioning, it allows to accurately excise the space-occupying structure (FIG. 2B, left; Note that the depictions of FIG. 2 are schematic illustrations that show the depicted steps at the isolated implant. In practice, the implant will of course be located in the body of a patient during the removal step of FIG. 2B and the step of introducing the transplantation cells of FIG. 2C). The removal tool further includes an appliance that allows grasping the excised space-occupying structure (not visible in the depiction of FIG. 2B). Upon grasping the excised space-occupying structure, the removal tool is withdrawn and thus the excised space-occupying structure is removed, leaving behind a void space that was previously filled with the space-occupying structure (FIG. 2B, right) and that, due to the previous occupation by the space-occupying structure, is free of invaded connective tissue and vasculature. Subsequently, the space-occupying structures will also be removed from the other voids of the implant.

As a following step, transplantation cells, i.e. cells of the desired cell type (differentiated cells or precursor cells) that are to be introduced for tissue reconstruction, are introduced into this void space. In the case of a breast implant as shown in FIG. 2, the transplantation cells may be fat tissue obtained from a donor site of the same patient that is injected with a syringe into the void space. Since in the example of FIG. 2 the voids are arranged in parallel arrangement and are not interconnected, an individual injection has to be carried out for each void space separately.

Implants according to the invention and their use as exemplified above result in the creation of a pre-formed bed of connective tissue and vasculature into which the transplantation cells are introduced. Thus, a stable association of the introduced cells with the implantation site, optimal supply of the transplanted cells with oxygen and metabolites, and minimal necrosis and resorption are achieved. At the same time, the inclusion of voids and space-occupying structures in the implant makes sure that there is sufficient space for introduction of an adequate amount of transplantation cells into the pre-formed bed of vascularized connective tissue upon removal of the space-occupying structures.

FIG. 3 provides another example of the preparation and use of an implant according to the invention. In contrast to the embodiment described in FIG. 2, FIG. 3 shows the use of a breast implant with interconnected voids in a convergent arrangement (FIG. 3A, B). Moreover, while FIG. 2 shows an implant with solid space-occupying structures, the space-occupying structures of the implant of FIG. 3 consist of a liquid- or hydrogel-filled sheath and thus are collapsible. The sheath consists of a biocompatible polymeric material that is impermeable to the liquid or hydrogel.

The implant is produced with voids containing a sheath in the shape of a tubing, and the sheath is subsequently filled with a liquid or hydrogel (FIG. 3A, B). Since in the embodiment of FIG. 3 the voids (and also the space-occupying structures) are interconnected, all the space-occupying structures can be filled with the liquid or hydrogel through a single access point, which is subsequently sealed.

The implant is then implanted at the site of intended tissue reconstruction, in the embodiment of FIG. 3 the area of the breast of a patient where breast reconstruction/augmentation is desired (FIG. 3C). Upon implantation, the implantation site is left to heal for several weeks. During this time, connective tissue and blood vessels will invade the implant, which, if the implant comprises a three-dimensional scaffold structure made of biodegradable material, is concurrently gradually degraded.

After 6-8 weeks, the fluid within the space-occupying structures is removed, in the exemplary procedure of FIG. 3 by piercing of the space-occupying structures and aspiration of the fluid with a syringe (FIG. 3D, E). Since the voids and space-occupying structures are interconnected, the complete volume of liquid or hydrogel can be removed from the space-occupying structures through the single access point at the origin of the convergent void system. Upon removal of the liquid or hydrogel, the space-occupying structure collapses to an empty sheath of polymeric material.

Whereas the specialized removal tool shown in FIG. 2B is particularly useful for the removal of solid space-occupying structures, the collapsible space-occupying structures of the embodiment depicted in FIG. 3 can be removed after aspiration of the liquid/hydrogel simply by grasping the interconnected space-occupying structures at the origin of the convergent void system with surgical forceps and withdrawing them from the implantation site. Removal of the space-occupying structures is further simplified and collateral tissue damage during removal is reduced, if the space-occupying structures used have a surface coating that rejects tissue and cells from invasion, such as a coating with the drug tacrolimus (not shown in the embodiment of FIG. 3).

Upon removal of the space-occupying structures, void spaces are left behind into which transplantation cells (in case of the breast reconstruction shown in FIG. 3 fat tissue isolated from a different site of the patient's body) are injected (FIG. 3F, G).

Due to the convergent arrangement of the voids and space-occupying structures, in the embodiment of the implant shown in FIG. 3 aspiration of the liquid/hydrogel from the space-occupying structures, removal of the collapsed space-occupying structures and injection of the fat tissue can all be carried out through a single, small incision at the origin of the convergent arrangement by a minimally invasive procedure.

The use of (biodegradable) shape-memory polymer (SMP) materials for construction of three-dimensional scaffolds of implants according to the invention is highly advantageous, in particular with regard to minimizing the tissue and skin damage that is necessary for surgical insertion of the implant. FIG. 4 shows an example of a scaffold structure of a breast implant made from a shape-memory polymer to illustrate the principle of an SMP implant. The original, permanent shape of the scaffold corresponds to the extended shape of the fully-formed breast implant, as shown in FIG. 4A. Below a certain "trigger temperature", the scaffold can be deformed into other shapes, such as the more compact, disc-like shape depicted in FIG. 4B. However, once the temperature of the scaffold is increased and reaches or surpasses the trigger temperature, the scaffold will return to its original, permanent shape, which is the extended shape of the breast implant of FIG. 4A. As the skilled person will appreciate, the trigger temperature in the context of the present invention should equal are be just below the body temperature of the patient undergoing transplantation.

Figure 5:
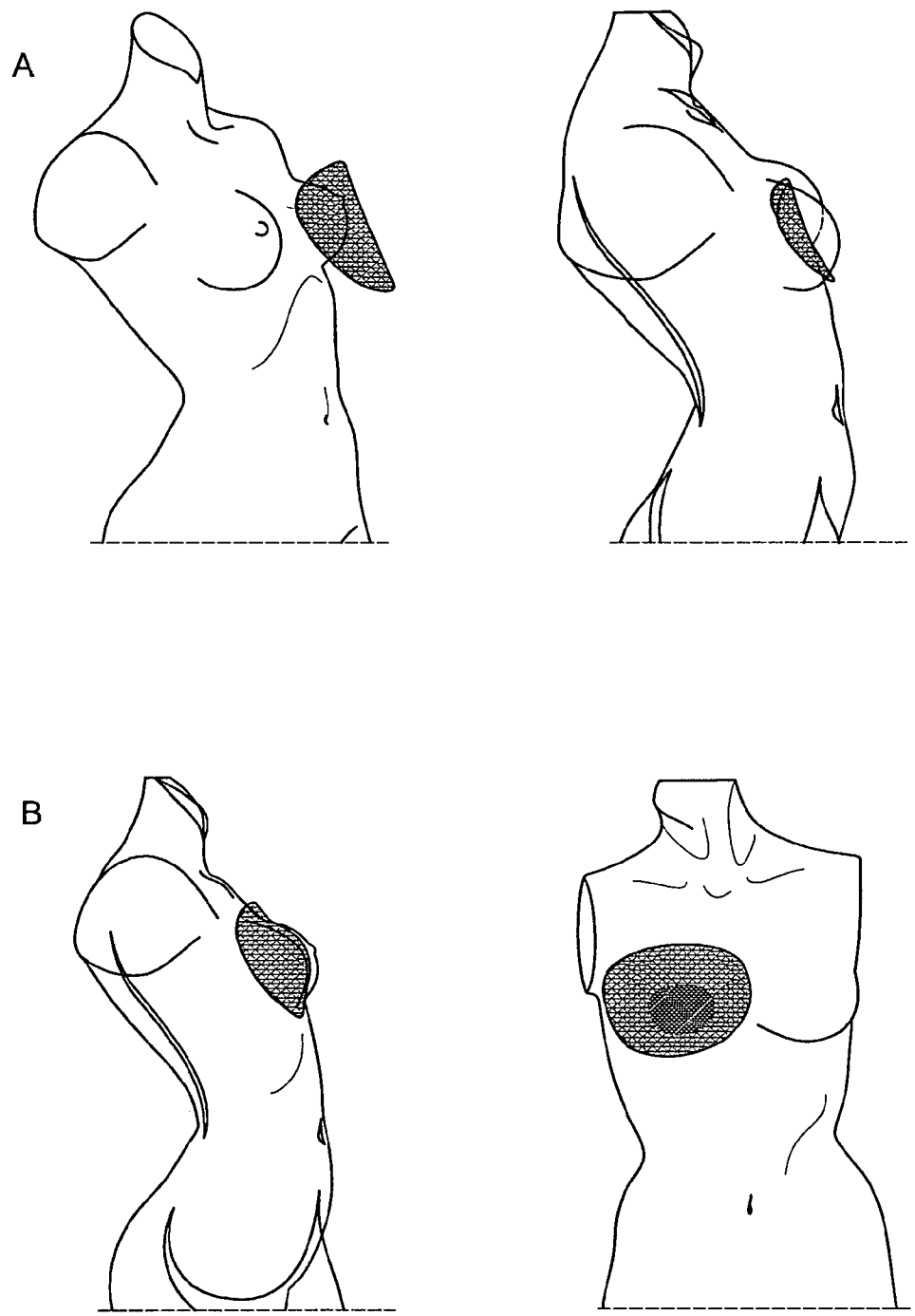
FIG. 5 shows schematic depictions of different stages during implantation of a breast implant scaffold made from a shape-memory polymer. (A) Before (left) and right at the time of implantation (right) at the site of reconstruction, the scaffold exists in the deformed, disc-like shape that it can take at room temperature. (B) Upon reaching body temperature (37° C.), the scaffold returns to its original, permanent shape, i.e. the fully-formed shape of a breast implant.

The practical application of an implant according to the invention comprising an SMP scaffold is exemplified in FIG. 5 (to simplify the depiction, only the scaffold component of the breast implant is shown). A breast implant scaffold with the characteristics as described in FIG. 4 (i.e. the original, permanent shape of the scaffold corresponds to the extended shape of the fully-formed breast implant; and the trigger temperature of the SMP material is identical to body temperature) is deformed to a compact, disc-like shape at room temperature (FIG. 5A, left). Owing to its compact structure, the deformed scaffold can be implanted by the surgeon more easily and through a smaller incision than an implant with an extended scaffold structure and placed at the desired site of implantation (FIG. 5A, right). As soon as the implant is inside the body of the patient, the SMP implant adapts from room temperature to the patient's body temperature. Once it reaches body temperature, the SMP material returns to its original, permanent shape which is the extended shape of a fully-shaped breast implant (FIG. 5B). The surgeon can then close the small incision safely.

While removal of the space-occupying structures may occur with a specialized removal tool as described in the procedure shown in FIG. 2B above or by withdrawal of collapsible space-occupying structures as described in connection with FIG. 3 above, the present invention also provides for a specialized removal device for the removal 6f ferromagnetic or superparamagnetic space-occupying structures from an implant according to the invention.

An exemplary embodiment of a removal device for removing ferromagnetic or superparamagnetic space-occupying structures from a breast implant is shown in FIG. 6. The removal device has the shape of a flattened can which is traversed by twelve rod-shaped electromagnets. The bottom surface of the container has a bell-shaped indentation, thus providing for a good fit to the breast.

To remove ferromagnetic or superparamagnetic space-occupying structures from an implant at a transplantation site, small incisions are made through the overlying tissue at the positions where the space-occupying structures reside, thus creating a path through the tissue along which the space-occupying structures may be removed. Then the indented surface of the removal device is brought into contact with the implantation site. The space-occupying structures to be removed have the same spatial distribution as the electromagnets on the removal device, such that the electromagnets of the removal device are in perfect orientation for interacting with the space-occupying structures to be removed. Moreover, since the surface of the removal device that contacts the breast has a breast-shaped indentation, a tight fit of the surface of the removal device to the breast is ensured, thus bringing the electromagnets into direct contact with the space-occupying structures to be removed.

At this point, the electromagnets of the removal device are turned on. The strong magnetic forces exerted by the powerful electromagnets attract the ferromagnetic or superparamagnetic space-occupying structures, such that they get attached to the electromagnets, and the removal device is withdrawn from the body of the patient. The space-occupying structures move along with the removal device and are thus removed from the patient's body.

The present invention also provides special laydown patterns for implant scaffolds that allow to adapt the three-dimensional scaffold of the implant to the specific needs of an implant with voids and space-occupying structures.

Figure 7:
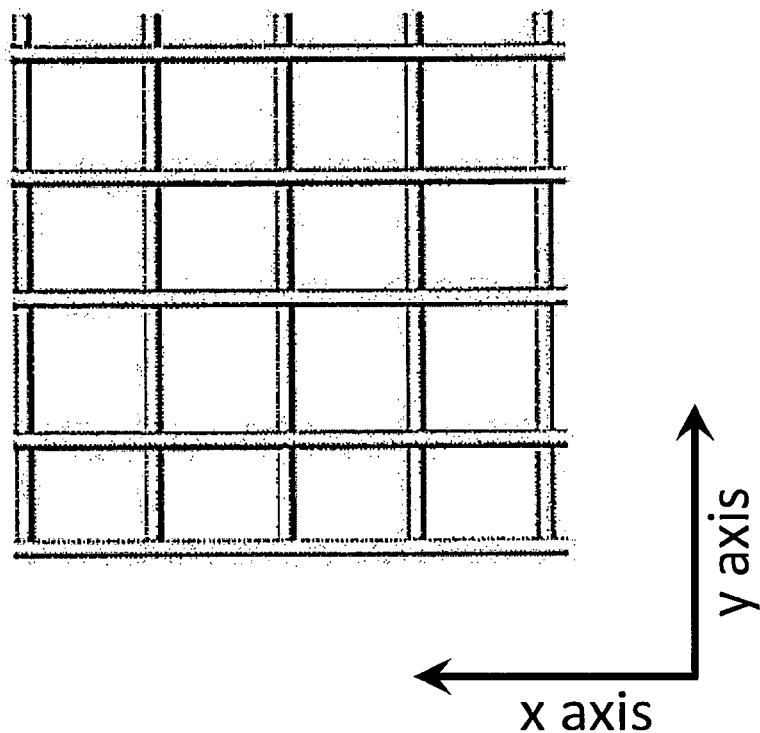
FIG. 7 shows the construction principle of a conventional laydown pattern as commonly used in scaffolds of implants.

FIG. 7 shows the principle of a conventional laydown pattern for implant scaffolds. Pictured are two layers (a bottom layer of equidistantly arranged, parallel bars oriented along the y axis and a top layer of equidistantly arranged, parallel bars oriented along the x axis) that illustrate the construction principle of such a conventional laydown pattern. The individual bars are physically connected at the points of contact with other bars. The pattern of the two layers is repeated in the z direction (i.e. out of the plane of the paper), resulting in a three-dimensional scaffold structure as shown in FIG. 9A (see below).

Figure 8:
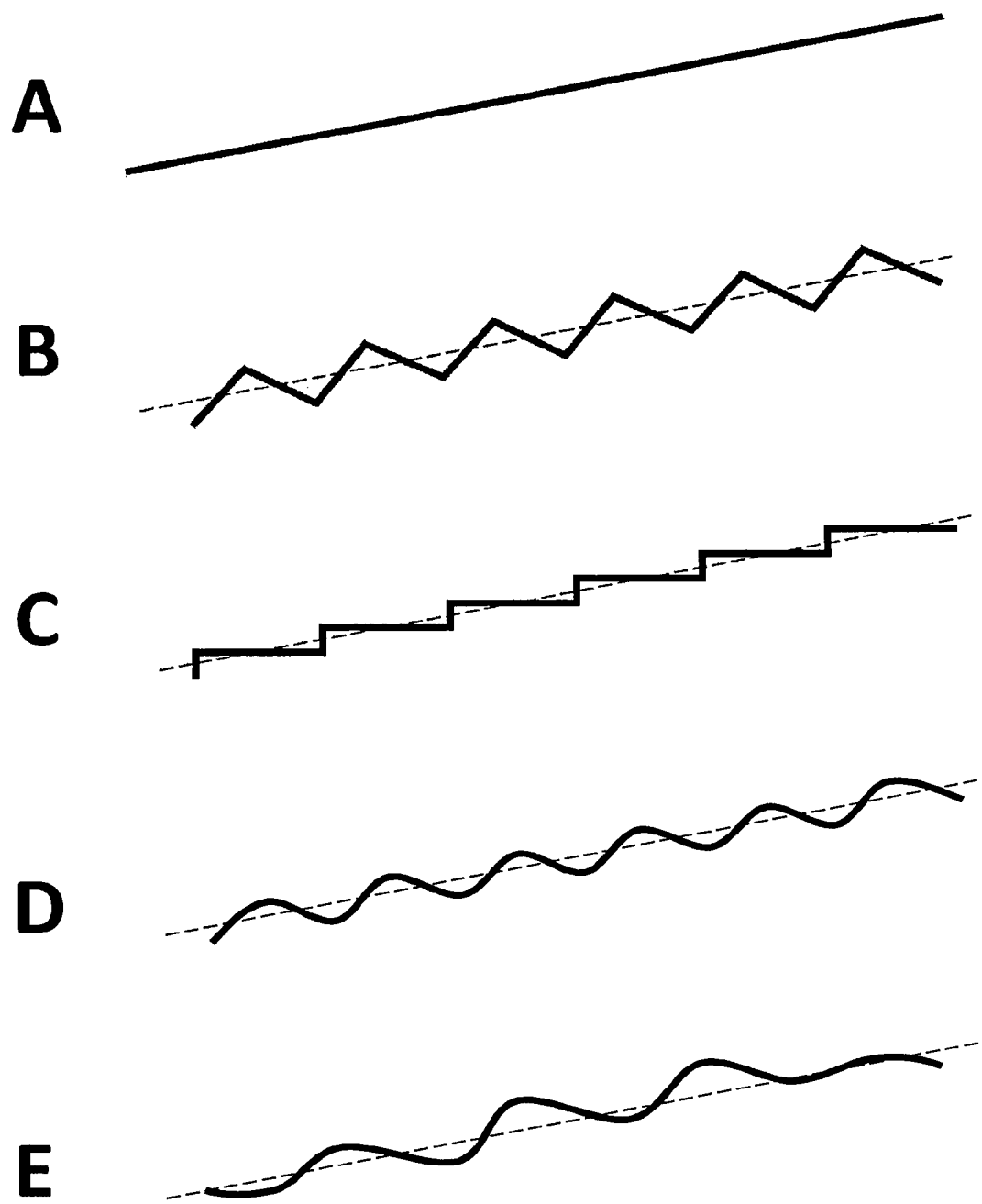
FIG. 8 shows examples for different types of bars that according to the invention may be employed for the formation of three-dimensional implant scaffolds. (A) Straight bar. (B, C) Examples of bars with regular zigzag structure. (D, E) Examples of bars with wiggled structure.

FIG. 8 shows examples for different types of bars that may be used for the formation of three-dimensional scaffold structures of implants according to the invention. This includes straight bars as they are also used in conventional laydown patterns (FIG. 8A), bars with regular zigzag structure (FIG. 8B), bars with regular zigzag structure, wherein the zigzag structure has a "staircase-shape" (FIG. 8C), bars with regular wiggled structure (FIG. 8D) and bars with irregular wiggled structure (FIG. 8E). As the skilled person will appreciate, the bars shown in FIG. 8 are only of exemplary nature, and bars with various other regular or irregular zigzag structures, wiggled structures or combinations thereof are also contemplated by the present invention.

The central axis of the bars depicted in FIGS. 8 B-E is indicated as a dashed line. In a parallel arrangement of bars with zigzag or wiggled structure, the bars will be oriented such that the central axis of the bars will be parallel.

FIG. 9 shows different laydown patterns for three-dimensional scaffold structures of implants formed from stacks of multiple interconnected layers, each layer being composed of a plurality of parallel bars: FIG. 9A is an illustration of a three-dimensional scaffold structure with a conventional laydown pattern, as it is obtained if the construction principle of FIG. 7 is followed. FIG. 9B, in contrast, shows an embodiment of the three-dimensional scaffold structure according to the invention, wherein the parallel bars of every other layer have a regular, staircase-shaped zigzag structure and wherein the bars of subsequent layers with straight bars are offset with respect to each other. FIG. 9C is a depiction of an alternative embodiment of the three-dimensional scaffold structure according to the invention, wherein the parallel bars of every other layer have a wiggled structure. In the three-dimensional scaffold structure of FIG. 9D, a scaffold according to the invention is represented, wherein all bars have a wiggled structure.

The scaffold structures shown in FIG. 9 B-D represent only examples, and various other scaffold structures also fall within the scope of the present invention. Thus, for example bars of various other shapes and combinations of bars with zigzag structure and wiggled structure are contemplated as well. Moreover, the layers within the stacks of FIGS. 9 B-D are all arranged such that the bars of any layer have a perpendicular arrangement with respect to the bars of the subsequent layer. According to other (not depicted) embodiments of the invention, however, subsequent layers may also be rotated by other angles, for example by an angle of 60°, such that the third layer after any layer X (i.e. layer X+3) has again an orientation of its bars that is parallel to the bars of said layer X.

In FIG. 10 schematic depictions of different three-dimensional scaffold structures are provided in side view representation. FIG. 10A is a scaffold with conventional laydown pattern without offset. This scaffold structure is identical to the one shown in FIG. 9A. In contrast, FIG. 10B shows an exemplary laydown pattern according to the invention in which, of those layers that have bars oriented along the y axis (i.e. pointing out of the paper plane), every layer is, with respect to the previous layer, offset by a distance of ½ times the distance between the bars of said layer (i.e. the bars of the layer are parallel-shifted within the plane of the layer, which in this depiction means shifted along the x axis). This means that every other layer with bars oriented along the y axis is again vertically "in line", i.e. the bars of such layers can geometrically be brought to congruency by a simple translation along the z-axis.

While the embodiment shown in FIG. 10B has a scaffold structure with a repetition after every second layer of the same bar orientation (i.e. every fourth layer in FIG. 10B, if all layers are counted, independent of the orientation of their bars), the present invention also embraces embodiments with other repetition patterns. For example, if the layers with the same orientation of their bars are shifted by a distance of ⅓ times the distance between the bars, repetition is achieved after every third layer, and if the layers with the same orientation of their bars are shifted by a distance of 1/m times the distance between the bars, repetition is achieved after every m-th layer of the same orientation.

FIG. 11 shows experimental data obtained from compression testing performed on scaffolds with conventional laydown structure as shown in FIG. 10A (data in FIG. 11A) and with a laydown pattern according to the invention having an offset as shown in FIG. 10B (data in FIG. 11D). In these experiments, 3 sets of 20 equal-sized square sheets of porous scaffolds were fabricated from polycaprolactone. The porosity, strut/bar size and strut spacing were kept constant across all the groups; however, one group (Group A) was formed with a conventional laydown structure as shown in FIG. 10A, another group (Group B) was formed with a laydown pattern according to the invention having an offset as shown in FIG. 10B and the third group (Group C) was formed with a wiggled laydown pattern according to the invention as shown in FIG. 9C. Compression testing was performed on the explanted scaffolds using an Instron 5848 microtester fitted with a 500 N load cell. All scaffolds from Group B were compressed in the Z direction (axial compression), all scaffolds from Group C in the X direction (transverse compression) whereas 50% of the Group A scaffolds were compressed in Z-direction and the remaining were compressed in the X direction. The testing protocol consisted of a 2 mm compression of the scaffolds at a rate of 0.6 mm/min.

The data obtained from the microtester was used to plot a stress-strain curve which, as a skilled person will appreciate, corresponds to the stiffness of the construct. FIGS. 11A and 11B show a stress vs strain plot of Group A and Group C scaffolds, respectively, whereas FIGS. 11C and 11D show a stress vs strain plot of Group A and Group B scaffolds, respectively.

From these data, it can be concluded that the scaffold structure according to the invention having a zigzag laydown pattern is more flexible in the XY direction, can take the same stress as the control scaffold and displays a higher range of elastic deformations as compared to control scaffolds with a conventional laydown pattern fabricated with the same parameters. Similarly, scaffold structures with an offset in the Z direction according to the invention are more flexible in their axial Z direction.

Figure 12:
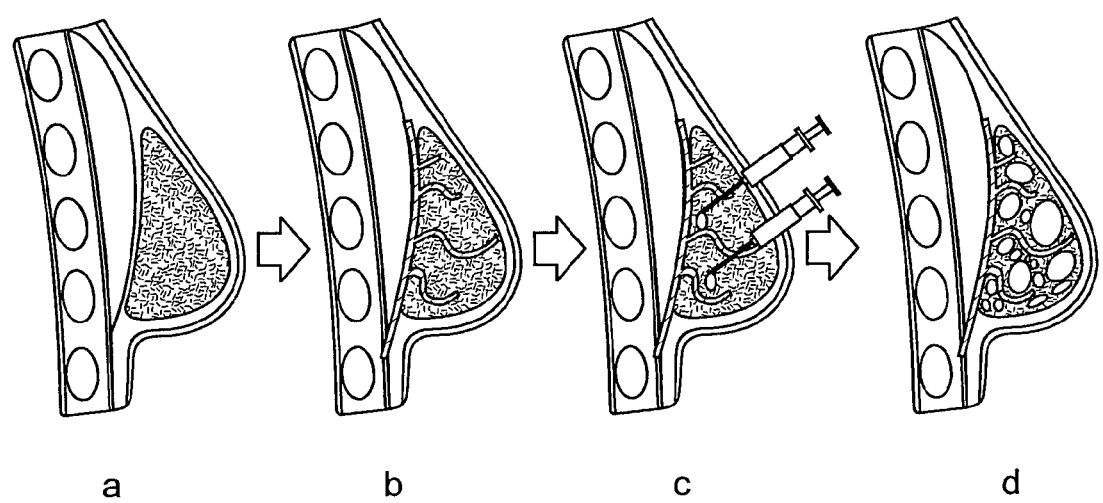
FIG. 12 shows the principle of the method for tissue reconstruction in the body of a patient according to the seventh aspect of the invention, illustrating the overall concept of prevascularisation and delayed fat injection. An empty scaffold is first implanted at the breast region without the addition of any cells or growth factors. Over the next e.g. 2-3 weeks, connective tissue and vasculature invades within the scaffold volume forming a bed of capillaries within the pores. Fat is then injected into the pores of the scaffold. Owing to the presence of the pre-formed vascular bed would allow the fat to remain stable at the implantation sites.

FIG. 12 is an exemplary depiction of the different steps of the method for tissue reconstruction in the body of a patient according to the seventh aspect of the invention, illustrated for the example of a breast reconstruction. A breast implant comprising a three-dimensional scaffold structure made from a biodegradable material is implanted at the desired site of breast reconstruction (a). The scaffold structure is allowed to remain at the implantation site for a period of 6-8 weeks during which connective tissue and especially host vasculature penetrates into the scaffold structure (b). After this period, fat is isolated from a donor site within the patient's body and injected into the scaffold structure (c). The presence of a pre-formed bed of connective tissue and vasculature allows the fat to remain stably within the implantation site with minimal tissue necrosis and resorption (d). Moreover, such a structure would also better mimic the internal architecture of the breast.

One disadvantage of the method depicted in FIG. 12 is that, since the invading connective tissue may take over the majority of the volume initially occupied by the biodegradable scaffold structure, no further volume may remain for the secondary injection of fat tissue injected during step (c) (or other transplantation cells to be injected). As the skilled person will appreciate, the use of an implant according to the present invention (comprising a three-dimensional scaffold structure with voids and removable space-occupying structures as described above) and, accordingly, a method for tissue reconstruction using such an implant (as defined in the eighth aspect of the invention above) overcomes such problems, because the space-occupying structures will protect void spaces that cannot be invaded by connective tissue or vasculature and that, upon removal of the space-occupying structures, become available for introduction of fat tissue or other transplantation cells.

EXAMPLES

Example 1

This example combines delayed fat injection with an acellular biodegradable scaffold. In this method of implantation, the scaffold is first implanted with no fat tissue into the implantation site. A fibrin clot is formed immediately after implantation of the scaffold from the hematoma caused by the surgical procedure (Henkel et al., 2013; Salgado et al., 2004). The clot consists of platelets embedded in a mesh of cross-linked fibres, together with a growth-factor rich cocktail of fibronectin, vitronectin and thrombospondin. The fibrin clot and the associated growth-factor cocktail may stimulate a strong angiogenic response and induce highly organised connective tissue to penetrate into the scaffold. After a fixed period of time, fat is isolated from a donor site within the patient's body and injected into the scaffold (see FIG. 12 for a visualisation of this concept). The amount of fat that can be harvested from the patient without encountering donor site morbidity depends on the body composition of the patient—whereby a larger volume of fat can be extracted from patients with higher body fat percentage. In this study, based on the expertise of our surgical team and a literature search, 4 cm$^3$ of adipose tissue was considered to be the maximum amount that can be harvested from a patient with a very low body fat percentage without encountering donor-site complications. Therefore, the scaffolds were seeded with 4 cm$^3$ of fat isolated from the donor—representing 5.23% of the total volume of the scaffolds.

The study of Example 1 characterised adipose tissue retention in large 75 cm$^3$ acellular polycaprolactone-based scaffolds subjected to a delayed fat injection implanted in a large animal model (pigs) for a period of 24 weeks.

Study Design and Sample Size Rationale

A randomised and blinded animal study was carried out, evaluating the adipose tissue regenerative potential of large 75 cm$^3$ biodegradable scaffolds for 24-weeks using a subglandular swine animal model.

Three experimental groups were included in this study:
1) Empty scaffold (negative control).
2) Scaffold containing 4 cm$^3$ lipoaspirate.
3) Empty scaffold+2 week prevascularisation period. After 2 weeks of prevascularisation, 4 cm$^3$ of lipoaspirate was injected into scaffolds.

The primary endpoint evaluated was the percentage of adipose tissue area compared to overall tissue area (AA/TA). In an optimal case, no statistically significant difference in mean AA/TA between the experimental groups (prevascularisation+lipoaspirate and lipoaspirate-only groups) and the healthy breast tissue group (<10% difference in means) would be detected, while, at the same time, a statistically significant difference between the AA/TA of negative control (empty scaffold) group and healthy breast tissue group would be detected. For an expected standard deviation of 5 (5 point scale), a sample size of 12 used in this study gives a statistical power of 85.7%. Statistical Power calculations were performed using Researcher's Toolkit Statistical Power Calculator (DSS Research, Fort Worth, USA).

Rules for Stopping Data Collection

Data collection was stopped and the scaffolds were excluded from further analysis if one of the two following conditions were met (all signs verified by experienced plastic and veterinary surgeons):
1) Detection of infection.
2) Long-standing signs of haematoma or seroma.

Selection of Endpoint

Since adipose tissue undergoes remodelling multiple times during the wound healing process, in this study a primary endpoint of 24 weeks was chosen to be adequate in terms of addressing tissue permanence mechanisms.

Randomisation and Blinding

Two study parameters were randomised:
1) Allocation of a scaffold to an experimental group.
2) Allocation of a scaffold to a subglandular pocket.

For both parameters, randomisation sequence was created using Excel 2010 (Microsoft, Redmond, USA) with a 1:1 allocation using random block sizes of 2 and 4 by an independent researcher. Except for the plastic surgeon operating on the animals, all researchers were kept blind to the allocation of scaffold and subglandular pockets to the experimental groups. Geographical separation ensured minimal contact between the operating surgeon and the researcher performing histological and qualitative analyses. Upon explantation, the operating surgeon coded each scaffold with an ID (JT-n; where n=1 to 12) and kept the key hidden from the researchers performing downstream analyses. The key was revealed to the researchers only upon completion of the data analysis. In summary, all study outcomes were assessed in a blinded manner.

Design & Fabrication of Scaffolds

Rapid prototyped hemisphere-shaped polycaprolactone-based scaffolds were designed and manufactured by Osteopore International Pte Ltd (Singapore). All scaffolds were produced using medical-grade polycaprolactone adhering to ISO 11137 (Sterilisation), 13485 (Quality Systems), 11607 (Packaging), and 14644-1 (Clean Room) standards.

In Vivo Implantation into Minipigs

The animal experiments were performed under GMP conditions at PWG Laboratories, Singapore with ethical approval from PWG Laboratories which, in turn, is maintained in accordance with NIH Guide for the Care and Use of Laboratory Animals. Two female adult immunocompetent minipigs were used in this study. The operation was performed under general anaesthesia, following the standard protocol of sterility requirements for breast augmentation procedures. Careful homeostasis was also maintained throughout the surgical procedure. 3 separate subglandular pockets were created on each side of the mammary region via a longitudinal incision. 6 implants were randomly placed in each animal. Prior to implantation, all scaffolds were trimmed by 1 mm from the outer boundary at the operating table by the surgeon to ease the implantation process and gain access to the inner pores by removing the outer shells of the scaffolds.

In groups 2 and 3, a midline incision was made and adipose tissue was obtained via the Tulip system (Tulip Medical Products, San Diego, USA). The lipoaspirate was injected directly into the interconnected pore architecture of the scaffolds—using a 10-cm$^3$ Tulip cell-friendly injector.

After the placement of the implants each pocket was closed with absorbable vicryl sutures, such that the implants were fixed stably and had no contact to each other. Finally, the skin was sutured with interrupted 2.0 Ethilon sutures.

Histological and Histomorphometrical Analyses

Hematoxylin & Eosin (H & E)

Implants were harvested from the minipigs after 24 weeks and were fixed with 4% PFA (paraformaldehyde), cut into 10 mm×10 mm cube sections, dehydrated and embedded in paraffin using a tissue processor (Excelsior ES, Thermo Scientific, Waltham, USA). Constructs were horizontally sliced to 5 µm, deparaffinised with xylene, rehydrated with a decreasing series of ethanol and stained with H & E (Hematoxylin and eosin stain). Stained slides were scanned with a BIOREVO BZ-9000 microscope (Keyence, Itasca, USA) at 5× magnification.

Massons Trichrome Staining

The slides were deparaffinised with xylene, rehydrated with a decreasing series of ethanol and re-fixed in Bouin's solution at room temperature overnight. After rinsing in tap water for 10 minutes, the slides were stained in Weigert's iron hematoxylin for 10 minutes, rinsed in running warm tap water, stained in Biebrich scarlet-acid fuchsin solution for 10 minutes and transferred directly into aniline blue solution and stained for 10 minutes. The slides were rinsed briefly in distilled water and differentiated into 1% acetic acid solution for 5 minutes.

Histomorphometry

Histomorphometrical analyses were carried out with the Osteomeasure histomorphometry analysis system (Osteometrics Inc., Decatur, Ga., USA). All measurements were performed blinded on 8 randomly chosen sections from each scaffold from each group (4 from the superficial regions and 4 from the deep regions). To determine the average adipose tissue area, the total area of the adipose tissue was first calculated (A). Secondly, the total area occupied by the scaffold struts was measured (S). Finally, the combined area of the tissue section was measured (C). The ratio of adipose tissue area to total tissue area (R) was calculated using the following formula (Chhaya et al., 2015):

$$R = \frac{A}{(C-S)} * 100\%$$

ImageJ (National Institutes of Health, MA, USA), in conjunction with Adipocyte Tools plugin developed by Montpellier RIO Imaging (Montpellier, France), was used for all automated calculations involving cell size distribution. The field of view (FOV) from each histological section was kept uniform. Background was first removed from each histological section by the pre-processing macro within the Adipocyte Tools plugin using the thresholding method. Minimum size of each cell was chosen to be 80 µm, maximum size as 800 µm and the number of dilates were set to be 10. These threshold values were kept constant across all samples and groups. The same threshold was also chosen to automatically set regions of interest (ROI) around the adipose cells. The automated method generated a small number of ROI artefacts. Artefacts that could be detected visually were manually removed. In order to remove the remaining artefacts, 10% of the smallest and 10% of the largest ROIs were excluded from any further analysis.

In order to calculate the blood vessel density, all blood vessels that showed red erythrocytes within the lumen were counted. The number of blood vessels was divided by the total tissue area to get the density. Values based on 4 stitched microphotographs from each scaffold per experimental condition.

Estimation of Adipose Volume in TEC (Tissue Engineered Constructs)

Since the entire volume of the scaffold was filled with host tissue, it is reasonable to assume that each scaffold held 60 cm$^3$ of total tissue volume at the end of the implantation period (75 cm$^3$ total volume×80% porosity=60 cm$^3$ volume available for tissue growth; scaffold degradation has not been taken into account in order to simplify calculations).

Figure 19:
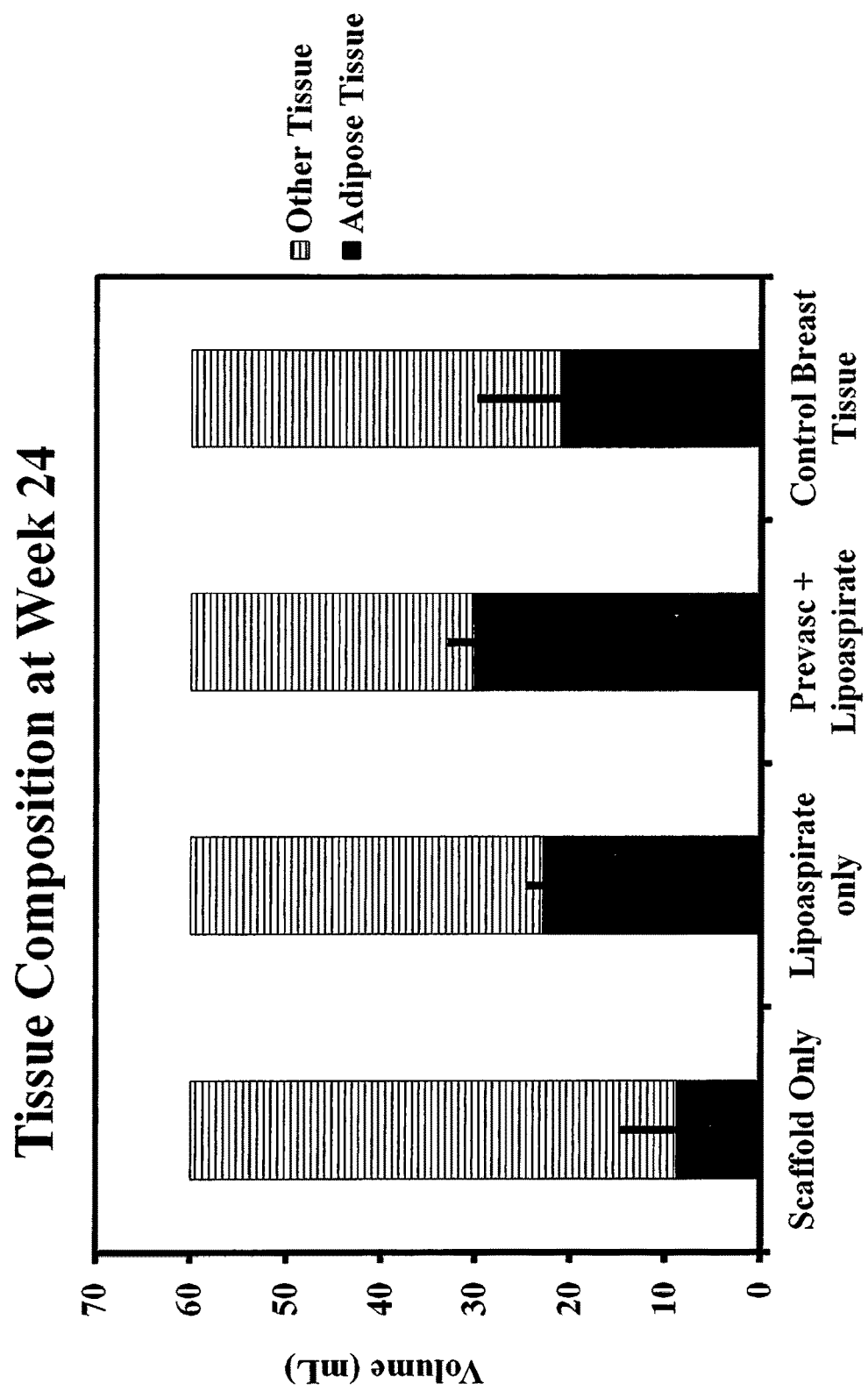
FIG. 19 shows representative images of Masson's Trichrome stained tissue sections obtained from Example 1.
Figure 19:
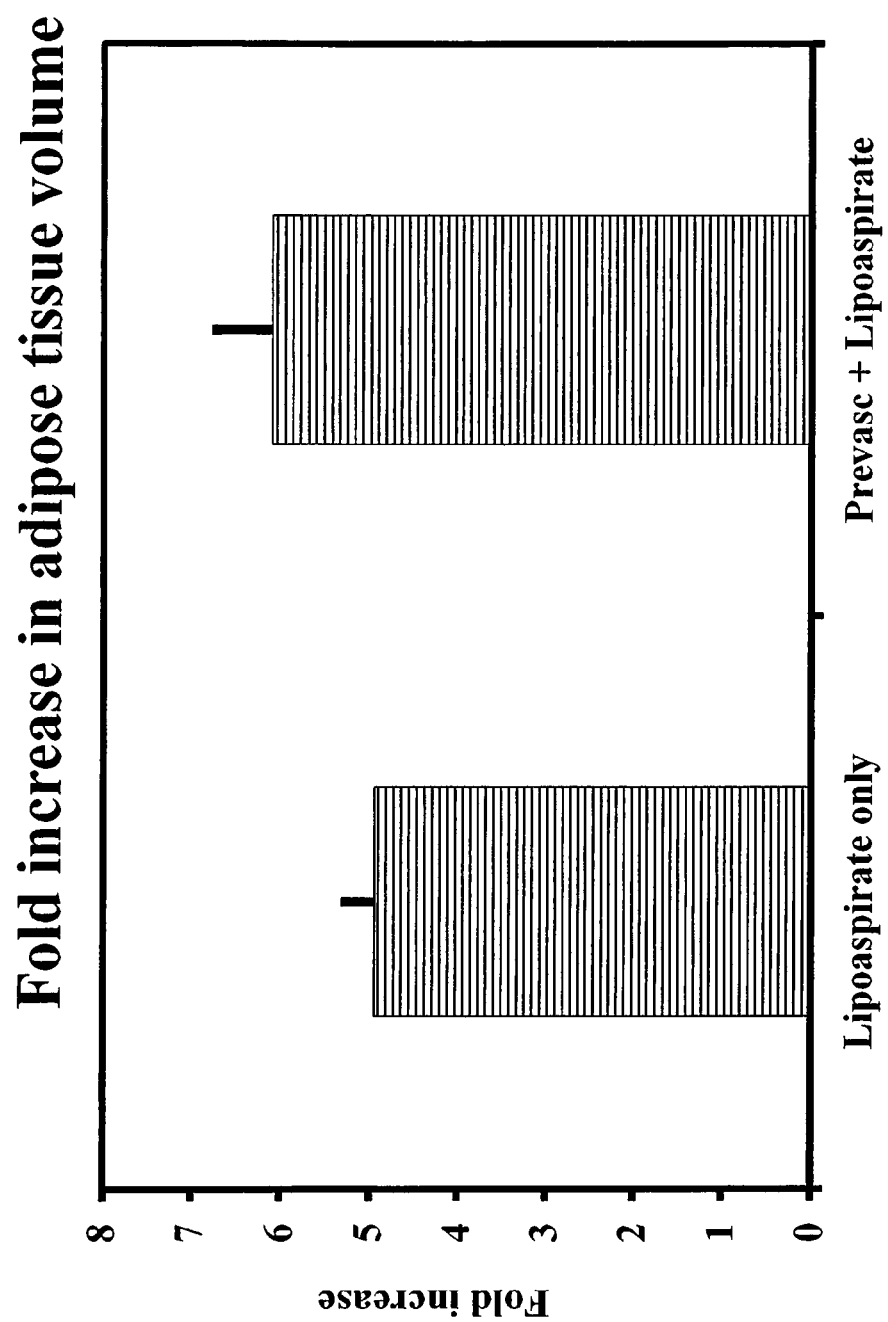

The relative adipose tissue fraction values shown in FIG. 19G have been calculated from 8 randomly chosen tissue sections, each 40 mm×25 mm in dimensions. The estimated volume fraction of adipose tissue in each group was extrapolated from these adipose tissue area fraction values.

Statistical Analysis

All data are represented as mean±SD and are subjected to one-way analyses of variance (one-way ANOVA) and Tukey's post-hoc test (Prism 6, GraphPad, San Diego, USA). Significance levels were set at p<0.05. All error bars represent standard deviation.

Clinical Observations

The surgery and implant placement were tolerated well by all animals and no apparent clinical signs of infection were observed throughout the implantation period. 12 weeks after the initiation of the study, one scaffold was observed to have seroma accumulation in the surgically-created pocket and was therefore excluded from further analysis.

Scaffold Characterisation

Figure 13:
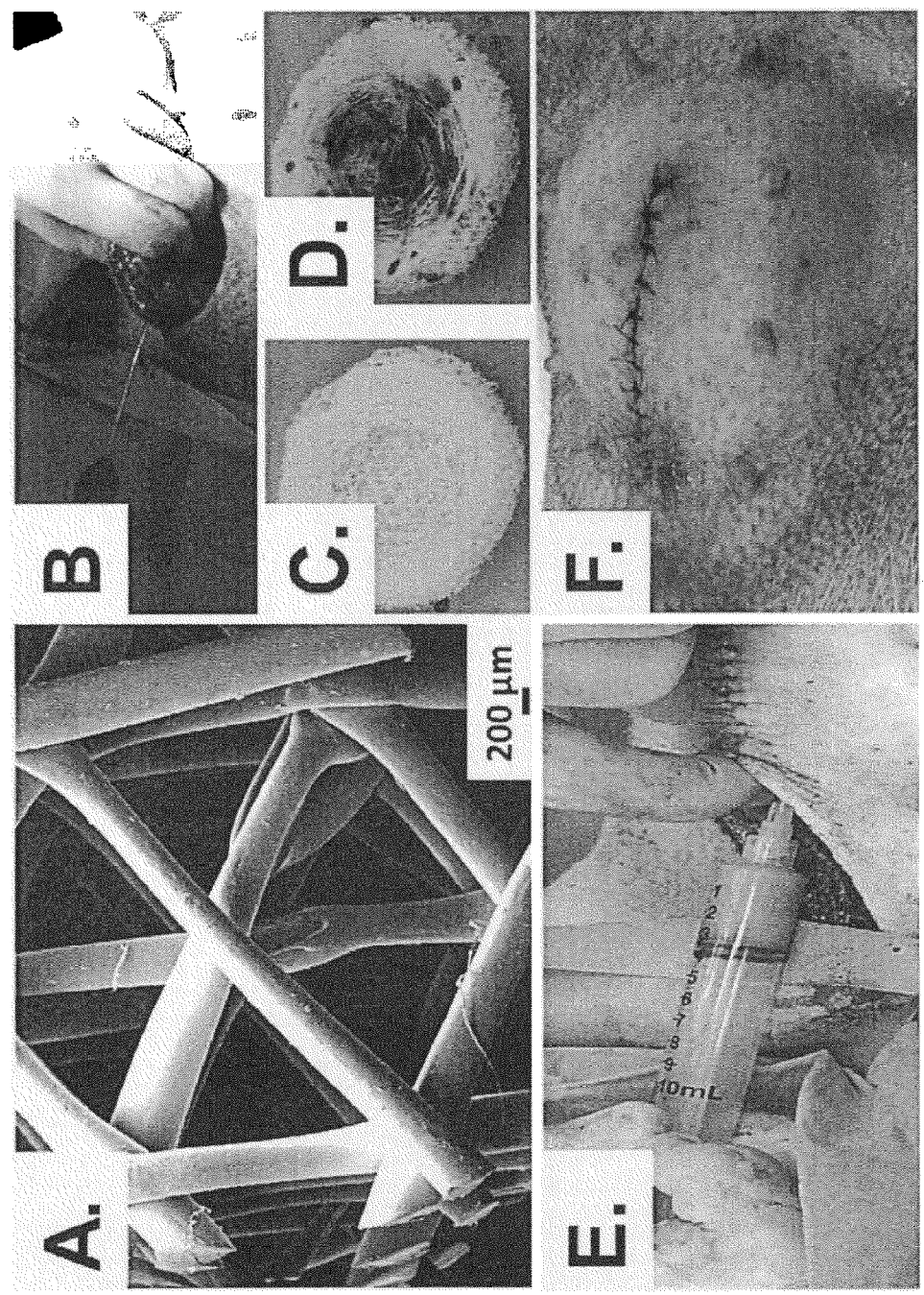
FIG. 13 (A) shows a scanning electron micrograph of the scaffold used in Example 1, showing the struts, pores and pore-interconnections. (B-F) Implantation process of the scaffolds as described in Example 1. (B) Liposuction procedure near the abdominal midline incision. (C, D) Process of injecting fat into the pores of the scaffold placed in the lipoaspirate only group. (C) shows an empty scaffold while (D) shows a completely filled scaffold. (E) shows the process of injecting fat into the prevascularisation+lipoaspirate group scaffolds. The scaffolds are placed empty into the implantation site and 2 weeks later, fat is injected into the scaffold pores while the scaffold remains implanted. (F) the final form of the scaffolds conforms highly to the natural breast shape. The physical and mechanical properties of the scaffolds used are shown in Table 1 below.

The overall geometry of the scaffold was similar to that of a silicone implant used for breast augmentation (FIG. 13). The high porosity value of the scaffolds (obtained from the manufacturer) implies that more volume is available for tissue ingrowth.

Scaffold Explantation and Degradation

As pointed out above, three study groups were evaluated in this study. After 6 months of implantation, the Tissue Engineered Constructs (TECs) were retrieved for histological analysis. The scaffolds were well integrated with the surrounding tissue and there was a widespread invasion of host vasculature into the constructs (FIG. 14C). Visual examination revealed that the overall shape of the scaffolds did not change drastically over the implantation period. All scaffolds showed good integration with the host tissues and large areas of fat and vascularisation were observed qualitatively on all scaffolds. Qualitatively, it was also clear that the prevascularisation+lipoaspirate group (FIG. 14 F, I) had the highest degree of vascularisation and fat tissue deposits, followed by the lipoaspirate-only group (FIG. 14 E, H). Although the empty scaffold-only group also showed deposits of adipose tissue (FIG. 14 D, G), they were not as widespread as in the other groups.

Formation of Vascularised Adipose Tissue

FIGS. 15-17 show representative H&E stained images of all scaffold groups after 24 weeks in vivo. All sections showed the typical ring-like morphology of fat tissue. Overall, multiple areas of well-vascularised adipose tissue were found in all groups.

H&E staining of tissue explanted from the empty scaffold group showed that although the newly infiltrated tissue was highly vascular, a majority of the tissue was connective tissue and collagen with only very small patches of fat tissue (FIG. 15) identified in the micrographs by their typical ring-like morphology and the empty vacuole in the middle of the cell. The deeper layers of the empty scaffolds also showed similar results.

FIG. 16 shows the H&E stained sections of the lipoaspirate-only group. Overall, a higher percentage of fat tissue compared to overall tissue area (referred to herein as relative tissue area) was observed in this group. The superficial layers of the scaffold especially showed widespread distribution of adipose tissue whose relative tissue area matched closely to that of native breast tissue. However, the deeper layers of the scaffold showed lower relative adipose tissue areas and lower degrees of vascularisation.

FIG. 17 shows the H&E stained sections of the prevascularisation+lipoaspirate group. This group showed the highest amount of fat tissue compared to all other groups. There were large highly vascularised regions of fat tissue interspersed between connective tissue. This tissue morphology was highly similar to that of native breast tissue (see FIG. 20). Furthermore, the relative adipose tissue area was also considerably higher in the deeper layers of this group compared to all other groups. These adipose tissue regions seemed to be better connected to each other and formed interconnected structures.

Figure 18:
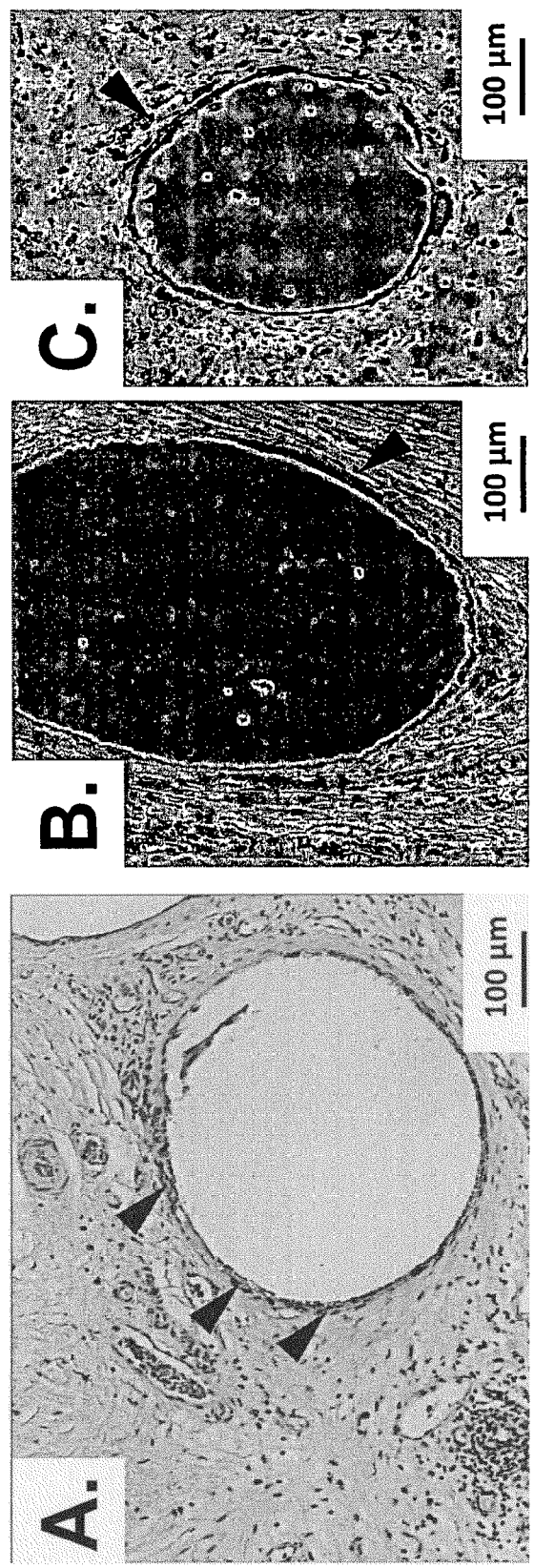
FIG. 18 depicts representative H&E-stained micrographs of regions around the scaffold strands showing non-specific minor granulomatose reactions. (A) shows the empty scaffold-only group, (B) shows the lipoaspirate-only group (C) shows the prevascularisation+lipoaspirate group. Arrow heads point to macrophages.

While no major signs of chronic inflammation were observed in the tissue sections or in the gross morphology of the constructs, non-specific localised low-grade granulomatose reactions were observed in the vicinity of the localised scaffold strands (FIG. 18). Lymphatic structures (FIG. 15, right panel) and leucocytes were also observed in all groups localised mainly near scaffold strands.

To identify the nature and composition of the connective tissue, Masson's trichrome staining was performed (FIG. 19A-F). In this staining, green colour indicates collagen fibres, red colour indicates muscle fibres and dark brown shows cell nuclei. As can be seen from the micrographs, besides the adipose tissue, a majority of the tissue filling the pores of the implant consisted of collagen fibres.

Thin layers of smooth muscle tissue were also observed, however it was only lining the boundaries of the scaffold strands. These smooth muscle layers had the highest thickness in case of the prevascularisation+lipoaspirate group (FIG. 19C).

In order to quantify adipose tissue regeneration, the total area of the adipose tissue relative to the total tissue area was counted on all slides (FIG. 19G). The negative control empty scaffold group had the lowest relative area of adipose tissue (8.31%±8.94) which was significantly lower than in both the lipoaspirate-only (39.67%±2.04) and the prevascularisation+lipoaspirate group (47.32%±4.12) and also compared to native breast tissue (44.97%±14.12) ($p<0.05$, $p<0.01$ and $p<0.01$ respectively). However, there was no statistically significant difference in relative adipose tissue area between the native breast tissue, lipoaspirate-only and prevascularisation+lipoaspirate group.

To quantify neovascularisation, blood vessels were counted on all slides (FIG. 19H). These blood vessels were identified by a ring/tubular structure, with only those lined with red blood cells included in the count as functional blood vessels. In general, all constructs, including the empty scaffold-only group, showed a substantial ingression of neovascularisation. The highest blood vessel density was observed in the prevascularisation+lipoaspirate group ($38.01/mm^2±2.02$), however the density was not statistically significantly higher than the scaffold-only ($33.13/mm^2±12.03$), lipoaspirate-only ($26.67/mm^2±1.6$) or control breast tissue ($35.45/mm^2±1.93$). H&E sections of constructs also showed blood vessels on and parallel to the surface of the constructs, suggesting that new capillaries are likely to have sprouted from these larger vessels that penetrated into the scaffolds.

Quantification of adipose cell area allowed the visualisation of the distribution of different-sized cells as a histogram (FIG. 19I). In all groups, the histograms were skewed to the right suggesting that a majority of adipose cell surface areas lay in the range of 100-700 $\mu m^2$. The distribution of the cell sizes in control breast tissue was considerably different compared to the other groups—with the highest percentage of cells in the 100-200, 300-400 and 500-600 $\mu m^2$ range. The empty scaffold and lipoaspirate-only groups had a low number of adipose cells having a surface area larger than 800 $\mu m^2$; whereas, the prevascularisation+lipoaspirate group showed a considerably higher number of cells having a surface area larger than 800 $\mu m^2$.

From data showing the percentage of adipose tissue area relative to total tissue area, the fold increase in adipose tissue volume was calculated (FIG. 19J, K). The prevascularisation+lipoaspirate group showed a higher fold increase in adipose tissue volume (6.1±0.62) compared to the lipoaspirate-only group (4.95±0.31); however, the difference was not statistically significant (p=0.143). Data for empty scaffold group has not been included because lipoaspirate was not injected into these scaffolds.

While cell-seeded anatomically shaped scaffolds are promising for the regeneration of complex, living tissue, they also lead to several disadvantages with problems ranging from scaling up of tissue culture to requiring complex GMP-approved laboratories for tissue culturing. The approach described in Example 1 circumvents such problems while scaling up the volumes of adipose tissue being regenerated by implanting an acellular scaffold and using the patient's body as a bioreactor. However, in the absence of a strong adipogenic stimulus, the scaffold gets filled with mostly non-specific fibrovascular tissue.

Here we have overcome the lack of adipogenic stimulus by injecting a small volume of lipoaspirate with no additional growth factors, cell transplantation or ligated vascular pedicles and introducing a completely novel prevascularisation technique that uses the patient's own body as a bioreactor and a source of blood vessels. Based on surgical expertise and the literature (Venkataram, 2008; Hanke et al., 1995; Gilliland and Coates, 1997; Housman et al., 2002), it was determined that 4 $cm^3$ of adipose tissue is close to the maximum amount of fat that can be safely harvested from patients with low body fat. In terms of percentage, it represents 5.3% of total volume of the scaffold at the time of implantation.

The delayed lipo-injection technique allowed the formation of a bed of vascular and connective tissue within the scaffold volume. Such a vascular and connective tissue supports early adipogenesis, provided sufficient mesenchymal stem cells or adipose progenitor cells have been recruited to the implantation site. Consequently, in the study of Example 1 the adipose tissue, when injected into the already prevascularised scaffold, remained stably within the implantation sites with no tissue necrosis and resorption. Over a period of 24 weeks, the fold increase in adipose tissue volume was found to be 4.95±0.31 in case of lipoaspirate-only and 6.1±0.62 in case of prevascularisation+lipoaspirate group.

For aesthetic breast augmentation, it may be advantageous if the regenerated tissue consists mainly of adipose tissue with smaller amounts of organised connective tissue in order to maintain the natural tactile sensation of the breast. In case of post-mastectomy breast reconstruction, it may be advantageous if the regenerated tissue is mostly composed of highly organised connective tissue, if adipose progenitor cells infiltrating into the scaffold are suspected to stimulate breast cancer recurrence via HGF/c-Met signalling. The results of this study indicate that the morphology of the regenerated tissue can be reproducibly controlled depending on the initial scaffold treatment strategy (empty scaffold vs. prevascularisation+lipoaspirate)—whereby empty scaffolds yield highly organised connective tissue whereas scaffolds containing lipoaspirate yield tissue rich in adipose tissue. In this way, scaffolds can truly be tailored for either an aesthetic augmentation procedure or a total reconstruction procedure.

Contrary to musculoskeletal systems, where tissue such as bone and muscle grow in response to mechanical forces, adipogenesis seems to be inhibited by mechanical forces. The scaffolds used in this study had a stiffness value that was 3 orders of magnitude higher than native breast tissue. By using mechanically robust scaffolds, a shielding effect can be exerted on the newly formed adipose tissue and the effects of the compressive, tensile and shear forces acting on the fat tissue can be reduced. This decreased mechanical stimuli can allow the cells to maintain a round morphology which, in turn, further promotes adipogenesis of the adipose progenitor cells (Nava et al., 2012).

As the skilled person is aware, the stiffness of the scaffolds may also be chosen dependent upon their placement. In case of most cosmetic augmentations whereby the implants are placed in a subglandular pocket, it is advantageous if the scaffold remains elastomeric and flexible so as to not cause patient discomfort; whereas in case of most post-mastectomy breast reconstruction procedures whereby the implants are placed in a submuscular pocket and no other supporting tissue remains, it is advantageous if relatively stiff implants are used in order to properly support the regeneration of the entire breast region (Vazquez et al., 1987).

Non-specific localised low-grade granulomatose reactions were observed in the vicinity of the localised scaffold strands. A granuloma is an organised collection of macrophages (Mukhopadhyay et al., 2012). While the roles of macrophages in angiogenesis are not yet completely understood, various research groups have shown that macrophages have the potential to contribute in angiogenesis. More specifically, M1 macrophages secrete VEGF which initiates the process of angiogenesis, M2a macrophages secrete PDGF-BB known to be involved in later stages of angiogenesis, while M2c macrophages secrete high levels of MMP-9 known to have a role in remodelling of vasculature. It has also been reported in the literature that macrophages can secrete alpha smooth muscle actin and can transdifferentiate into smooth muscle cells. All treatment groups examined showed accumulation of smooth muscle tissue around the scaffold strands (FIG. 19A-C) which indicates that macrophages may have played a role in angiogenesis and consequently higher adipogenesis in this group. Since the constructs were placed in PFA for an extended period of time post explantation, the proteins within the samples were denatured and immunohistology could therefore not be undertaken to provide direct evidence of this effect.

While no major outward signs of chronic inflammation were observed clinically or in the gross morphology of the constructs, lymphatic structures and leucocytes were detected in the histology of all treatment groups—which is to be expected because the study used an immunocompetent animal model. Polycaprolactone has met FDA approval and been proven in multiple independent studies to be cytocompatible. The increased leucocyte count may be explained by the fact that during the lipoaspiration process, adipose cells may have formed non-viable aggregates in the syringe which, when injected into the scaffold, triggered an autoimmune reaction from the host aiming to break them down, ultimately leading to the ingression of lymphatic vessels.

Amongst others, Example 1 shows that the prevascularisation and delayed fat injection technique can be used for efficient regeneration of large volumes of adipose tissue for long periods of time. Thus, the approach combining delayed fat injection with a biodegradable scaffold can be used for long-standing regeneration of clinically relevant volumes of adipose tissue.

Example 2

Breast shaped scaffolds made of poly(D,L)-lactide polymer and containing voids and space-occupying structures essentially as shown in FIG. 21, scaled up to a scaffold volume of 125 cm$^3$, were prepared. The scaffolds were fabricated with a 3D printer fitted with two extruders (one for printing poly(D,L)-lactide polymer for the scaffold structure, one for printing polylactic acid including a black dye for the space-occupying structures). Such a dual 3D print strategy also allows to prepare complex channel designs, if desired (e.g. a radially convergent design). Since the space-occupying structures are made of solid material, they are not degraded as quickly as the scaffold and thus are capable of preventing tissue/cell invasion within the rather short period of prevascularization in this example. With space-occupying structures made of an undegradable material, prevention of tissue/cell invasion is even better.

With such scaffolds, a pilot study was undertaken whereby n=6 scaffolds (volume=125 cm$^3$ each) were implanted in immunocompetent minipigs.

After 2 weeks of prevascularisation, the surgeon used a commonly used biopsy punch (FIG. 21 B) to remove the space-occupying structures. Adipose tissue was injected into the generated void spaces.

Upon explantation (24 weeks after implantation), it was observed that the scaffolds had been well integrated with the surrounding tissue and that there was a widespread invasion of host vasculature into the constructs. Visual examination revealed that the overall shape of the scaffolds did not change drastically over the implantation period. Histological evaluation showed large areas of fat and vascularisation at and around the sites where adipose tissue had been injected into the void spaces on all scaffolds (see FIG. 22).

Tables

TABLE 1

Physical and mechanical properties of the scaffolds used in Example 1.

| Elastic Modulus [MPa] | Porosity [%] | Scaffold Volume [mm$^3$] | Pore size [mm] |
|---|---|---|---|
| 21.5 ± 2.2 | 79.9 ± 1.56 | 75 × 10$^3$ | 0.46 |

REFERENCES

Chhaya, M. P., F. Melchels, B. M. Holzapfel, J. Baldwin, D. W. Hutmacher, *Sustained Regeneration of High-volume Adipose Tissue for Breast Reconstruction using Computer Aided Design and Biomanufacturing*. Biomaterials, 2015. 52: p. 551-60.

Flassbeck, D., et al., *Determination of siloxanes, silicon, and platinum in tissues of women with silicone gel-filled implants*. Analytical and bioanalytical chemistry, 2003. 375(3): p. 356-362.

Gilliland, M. D., N. Coates, *Tumescent liposuction complicated by pulmonary edema*. Plastic and reconstructive surgery, 1997. 99: p. 215-219.

Hanke, C. W., G. Bernstein, S. Bullock, *Safety of tumescent liposuction in 15,336 patients*. Dermatologic surgery, 1995. 21: p. 459-462. Henkel, J., M. A. Woodruff, D. R. Epari, R. Steck, V. Glatt, I. C. Dickinson, P. F. Choong, M. A. Schuetz, D. W. Hutmacher, *Bone Regeneration Based on Tissue Engineering Conceptions—A 21st Century Perspective*. Bone Research (1), 2013. P2.

Housman, T. S., N. Lawrence, B. G. Mellen, M. N. George, J. S. Filippo, K. A. Cerveny, M. DeMarco, S. R. Feldman, A. B. Fleischer, *The safety of liposuction: results of a national survey*. Dermatologic surgery, 2002. 28: p. 971-978.

Mukhopadhyay, S., C. F. Farver, L. T. Vaszar, O. J. Dempsey, H. H. Popper, H. Mani, V. L. Capelozzi, J. Fukuoka, K. M. Kerr, E. H. Zeren, *Causes of pulmonary granulomas: a retrospective study of 500 cases from seven countries*. Journal of clinical pathology, 2012. 65: p. 51-57.

Nava, M. M., M. T. Raimondi, R. Pietrabissa, *Controlling self-renewal and differentiation of stein cells via mechanical cues*. BioMed Research International, 2012.

Renneker, R. and M. Cutler, *Psychological problems of adjustment to cancer of the breast*. Journal of the American Medical Association, 1952. 148(10): p. 833.

Salgado, A. J., O. P. Coutinho, R. L. Reis, *Bone tissue engineering: state of the art and future trends*. Macromolecular bioscience, 2004. 4: p. 743-765.

Vazquez, B., K. S. Given, G. C. Houston, *Breast augmentation: a review of subglandular and submuscular implantation*. Aesthetic plastic surgery, 1987. 11: p. 101-105.

Venkataram, J., *Tumescent liposuction: A review*. Journal of cutaneous and aesthetic surgery, 2008. 1: p. 49.

The invention claimed is:

1. A breast implant for breast reconstruction or breast augmentation, comprising a three-dimensional scaffold structure, forming the overall shape of the breast implant, wherein said three-dimensional scaffold structure comprises holes and/or pores, which are suitable for being colonized by cells upon implantation, and in addition comprises voids, and wherein said voids are filled with space-occupying structures that are removably attached to said three-dimensional scaffold structure and that are configured to prevent invasion of one or both of tissue and individual cells into said voids, wherein said space-occupying structures are substantially not biodegradable within a time frame of six to eight weeks.

2. The implant according to claim 1, wherein said three-dimensional scaffold structure is made of biodegradable material.

3. The implant according to claim 2, wherein said biodegradable material is selected from the group consisting of polycaprolactone, poly(1,3-trimethylene carbonate), polylactide, polyglycolide, poly(ester amide), poly(ethylene glycol)/poly(butylene terephthalate), poly(glycerol sebacate), poly(1,8-octanediol-co-citric acid), poly(1,10-decanediol-co-D,L-lactic acid), poly(diol citrate), poly(glycolide-co-caprolactone), poly(1,3-trimethylene carbonate-co-lactide), poly(1,3-trimethylene carbonate-co-caprolactone) and a copolymer of at least two of these materials.

4. The implant according to claim 3, wherein said biodegradable material is either polycaprolactone or a copolymer of polycaprolactone and either poly-trimethylene carbonate or polylactide.

5. The implant according to claim 1, wherein said voids are interconnected with each other and are arranged in a convergent geometric orientation radiating from one origin.

6. The implant according to claim 1, wherein the voids are not interconnected and are arranged in a non-convergent geometric orientation.

7. The implant according to claim 1, wherein said space-occupying structures are collapsible.

8. The implant according to claim 7, wherein said space-occupying structures comprise either a liquid encased in a sheath that is impermeable to said liquid, or a hydrogel encased in a sheath that is impermeable to said hydrogel.

9. The implant according to claim 1, wherein said space-occupying structures comprise ferromagnetic or superparamagnetic material.

10. The implant according to claim 9, wherein said ferromagnetic or superparamagnetic material is a composite of a biocompatible polymeric material and of a biocompatible ferromagnetic material.

11. The implant according to claim 10, wherein said biocompatible polymeric material is polycaprolactone.

12. The implant according to claim 10, wherein said biocompatible ferromagnetic material is iron oxide.

13. The implant according to claim 1, wherein said space-occupying structures are coated with a coating that prevents tissue attachment.

14. The implant according to claim 13, wherein said coating is a coating which comprises a cell proliferation inhibiting drug.

15. The implant according to claim 13, wherein said coating comprises one or more of the drugs tacrolimus, everolimus and mitomycin c.

16. The implant according to claim 1, wherein said implant is selected from the group consisting of a breast implant, an implant of the salivary gland, a pancreas implant, a bone implant, an implant to reconstruct an anterior cruciate ligament tear, a craniofacial reconstruction implant, a maxillofacial reconstruction implant, a complex jaw surgery implant, a post tumor-resection reconstruction implant, an implant for tissue reconstruction after removal of a melanoma, an implant for tissue reconstruction after removal of a head and neck cancer, an ear implant, a nose implant, a chest wall reconstruction implant, an orthopedic surgery implant, a cartilage reconstruction implant and a delayed burn reconstruction implant.

17. The implant according to claim 1, wherein said three-dimensional scaffold structure comprises a stack of multiple interconnected layers, each layer being composed of a plurality of bars, wherein
 a) said bars have a zigzag structure or a wiggled structure; or
 b) the bars of every n-th layer within said stack have a zigzag structure or a wiggled structure whereas the bars of all other layers are straight bars, wherein n is an integer in the range of from 2 to 5; or
 c) each layer comprises bars that have a zigzag structure or a wiggled structure, wherein at least $1/10^{th}$ of the bars of each layer have a zigzag structure or a wiggled structure, whereas all the other bars of said layer are straight bars; or
 d) each n-th layer within said stack comprises bars that have a zigzag structure or a wiggled structure, wherein at least $1/10^{th}$ of the bars of said each n-th layer have a zigzag structure or a wiggled structure, whereas all the other bars of said each n-th layer within said stack and the bars of all other layers are straight bars, wherein n is an integer in the range of from 2 to 5; or e) at least ¹⁄₁₀ of the layers within said stack are layers that comprise bars having a zigzag structure or a wiggled structure, whereas the other layers are layers that comprise only straight bars.

18. The implant according claim 1, wherein said three-dimensional scaffold structure comprises a stack of multiple interconnected layers, each layer being composed of a plurality of parallel bars, wherein the layers within said stack are arranged such that the parallel bars of any layer X within the stack and the parallel bars of the layer subsequent to said layer X (i.e. layer X+1) form an angle of $(180/n)°$, wherein n is an integer in the range of from 2 to 10, and wherein the bars of the n-th subsequent layer with respect to a certain layer Y within the stack (i.e. layer Y+n) are offset with respect to the bars of said layer Y by a distance of 1/m times the distance between the parallel bars of said layer Y, wherein m is an integer within the range of from 2 to 5.

19. The implant according to claim 1, wherein said three-dimensional scaffold structure is formed from a shape-memory polymer (SMP).

20. The breast implant of claim 1, wherein the space-occupying structures are free of spaces within the space-occupying structures that are suitable to be invaded by said tissue and/or cells, allowing the space-occupying structures to be removed after connective tissue and vasculature has penetrated into the scaffold structure, making the voids available for introducing fat tissue or other transplantation cells.

21. The breast implant of claim 1, wherein the voids have a diameter of at least 3 mm and a length of at least 0.5 cm.

22. The breast implant of claim 1, wherein the voids have a diameter of at least 5 mm and a length of at least 1 cm.

* * * * *